(12) United States Patent
Fiorelli et al.

(10) Patent No.: US 10,488,307 B2
(45) Date of Patent: Nov. 26, 2019

(54) SYSTEMS, DEVICES, AND METHODS FOR IMPROVED TISSUE TREATMENT

(71) Applicant: DIGNITY HEALTH, Phoenix, AZ (US)

(72) Inventors: Roberto Fiorelli, Scottsdale, AZ (US); Gurpaul Singh Sidhu, Chandler, AZ (US)

(73) Assignee: Dignity Health, Phoenix, AZ (US)

( * ) Notice: Subject to any disclaimer, the term of this patent is extended or adjusted under 35 U.S.C. 154(b) by 0 days.

(21) Appl. No.: 16/044,503

(22) Filed: Jul. 24, 2018

(65) Prior Publication Data

US 2019/0178760 A1    Jun. 13, 2019

Related U.S. Application Data

(60) Provisional application No. 62/597,567, filed on Dec. 12, 2017.

(51) Int. Cl.
  *G01N 1/00* (2006.01)
  *G01N 1/31* (2006.01)
  *G01N 1/30* (2006.01)

(52) U.S. Cl.
  CPC .................. *G01N 1/31* (2013.01); *G01N 1/30* (2013.01)

(58) Field of Classification Search
  CPC ....................................................... G01N 1/00
  See application file for complete search history.

(56) References Cited

U.S. PATENT DOCUMENTS 5,382,414 A  *  1/1995  Lautenschlager .. B01D 11/0219
                                                    204/902
5,846,484 A     12/1998  Scarborough et al.
(Continued)

FOREIGN PATENT DOCUMENTS

CA        2259318 A1     1/1998
WO    2017/109201 A1     6/2017

OTHER PUBLICATIONS

Azaripour, Adriano et al., "A survey of clearing techniques for 3D imaging of tissues with special reference to connective tissue", Progress in Histochemistry and Cytochemistry, 51:9-23 (2016).
(Continued)

*Primary Examiner* — Jyoti Nagpaul
(74) *Attorney, Agent, or Firm* — Rodney J. Fuller; Booth Udall Fuller, PLC

(57) ABSTRACT

Provided herein are systems, devices, and methods for improved treatment of tissue, such as brain tissue. The improved treatment described herein can result in improved tissue penetration of various compounds and chemicals, such as stains and immunohistochemistry reagents. For example, provided herein is a pressurizing device that may include a chamber body having an opening in one of a top and a sidewall of the body, and may also include a chamber lid covering the opening and releasably coupled to the chamber body proximate the opening. The chamber lid and chamber body form an air-tight cavity. The pressurizing device may also have an inlet passing through one of the chamber body and the chamber lid and into the air-tight cavity. The device may also include a retainer coupled inside the air-tight cavity and configured to releasably couple to at least one tissue sample receptacles.

20 Claims, 29 Drawing Sheets

(56) References Cited

U.S. PATENT DOCUMENTS

| | | |
|---|---|---|
| 6,635,469 B1 | 10/2003 | Litt et al. |
| 6,649,368 B1 | 11/2003 | Aghassi et al. |
| 8,288,122 B2 | 10/2012 | O'Leary et al. |
| 2007/0014690 A1 | 1/2007 | Lawrence et al. |
| 2015/0017627 A1 | 1/2015 | Anderson et al. |
| 2015/0144490 A1 | 5/2015 | Deisseroth et al. |

OTHER PUBLICATIONS

Reveles, Kristian H. et al., "Advances and perspectives in tissue clearing using CLARITY", pp. 1-26, retrieved from http://dx.doi.org/10.1101/144378 (Jun. 2, 2017).

Shen, Helen, "See-through brains clarify connections", Nature, 496:151 (Apr. 11, 2013).

Susaki, Etsuo A. et al., "Advanced CUBIC protocols for whole-brain and whole-body clearing and imaging", Nature Protocols, 10(11):1709-1727 (2015).

Bouvier, David S. et al., "High Resolution Dissection of Reactive Glial Nets in Alzheimer's Disease", Scientific Reports, 6-24544, DOI: 10.1038/srep24544, pp. 1-15 (Apr. 19, 2016).

Chen, Lingling et al., "UbasM: An effective balanced optical clearing method for intact biomedical imaging", Scientific Reports, 7:12218, DOI:10.1038/s41598-017-12484-3, pp. 1-11 (Sep. 22, 2017).

CLARITY protocol, pp. 1-13 (May 2016).

Dobosz, Michael et al., "Multispectral Fluorescence Ultramicroscopy: Three-Dimensional Visualization and Automatic Quantification of Tumor Morphology, Drug Penetration, and Antiangiogenic Treatment Response", Neoplasia, 16(1):1-13 (Jan. 2014).

Erturk, Ali et al., "Imaging Cleared Intact Biological Systems at a Cellular Level by 3DISCO", Journal of Visualized Experiments, 89:e51382, pp. 1-12 (Jul. 2014).

Hsueh, Brian et al., "Pathways to clinical CLARITY: volumetric analysis of irregular, soft, and heterogeneous tissues in development and disease", Scientific Reports, 7:5899 DOI:10.1038/s41598-017-05614-4, pp. 1-16 (Jul. 19, 2017).

Belle, Morgane et al., "Tridimensional Visualization and Analysis of Early Human Development", Cell, 169:161-173 (Mar. 23, 2017).

Chesnick Ingrid E. et al., "Elevated Pressure Improves the Rate of Formalin Penetration while Preserving Tissue Morphology", Journal of Cancer, 1:178-183 (2010).

Lee, Eunsoo et al., "ACT-PRESTO: Biological Tissue Clearing and Immunolabeling Methods for Volume Imaging", Journal of Visualized Experiments, 118:e54904, pp. 1-9 (Dec. 2016).

Kim, Sung-Yon et al., "Stochastic electrotransport selectively enhances the transport of highly electromobile molecules", PNAS, published online as www.pnas.org/cgi/doi/10.1073/pnas.1510133112, pp. E6274-E6283 (Nov. 2, 2015).

Lai, Hei Ming et al., "Rationalisation and Validation of an Acrylamide-Free Procedure in Three-Dimensional Histological Imaging", PLOS One, DOI:10.1371/journal.pone.0158628, pp. 1-14 (Jun. 30, 2016).

Lee, Eunsoo et al., "ACT-PRESTO: Rapid and consistent tissue clearing and labeling method for 3-dimensional (3D) imaging", Scientific Reports, 6:18631, DOI:10.1038/srep18631, pp. 1-13 (Jan. 11, 2016).

Liebmann, Thomas et al., "Three-dimensional study of Alzheimer's disease hallmarks using the iDISCO clearing method", Cell Rep. 16(4):1138-1152 (Jul. 26, 2016).

Liu, A. K. L. et al., "Bringing CLARITY to the human brain: visualization of Lewy pathology in three dimensions", Neuropathology and Applied Neurobiology, 42:573-587 (2016).

Liu, A. K. L. et al, "Free of acrylamide sodium dodecyl sulphate (SDS)-based tissue clearing (FASTClear): a novel protocol of tissue clearing for three-dimensional visualization of human brain tissues", Neuropathology and Applied Neurobiology, 43:346-351 (2017).

Thurber, Greg M. et al., "Antibody tumor penetration: Transport opposed by systemic and antigen-mediated clearance", Adv. Drug Deliv Rev., 60(12):1421, pp. 1-32 (Sep. 2008).

Chung, Kwanghun et al, "Structural and molecular interrogation of intact biological systems", Nature, 497(7449):332-337, pp. 1-23 (May 16, 2013).

Tomer, Raju et al., "Advanced CLARIFY for rapid and high-resolution imaging of intact tissues", Nat Protoc. 9(7):1682-1697, pp. 1-33 (Jul. 2014).

Spence, Rory D. et al., "Bringing CLARITY to Gray Matter Atrophy", Neuroimage, 101:625-632, pp. 1-19 (Nov. 1, 2014).

Nojima, Satoshi et al., "CUBIC pathology: three-dimensional imaging for pathological diagnosis", Scientific Reports, 7:9269, DOI:10.1038/s41598-017-09117-0, pp. 1-14 (Aug. 24, 2017).

Phillips, Jonathan et al., "Development of passive CLARITY and immunofluorescent labelling of multiple proteins in human cerebellum: understanding mechanisms of neurodegeneration in mitochondrial disease", Scientific Reports, 6:26013, DOI:10.1038/srep26013, pp. 1-12 (May 16, 2016).

Renier, Nicolas et al., "iDISCO: A Simple, Rapid Method to Immunolabel Large Tissue Samples for Volume Imaging", Cell, 159:896-910 (Nov. 6, 2014).

Scott, Gregory D. et al., "Tissue Optical Clearing, Three-Dimensional Imaging, and Computer Morphometry in Whole Mouse Lungs and Human Airways", American Journal of Respiratory Cell and Molecular Biology, 51(1):43-55 (Jul. 2014).

Jensen, Kristian H. R. et al., "CLARITY-compatible lipophilic dyes for electrode marking and neuronal tracing", Scientific Reports, 6:32674, DOI: 10.1038/srep32674, pp. 1-10 (Sep. 6, 2016).

Stefaniuk, Marzena et al., "Light-sheet microscopy imaging of a whole cleared rat brain with Thy1-GFP transgene", Scientific Reports, 6:28209, DOI: 10.1038/srep28209 (Jun. 17, 2016).

Sung, Kevin et al., "Simplified three-dimensional tissue clearing and incorporation of colorimetric phenotyping", Scientific Reports, 6:30736, DOI: 10.1038/srep30736 (Aug. 8, 2016).

Susaki, Etsuo A. et al., "Whole-Brain Imaging with Single-Cell Resolution Using Chemical Cocktails and Computational Analysis", Cell, 157:726-739 (Apr. 24, 2014).

Susaki, Etsuo A. et al., "Whole-body and Whole-Organ Clearing and Imaging Techniques with Single-Cell Resolution: Toward Organism-Level Systems Biology in Mammals", Cell Chemical Biology, 23:137-157 (Jan. 21, 2016).

Tainaka, Kazuki et al., "Whole-Body Imaging with Single-Cell Resolution by Tissue Decolorization", Cell, 159:911-924 (Nov. 6, 2014).

Xu, Na et al., "Fast free-of-acrylamide clearing tissue (FACT)—an optimized new protocol for rapid, high-resolution imaging of three-dimensional brain tissue", Scientific Reports, 7:9895, DOI: 10.1038/s41598-017-10204-5, pp. 1-15 (Aug. 29, 2017).

Yu, Tingting et al., "Elevated-temperature-induced acceleration of PACT clearing process of mouse brain tissue", Scientific Reports, 7:38848, DOI:10.1038/srep38848, pp. 1-10 (Jan. 31, 2017).

Zheng, Huiyuan et al., "Simplified CLARITY for visualizing immunofluorescence labeling in developing rat brain", Brain Struct Funct. 221(4):2375-2383 (May 2016).

International Search Report and Written Opinion of the International Searching Authority for PCT application No. PCT/US2018/059070 dated Jan. 2, 2019.

Murray, Evan et al., "Simple, Scalable Proteomic Imaging for High-Dimensional Profiling of Intact Systems", Cell, 163:1500-1514 (Dec. 3, 2015).

\* cited by examiner

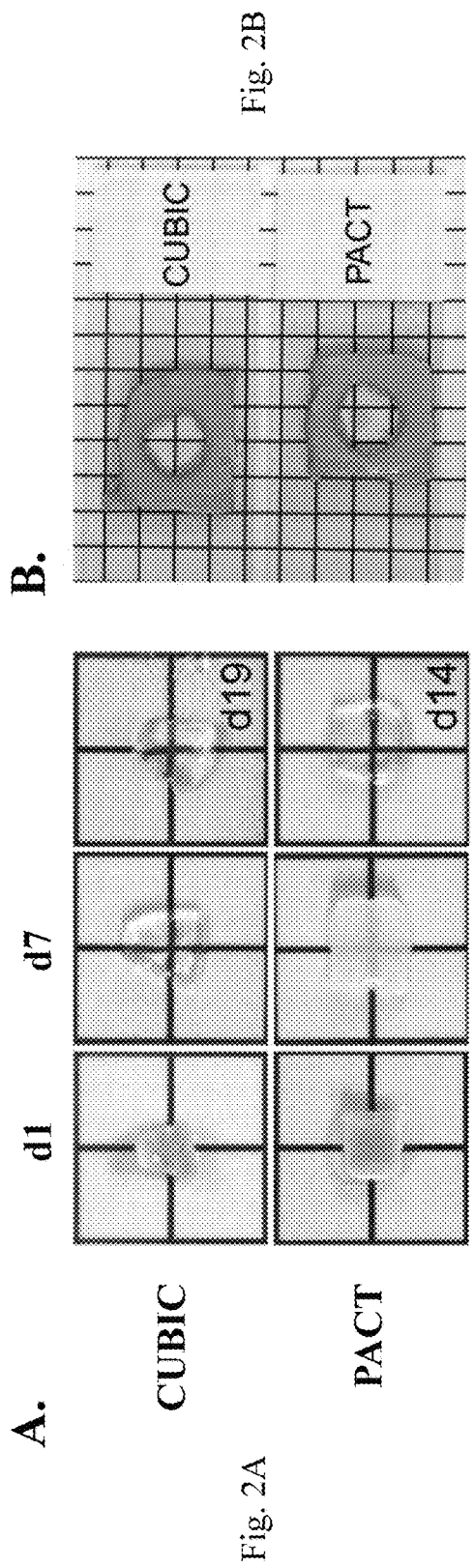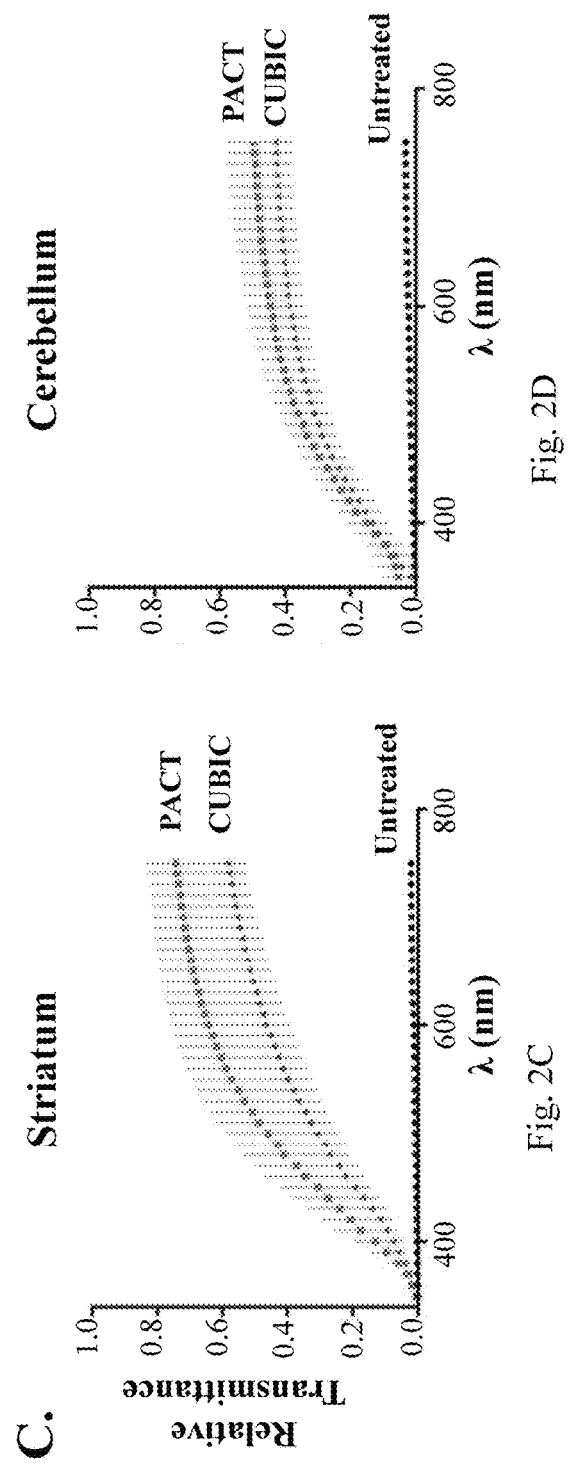
Fig. 2A
Fig. 2B
Fig. 2C
Fig. 2D

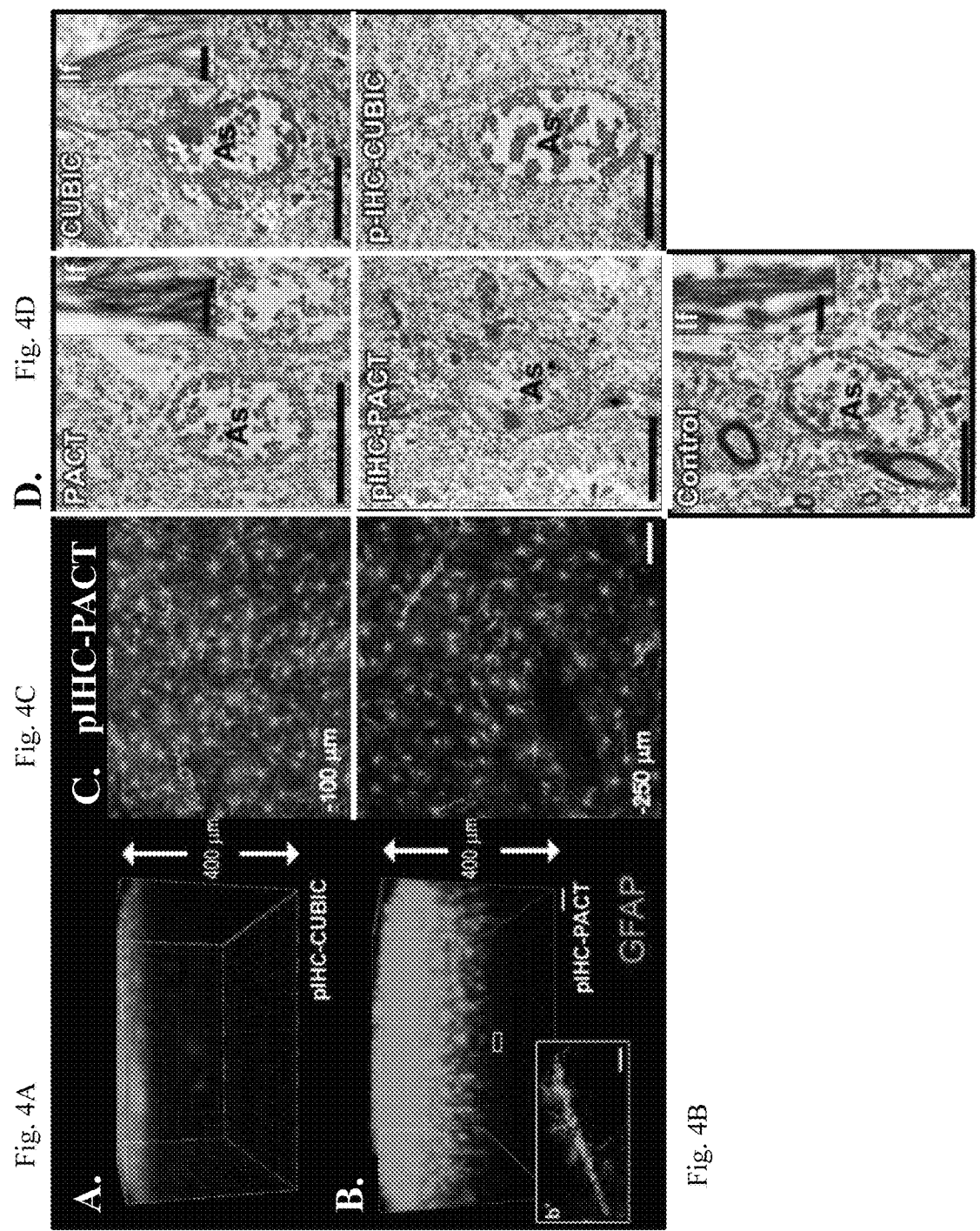

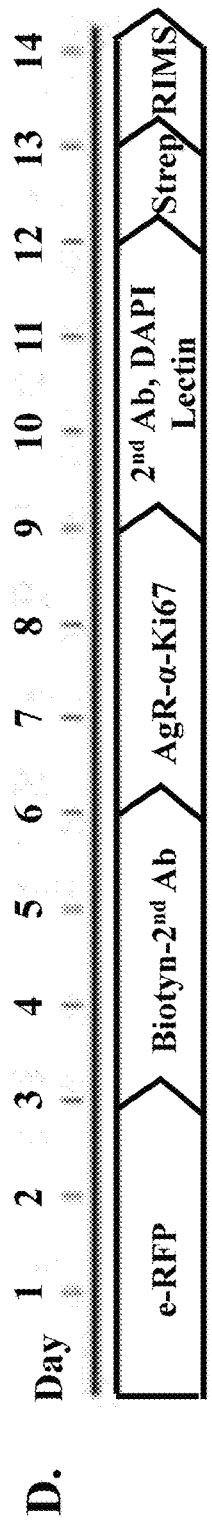
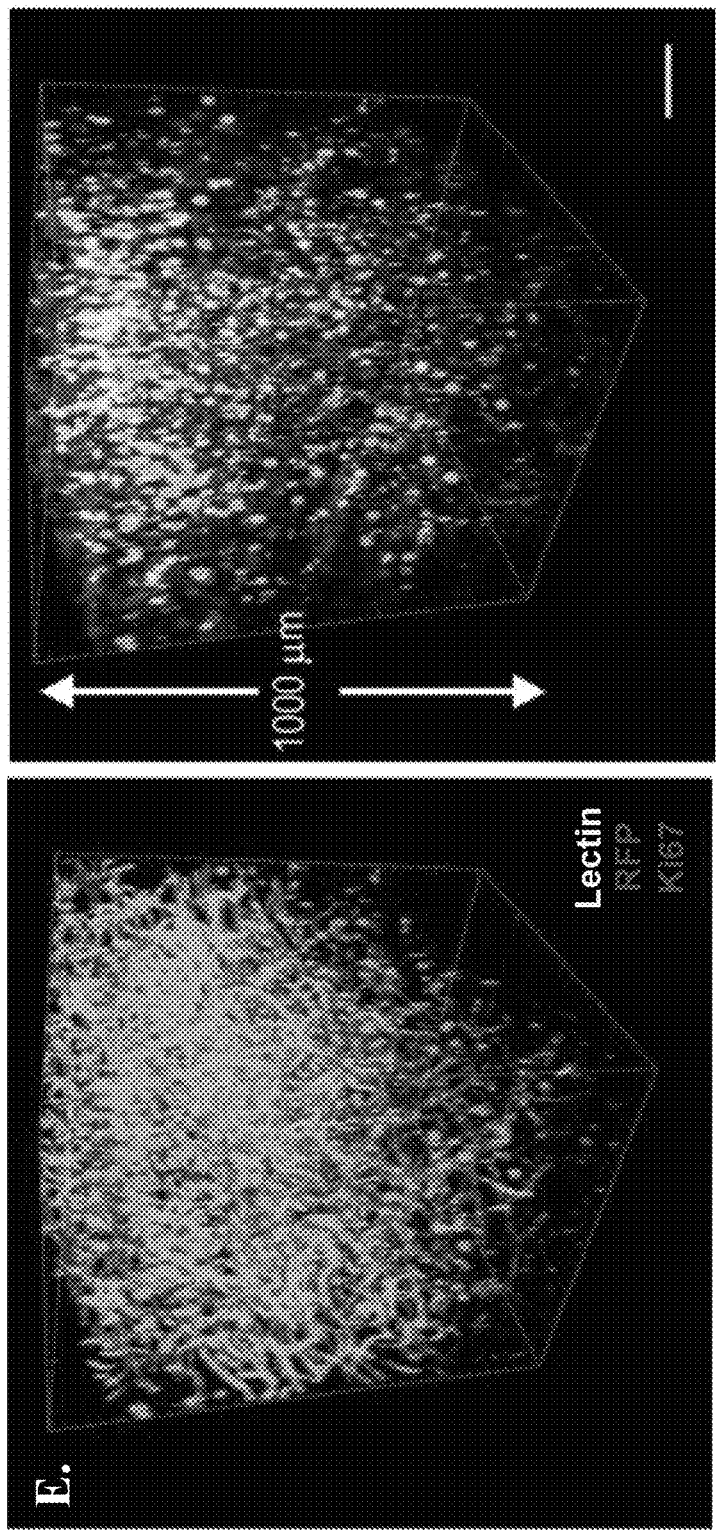
Fig. 9D
Fig. 9E

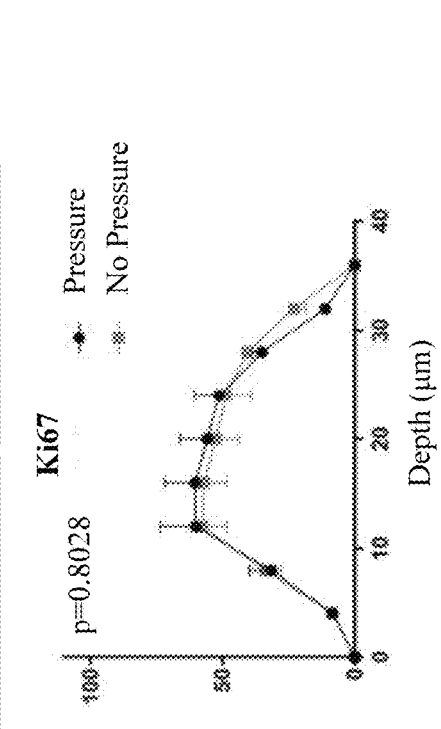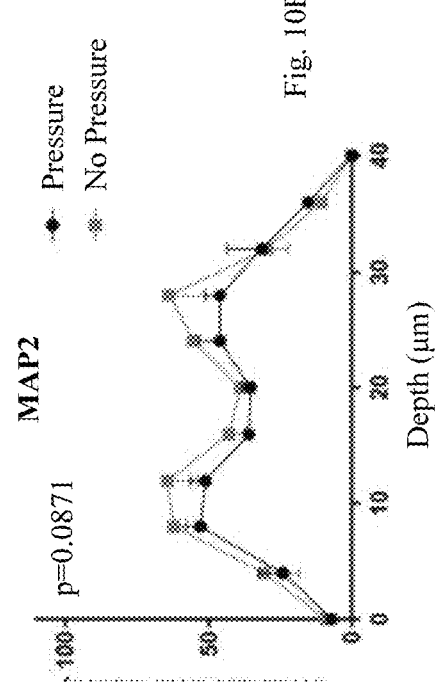
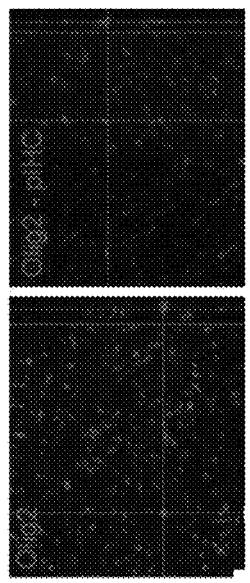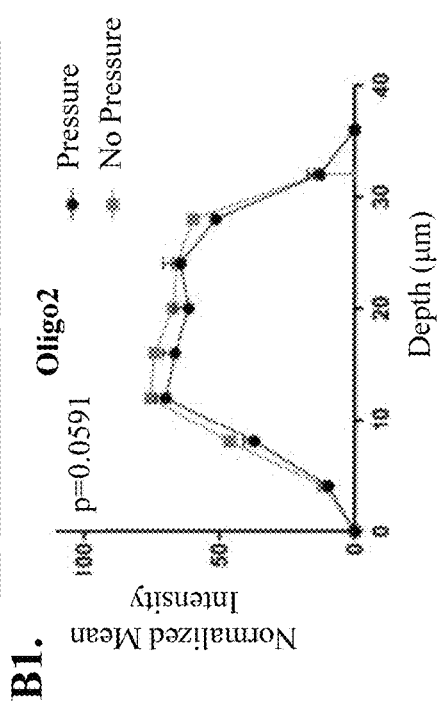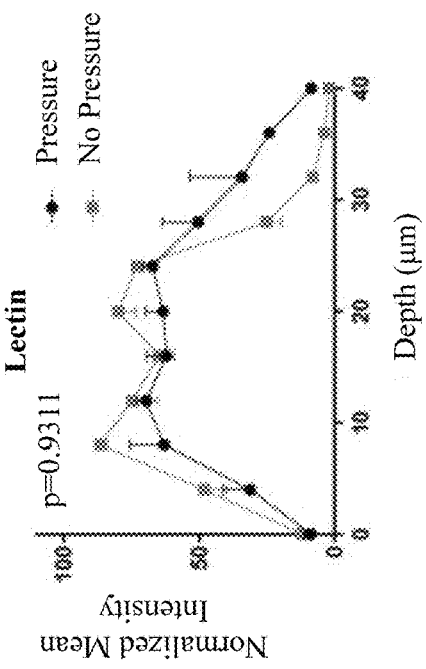
Fig. 10A1  Fig. 10B1

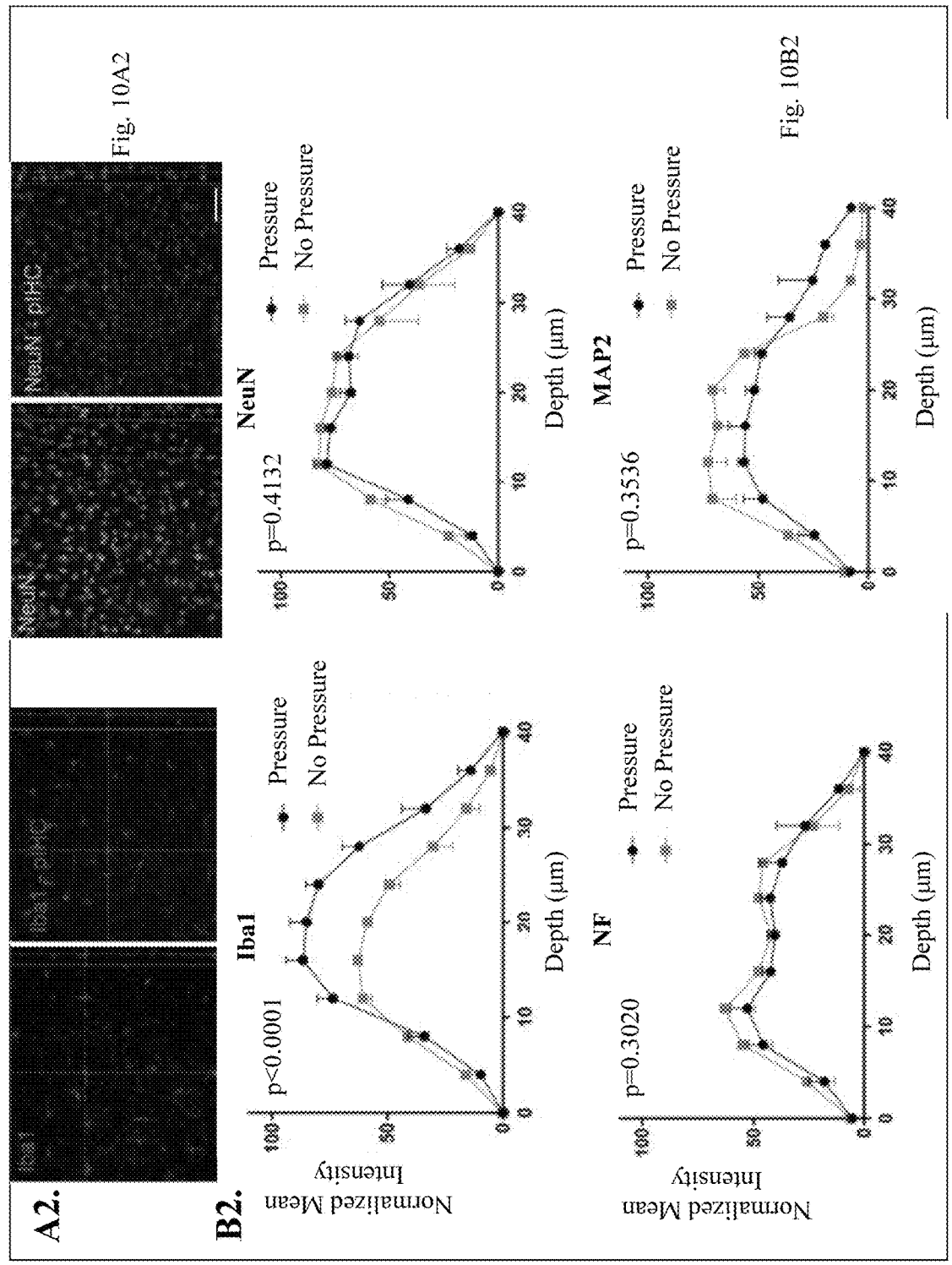

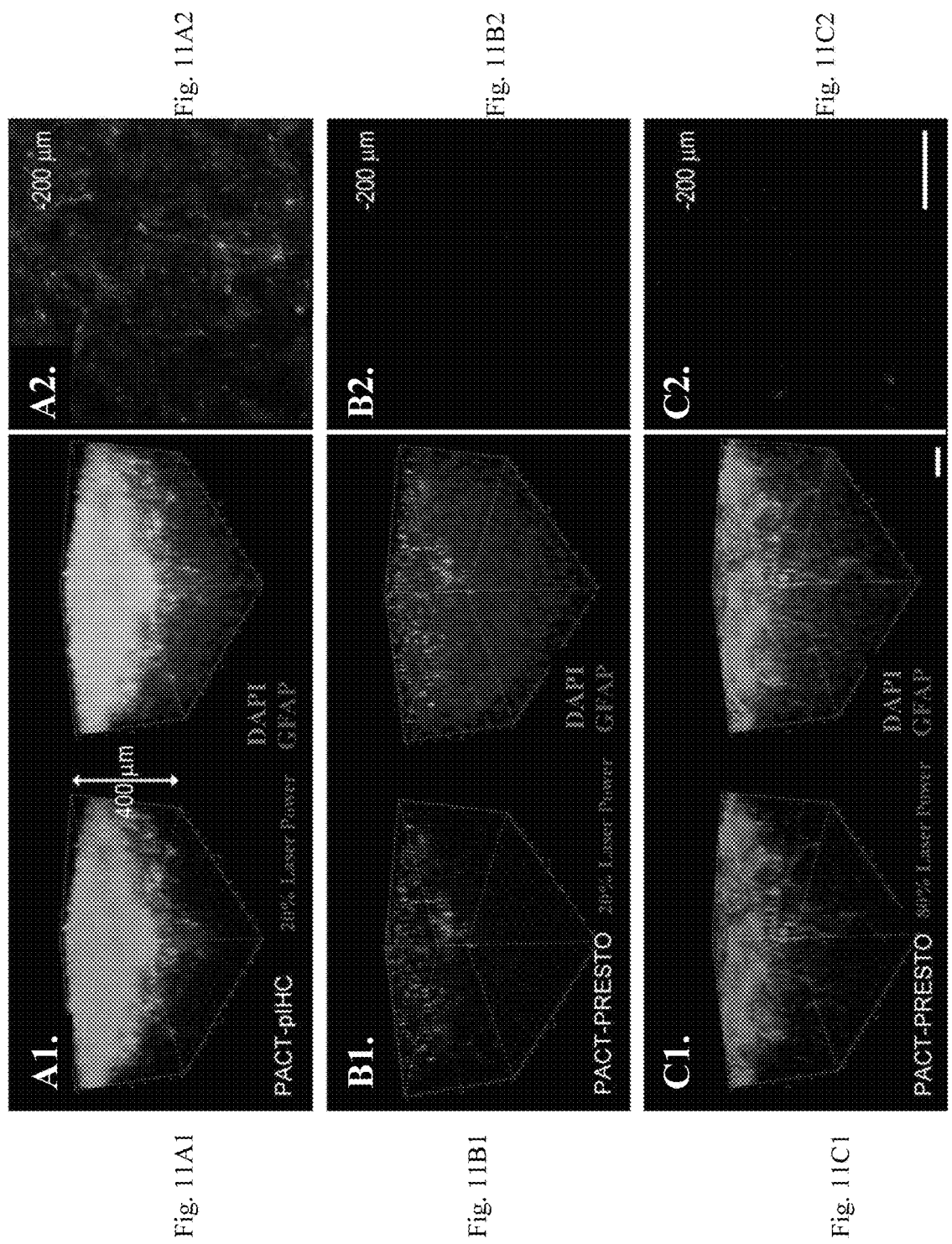

SYSTEMS, DEVICES, AND METHODS FOR IMPROVED TISSUE TREATMENT

CROSS-REFERENCE TO RELATED APPLICATIONS

This application claims the benefit of U.S. Provisional Patent Application No. 62/597,567, filed on Dec. 12, 2017, the contents of which is incorporated herein by reference in its entirety.

STATEMENT REGARDING FEDERALLY SPONSORED RESEARCH

This invention was made with government support under grant number R01NS082745 (Molecular Mechanisms Underlying Glioma Invasion of the Human Subventricular Zone) awarded by the National Institute of Neurological Disorders and Stroke (NIH). The United States government has certain rights in the invention.

TECHNICAL FIELD

At least some embodiments provided herein are generally related to systems, devices, and methods for improved tissue treatment and are specifically related to structures, systems, and methods that can be used to provide for improved staining (e.g., immunohistochemical, immunofluorescence, fluorescence, and/or colorimetric staining) of tissues, such as central nervous system-derived tissues.

BACKGROUND

Investigation of expression and localization of biomolecules (e.g., proteins) through the combination of immunohistochemistry (IHC) and light microscopy is a pivotal technique in diagnostic and basic research. Classic chromogenic IHC allows for 2-dimensional (2D) imaging of relatively thin tissue sections (e.g., 1-10 μm). Imaging of brain tissue in 3D is an essential technique to understand the cytoarchitecture and spatial relationship between cell populations. In general, processing and staining an organ and a tissue for 3D imaging provide a better understanding of complex biological processes. Specifically, understanding integrated 3D structure and fine molecular details throughout an organ or a tissue provide detailed insights into normal functions, and changes resulted from or giving rise to pathological states.

The introduction of fluorescent laser-scanning light microscopy in combination with imaging analysis software has allowed for 3-dimensional (3D) investigation of tissue architecture and protein localization in 10-50 μm sections. Before the introduction of clearing techniques, 3D imaging was limited to reconstructions of confocal stacks of thin sections, or digital reconstruction of macro-scale structures using annotation of multiple 2D images, a labor-extensive approach for partial or whole mouse brains[1], and human tissue blocks[2]. The introduction of tissue clearing techniques[3], beginning with the precursor CLARITY method[4], has advanced 3D histology by enabling imaging of relatively thick tissue samples (100 μm to several mm). Clarification methods reduce sample opacity generated by lipid-driven light scattering and make the organ or tissue transparent. Lipids are removed with detergents and replaced with a hydrogel matrix, allowing better penetration of excitation light as well as undisturbed detection of emission light. Several clearing methods are currently available, differing by the applications, the chemicals, the device, the procedure length, the degree of transparency, and the cost[3,5-7].

The current methods of processing and staining tissue exhibit several shortcomings. Some clearing methods, such as CLARITY®, require expensive equipment and fail to significantly improve staining beyond about 50 μm. While other methods provide for staining beyond 50 μm (e.g., 100 μm to greater than 2000 μm), application of those methods have been limited to animal models expressing a fluorescently-tagged protein, non-human (e.g., rat brain[8-12]), or non-complex tissues (e.g., tissues lacking the connective tissue present in adult tissues). Some methods also use reagents harsh to the samples, resulting in poor data quality.

Human tissues require immunohistochemistry (IHC) labeling. Particular challenges associated with fluorescent IHC of human tissues[6,13-15] (e.g., brain) include variability in the procurement process, fixing techniques, preservation, and internal sources of auto-fluorescence. The recent emergence of various clarification methods[5,14,16,17] allows post-mortem human brains to be cleared. IHC of thick samples, however, remains challenging. Due to the poor penetration of antibody molecules[18,19], passive diffusion of antibodies leads to inconsistent results in such samples. Reproducibility also remains an issue[14] of methods utilizing electric fields[19] or system-wide binding controlling agents[20]. Thus, methods and devices that improve processing and/or staining of relatively thick tissues, especially penetration of labeling agents (e.g., antibody) are needed in 3D imaging.

SUMMARY

According to one aspect, a pressurizing device for tissue preparation includes a chamber body that is hollow, having a top, a bottom, and at least one sidewall. The chamber body further includes an opening in one of the top of the chamber body and one of the at least one sidewall. The pressurizing device also includes a chamber lid covering the opening and releasably coupled to the chamber body proximate the opening through a plurality of bolts. The chamber lid and chamber body form an air-tight cavity. Furthermore, the pressurizing device includes an inlet passing through one of the chamber body and the chamber lid and into the air-tight cavity, as well as a retainer integral with the air-tight cavity. The retainer includes at least one biasing element coupled to the retainer. Each of the at least one biasing elements is positioned to press at least one sample receptacle against a portion of the retainer while the chamber lid is coupled to the chamber body.

Particular embodiments may comprise one or more of the following features. The retainer may further include a restrainer bar movably coupled to the chamber lid and biased away from the chamber lid by the at least one biasing element. The retainer may also include at least one bumper coupled to the chamber body opposite the restrainer bar. The restrainer bar may be positioned to press the at least one sample receptacle against the at least one bumper while the chamber lid is coupled to the chamber body. The pressurizing device may further include a plurality of leveling feet threadedly coupled to the chamber body. Each leveling foot of the plurality of leveling feet may be held a distance from the chamber body that may be adjustable by rotating the leveling foot. The pressurizing device may also include a cooling element that may be in thermal contact with the air-tight cavity, and/or a temperature sensor that may be coupled to the air-tight cavity. Finally, the air-tight cavity may have a height between one inch and three inches, and/or may have a volume between 25 cubic inches and 75 cubic inches.

According to one aspect, a pressurizing device for tissue preparation includes a chamber body having a top, a bottom, and at least one sidewall. The chamber body includes an opening in one of the top of the chamber body and one of the at least one sidewall. The pressurizing device also includes a chamber lid covering the opening and releasably coupled to the chamber body proximate the opening. The chamber lid and chamber body form an air-tight cavity. Furthermore, the pressurizing device includes an inlet passing through one of the chamber body and the chamber lid and into the air-tight cavity, as well as a retainer coupled inside the air-tight cavity and configured to releasably couple to at least one sample receptacle.

Particular embodiments may comprise one or more of the following features. The retainer may be integral with at least one of the chamber body and the chamber lid. The retainer may be releasably coupled to the air-tight cavity. The retainer may include at least one biasing element coupled to the retainer. Each of the at least one biasing elements may be positioned to press at least one sample receptacle against a portion of the retainer while the chamber lid is coupled to the chamber body. The pressurizing device may include a lid seal that may be composed of an elastomer and positioned around the opening and/or between the chamber body and the chamber lid when the chamber lid is releasably coupled to the chamber body. The chamber lid may be releasably coupled to the chamber body proximate the opening through a plurality of bolts. The at least one sample receptacle may be at least one of a single-well plate, a multi-well plate, a slide, an Eppendorf tube rack, and/or an Eppendorf tube. Finally, the pressurizing device may further include an electric agitator coupled to the chamber body. The electric agitator may be one of a motor, a linear actuator, and an ultrasonic emitter.

According to yet another aspect of the disclosure, a method for staining a biomolecule within biological tissue includes obtaining the tissue. The thickness of the tissue is 1-30,000 µm. The method also includes placing the tissue and a staining solution within a pressurizing device. The staining solution includes a biomolecule-specific agent. The method further includes applying an elevated pressure to the staining solution, and incubating the tissue in the staining solution under the elevated pressure for 1 minute to 7 days. Finally, the method includes recovering the tissue from the pressurizing device.

Particular embodiments may comprise one or more of the following features. The elevated pressure may be 2-30 ATM. The elevated pressure may be multidirectional. The thickness of the tissue may be between 2,500 µm and 30,000 µm.

Aspects and applications of the disclosure presented here are described below in the drawings and detailed description. Unless specifically noted, it is intended that the words and phrases in the specification and the claims be given their plain, ordinary, and accustomed meaning to those of ordinary skill in the applicable arts. The inventors are fully aware that they can be their own lexicographers if desired. The inventors expressly elect, as their own lexicographers, to use only the plain and ordinary meaning of terms in the specification and claims unless they clearly state otherwise and then further, expressly set forth the "special" definition of that term and explain how it differs from the plain and ordinary meaning. Absent such clear statements of intent to apply a "special" definition, it is the inventors' intent and desire that the simple, plain and ordinary meaning to the terms be applied to the interpretation of the specification and claims.

The inventors are also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventors are fully informed of the standards and application of the special provisions of 35 U.S.C. § 112, ¶6. Thus, the use of the words "function," "means" or "step" in the Detailed Description or Description of the Drawings or claims is not intended to somehow indicate a desire to invoke the special provisions of 35 U.S.C. § 112, ¶6, to define the invention. To the contrary, if the provisions of 35 U.S.C. § 112, ¶6 are sought to be invoked to define the inventions, the claims will specifically and expressly state the exact phrases "means for" or "step for", and will also recite the word "function" (i.e., will state "means for performing the function of [insert function]"), without also reciting in such phrases any structure, material or act in support of the function. Thus, even when the claims recite a "means for performing the function of . . . " or "step for performing the function of . . . ," if the claims also recite any structure, material or acts in support of that means or step, or that perform the recited function, then it is the clear intention of the inventors not to invoke the provisions of 35 U.S.C. § 112, ¶6. Moreover, even if the provisions of 35 U.S.C. § 112, ¶6 are invoked to define the claimed aspects, it is intended that these aspects not be limited only to the specific structure, material or acts that are described in the preferred embodiments, but in addition, include any and all structures, materials or acts that perform the claimed function as described in alternative embodiments or forms of the disclosure, or that are well known present or later-developed, equivalent structures, material or acts for performing the claimed function.

BRIEF DESCRIPTION OF THE DRAWINGS

FIG. 1A depicts a representative timeline that includes passive clearing step CUBIC (Top) or PACT (Bottom). "Reagent 1," "Reagent 2," and "SDS Clearing" summarize repeated incubation steps; 1ˆAb: primary antibody; 2ˆAb: secondary antibody; BW: boric acid wash; pIHC: pressurized immunohistochemistry; RIMS: refractive index matching solution; SDS: sodium dodecyl sulfate; W: washing step. FIG. 1B Comparative timelines between standard IHC and pIHC on relatively thin samples. Pressurization during blocking, 1ˆAb, and 2ˆAb significantly reduced the time necessary to complete the experiment.

FIGS. 2A-2D Examples of clearing methods. FIG. 2A Images of 1-mm thick human striatum during CUBIC (Top) or PACT (Bottom). FIG. 2B Images of mounted samples on conventional glass slides where chambers were created using Blu Tack. FIGS. 2C, 2D Relative transmittance of the visible light spectrum measured in 10 nm intervals through human striatal or cerebellar samples. Cerebellar measurements were performed through the white matter. Hence the relative lower transparency compared to the grey-matter rich striatal samples. Each condition was repeated for three times (N=3); error bars: SE; d: day.

FIG. 3A depicts that antibodies were unable to stain the entire 400 μm superficial section under free diffusion conditions. Scale bar: 200 μm. FIG. 3B Pressurization enhances the depth of antibody penetration independent of the clearing method. Images are z-stitched composites of 400 μm confocal acquisitions. Laser power was increased for deeper acquisitions. Scale bar: 200 μm. FIG. 3C Representative images of microglia cells (red) and arterioles (green) at different depths under pIHC-CUBIC. pIHC: pressurized immunohistochemistry; scale bar: 20 μm. FIG. 3D Fluorescence intensity along the z-axis under constant laser power. The X-axis shows the depth from 0 μm to 400 μm. Pressurization (black line) significantly increases staining intensity compared to free diffusion (grey line). Data were normalized to the maximum intensity value of a given staining independent of the condition. Data were analyzed using two-way ANOVA ($\alpha$=0.05) and the Šidák method for multiple comparisons. Each condition was repeated for three times (N=3); error bars: SE; the statistical difference between pressurization conditions was reported by p-values.

FIGS. 4A-4D 3D confocal acquisitions of human striatum immunolabeled with GFAP (green). FIG. 4A, 4B GFAP penetration in pIHC-CUBIC or pIHC-PACT samples. Scale bar: 50 μm. (FIG. 4B inset) Unassociated vascular cells (box) were detectable below maximum cellular staining depth. Scale bar: 5 μm. FIG. 4C Representative images of 20× single-plane fields showing consistent morphological appearances of astrocytes (green) at two different depths. Scale bar: 100 μm. FIG. 4D Transmission electron microscopy (TEM) micrographs showing conservation of astrocytes under different experimental conditions. Intermediate filaments were better conserved in PACT samples relative to CUBIC samples. Pressurization did not affect astrocytic ultra-structure. Scale bars: 5 μm (panel) 250 nm (inset); pIHC: pressurized immunohistochemistry.

FIG. 5A Confocal acquisition showing complete staining across a 1-mm z-plane of Laminin (red), a vascular-associated marker, in a pIHC-CUBIC cleared human striatum. Scale bar: 50 μm. FIG. 5B 400 μm-thick mosaic image of a 1.5×1.5 mm-area showing widespread diffusion of the Laminin staining. Scale bar: 100 μm. FIG. 5C Pressurized immunostaining of Laminin (red) and α-SMA (green), an arteriole-associated marker, in the pIHC-CUBIC treated human cortex. Arrows indicate a Laminin positive, α-SMA negative blood vessel. Co-localization is demonstrated in the remaining vasculature. Scale bar: 50 μm. FIG. 5D 3D view of a 400 μm confocal image of negative control. Pressurization (bottom) reduced background intensity relative to unpressurized samples (top). PACT samples (right) show co-occurrence of vascular-associated auto-fluorescence at the 488 nm and 568 nm excitation wavelengths, which is absent in CUBIC samples (left). Scale bar: 50 μm. FIG. 5E TEM analysis, showing a lack of identifiable erythrocytes in CUBIC samples. The blood vessels basal lamina is pseudo-colored in red. pIHC: pressurized immunohistochemistry; er: erythrocyte; scale bar: 2 μm. FIG. 5F High-magnification micrographs of cellular cytoplasms showing that pressurization increased protein aggregates in network distribution. Scale bar: 500 nm.

FIGS. 6A, 6B TEM micrographs showing the human cortex. Control: unpressurized tissue. pPACT, pCUBIC: cleared samples subjected to the same length of pressurization as in the pIHC protocol. Scale bar: 500 nm. Arrows indicate synaptic clefts, which are conserved in all conditions and not changed by pressurization. FIG. 6C Haematoxylin-Eosin staining of Control vs. cleared pressurized samples. Examination by a trained pathologist revealed no discernable differences between conditions. Some degree of tissue vacuolization can be seen in the pPACT sample. Scale bar: 100 μm.

FIG. 7A 3D view of 1.5-mm confocal acquisition from a pIHC-CUBIC treated human cortex immunolabeled with Fibronectin (green), Map2 (red), and DAPI (blue). Pial vessels stained with Fibronectin perforate the cortex where layer I and layer II/III (cortical layers 1 and 2/3) are recognizable through the Map2 staining. Scale bar: 100 μm. FIG. 7B Top and side views of CUBIC-cleared human cortex stained under free diffusion, demonstrating pia membrane's blockage of antibody penetration. Scale bar: 100 μm. FIG. 7C Top and side views of CUBIC-cleared human cortex stained using pIHC. Pressurization improves antibody penetration and reduces non-specific fluorescence at the surface of the tissue. Scale bar: 100 μm. FIG. 7D TEM micrographs showing the effect of different treatment. The profile of neurons that conserved the integrity of the cytoplasmic membrane is Pseudo-colored (blue). Neurons can be better distinguished from their surroundings in CUBIC samples compared to PACT samples. pIHC: pressurized immunohistochemistry; scale bar: 5 μm.

FIGS. 9A-9E Compatibility of pressurization with mouse brain stainings. FIG. 9A 400 μm-thick mosaic confocal acquisition of a 2.25×1.5 mm area of a mouse brain xenografted with RFP$^+$ human glioblastoma (GB3) cells (red) and stained with vascular marker Tomato Lectin-488 (green). Tumor core (GBM) in the striatal area and migratory route through the callosum are visible. Scale bar: 500 μm. FIG. 9B Confocal acquisition showing complete staining through a 1.2 mm thick pIHC-CUBIC cleared mouse sample for Lectin-568 (red), a vascular marker. Scale bar: 200 μm. FIG. 9C 400 μm-thick mosaic confocal acquisition of a 3×2.25 mm mediolateral brain area. pIHC was labeled for GB3-RFP (red), Sox2 (green), Vimentin (cyan), and DAPI (blue). Sox2 co-localization is seen with both the tumor environment and migrating tumor cells. Vimentin stains the tumor core area and the pial surface of the temporal cortex, including cortical vessels. Scale bar: 1 mm. FIG. 9D Experimental timeline for Ki-67 staining requiring heat mediated antigen retrieval and endogenous RFP rescue. Washing steps are omitted from the scheme. FIG. 9E 3D views of confocal acquisition showing complete staining through a 1 mm-thick pIHC-CUBIC sample of tumor core. (Left) Lectin (cyan) and Ki-67 (green); (Right) RFP (red) and Ki-67 (green). The consistent presence of Ki-67 staining across the tumor core illustrates the compatibility of pIHC with advanced staining protocols requiring antigen retrieval. pIHC: pressurized immunohistochemistry; $2^{nd}$ Ab: secondary antibody; Biotyn: biotinylated secondary antibody; AgR:

Antigen Retrieval; Strep: streptavidin; RIMS: refractive index matching solution; scale bar: 100 μm.

FIGS. 10A1-10B2. Pressurization accelerates staining of thin sections. FIGS. 10A1 & 10A2 Representative 20× images of immunostainings for Olig2, Ki67, Iba1, and NeuN using traditional (left) or pIHC method (right) on a GBM xenograft mouse model. Consecutive 40 μm thick serial sections were used, and comparative imaging was performed on anatomically-matching areas. Crosshairs are employed to indicate marker-positive cells located in the center of the tissue. Olig2 and Ki67 show tumor core areas. Iba1 shows tumor rim area. NeuN shows tumor-free cortical area. No difference in cellular density. Scale bar: 100 μm. FIGS. 10B1 & 10B2 Fluorescence intensity across the z-axis for Olig2, Lectin, Ki67, Map2, Iba1, Neurofilament (NF), NeuN, and GFAP stainings. Pressurization shows no significant difference in staining intensity relative to traditional IHC exception Iba1 where pressurization results in higher intensity in the center of the section. Data were normalized relative to the maximum intensity value of a given staining independent of condition. Data were analyzed using a two-way ANOVA test ($\alpha=0.05$) and the Šidák method for multiple comparisons. Statistical significance between staining conditions is reported by p-values. Error bars: SE; N=3 repeats for each condition; 1^Ab: primary antibody; 2^Ab: secondary antibody; IHC: immunohistochemistry; pIHC: pressurized immunohistochemistry; W: washing step.

FIGS. 11A1-C2 Comparison of pIHC and PRESTO. FIGS. 11A1, B1, C1 3D views of 400 μm confocal acquisitions of immunostaining of GFAP (green) and DAPI (blue). FIGS. 11A2, B2, C2 2D single plane stacks of immunostaining of GFAP. Combination of pIHC and PACT (FIG. 11A1) results in superior intensity and depth of GFAP staining compared to PRESTO (FIG. 11B1). pIHC staining reached 200 μm below tissue surface (FIG. 11A2) while PRESTO did not reach such depth (FIG. 11B2). DAPI penetration was comparable between the two methods. At fixed laser power (e.g., 20%), pIHC generated higher staining intensity. PRESTO GFAP staining was imaged by increasing laser power (e.g., 80%), which also increased non-specific vascular autofluorescence (FIG. 11C1), while still revealing the absence of GFAP staining 200 μm below tissue surface (FIG. 11C2). All scale bars: 200 μm.

Figure 12:
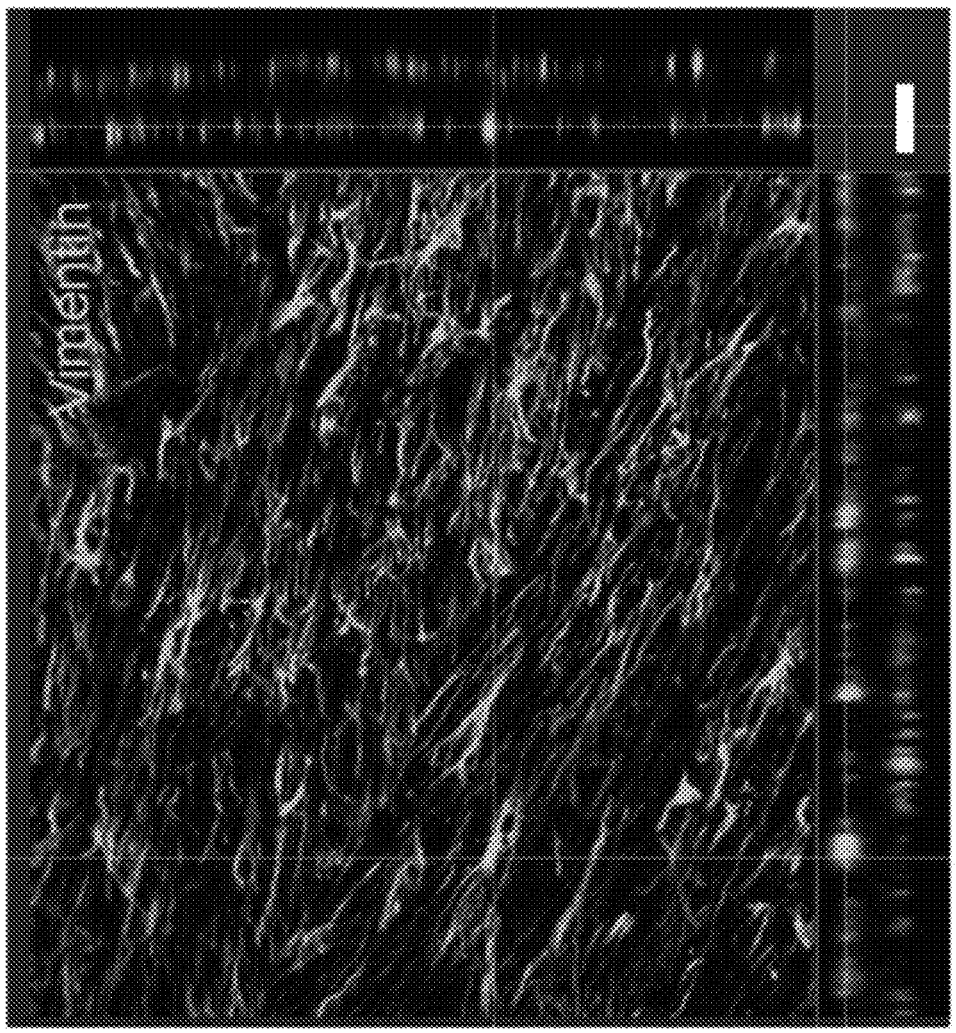

FIG. 12 Penetration of anti-Vimentin antibody in xenograft tumor tissue. Vimentin (cyan) generates strong staining on the surface (crosshair) of a 40 μm mouse GBM xenograft section, with a scarce signal in the center of the z-plane. Scale bar: 20 μm.

Figure 13:
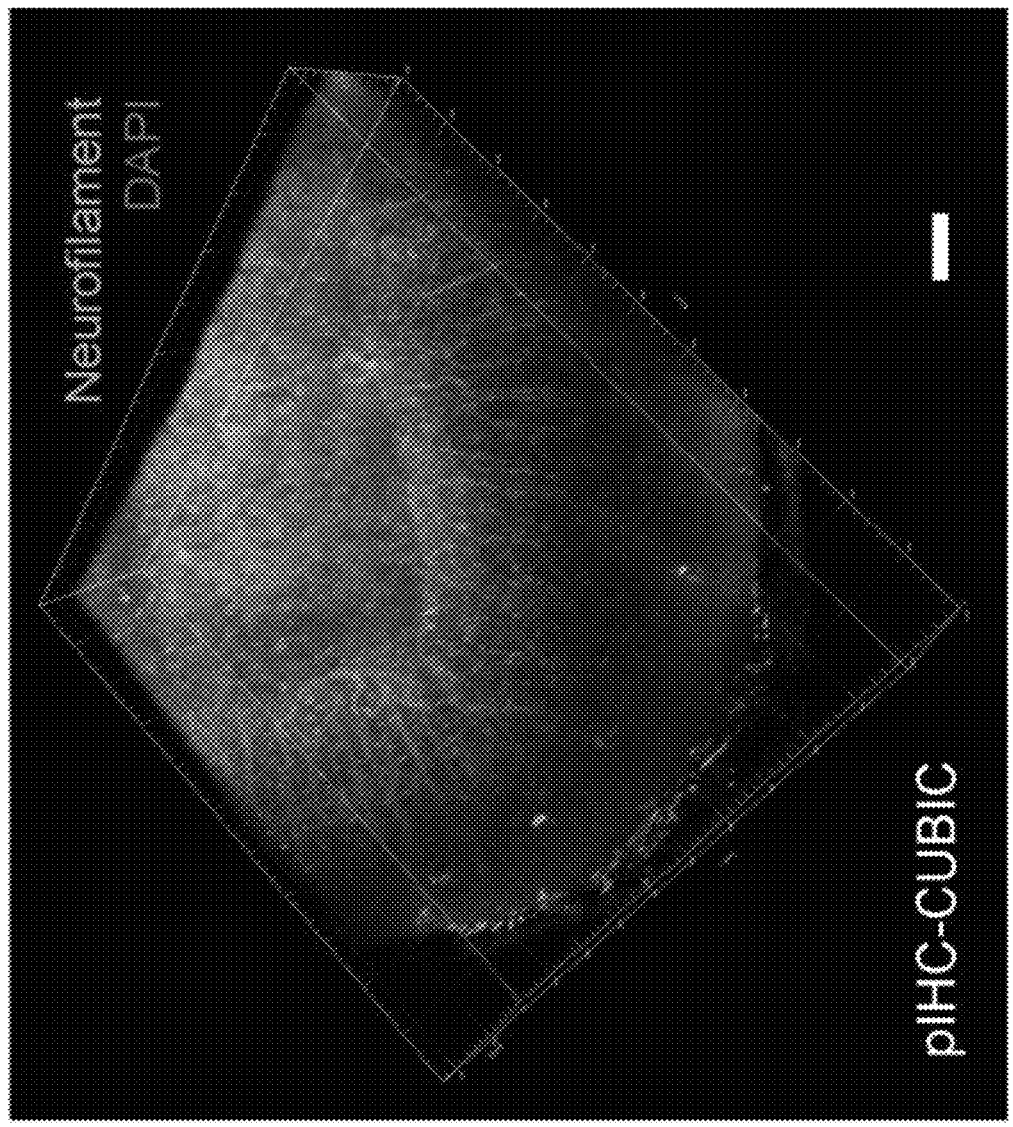

FIG. 13 Scarce penetration of Neurofilament antibody in a pIHC-CUBIC human cerebellar sample. 3D view of a 400 μm-thick confocal acquisition. Neurofilament antibody (green) failed to penetrate below the superficial 50 μm in a sample of the human cerebellar cortex. Scale bar: 100 μm.

Figure 14:
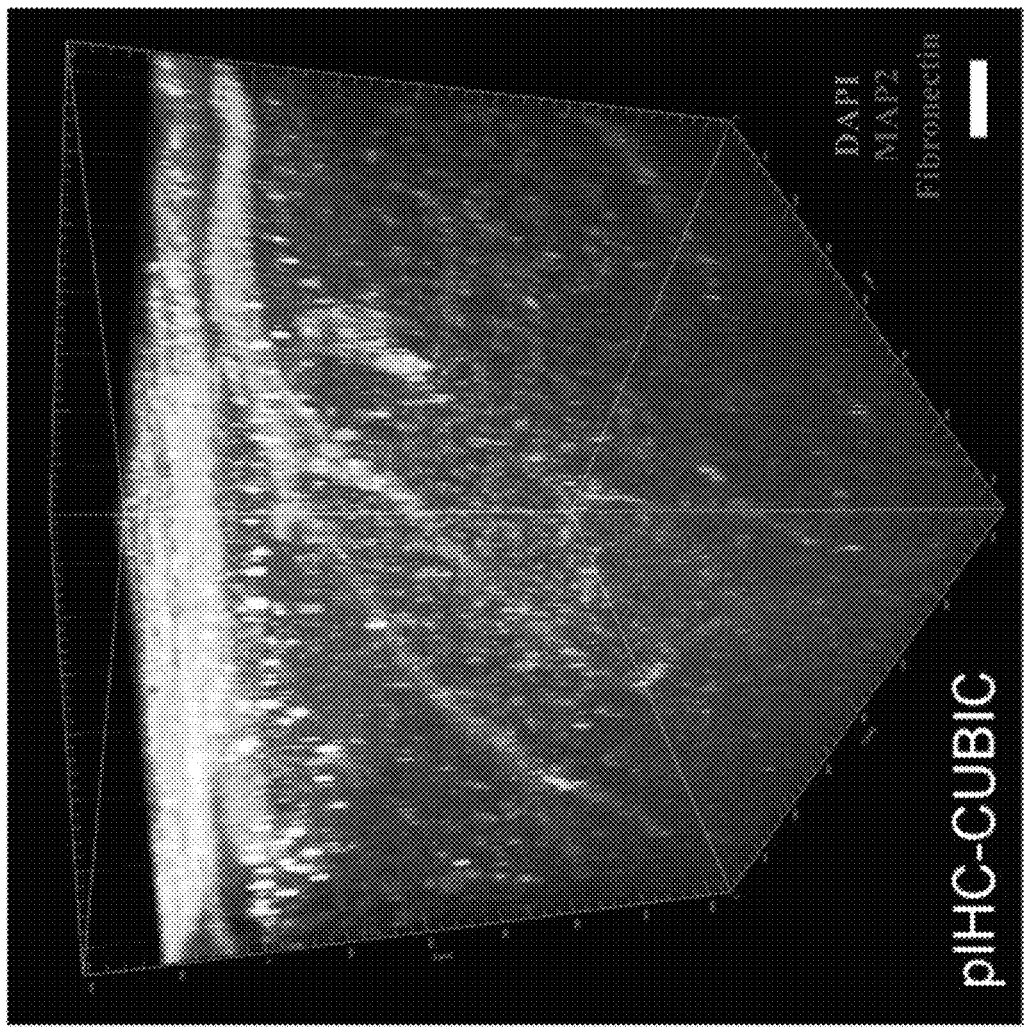

FIG. 14 Re-imaging of pIHC 8 months after experiment completion. Re-imaging of the sample used in FIG. 7A 8 months after completion. MAP2 (red), Fibronectin (green), and DAPI (blue) did not show fading in the first 800 μm from the surface. Scale bar: 100 μm.

Figure 15:
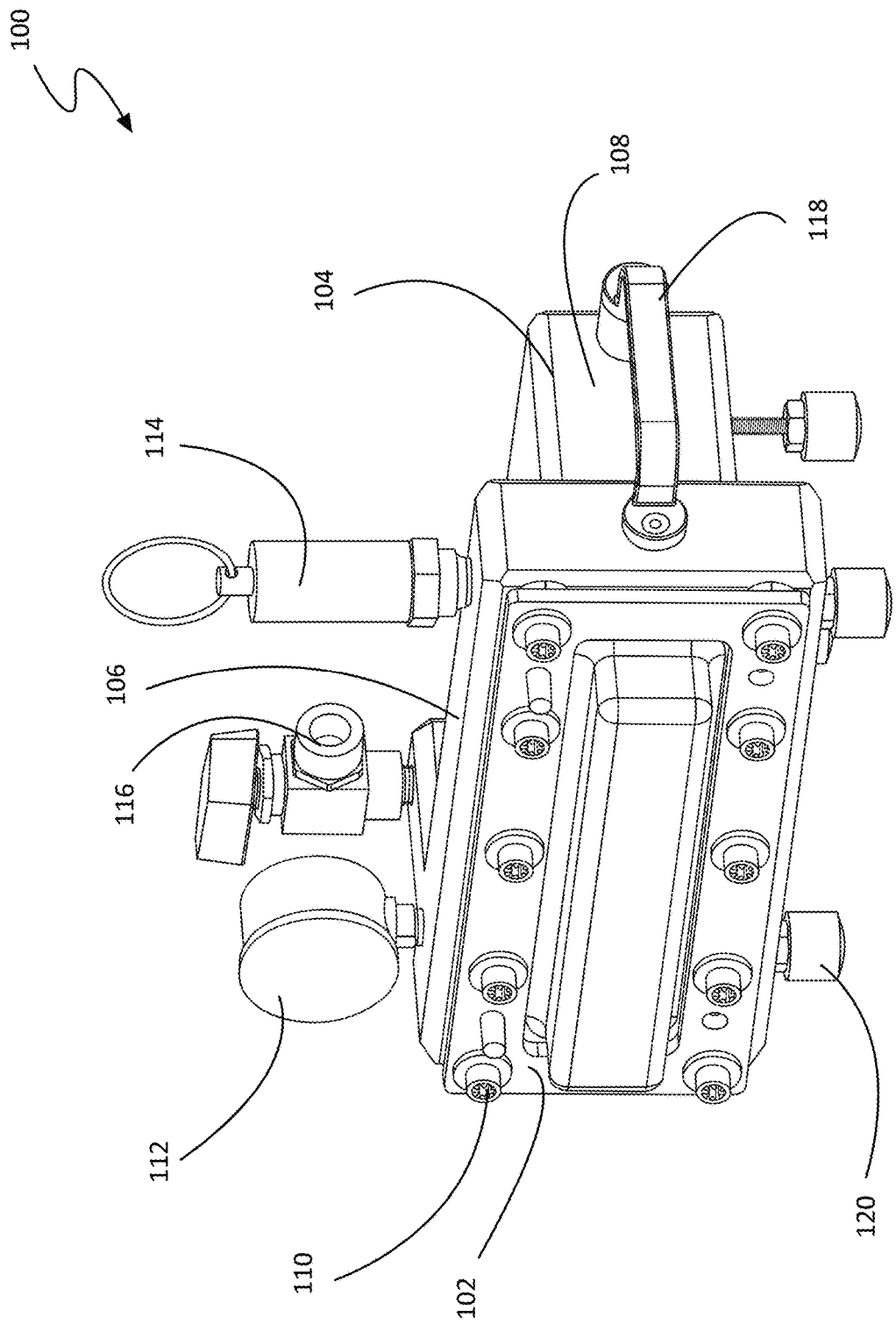

FIG. 15 is a perspective front view of a pressurizing device in a closed configuration.

Figure 16:
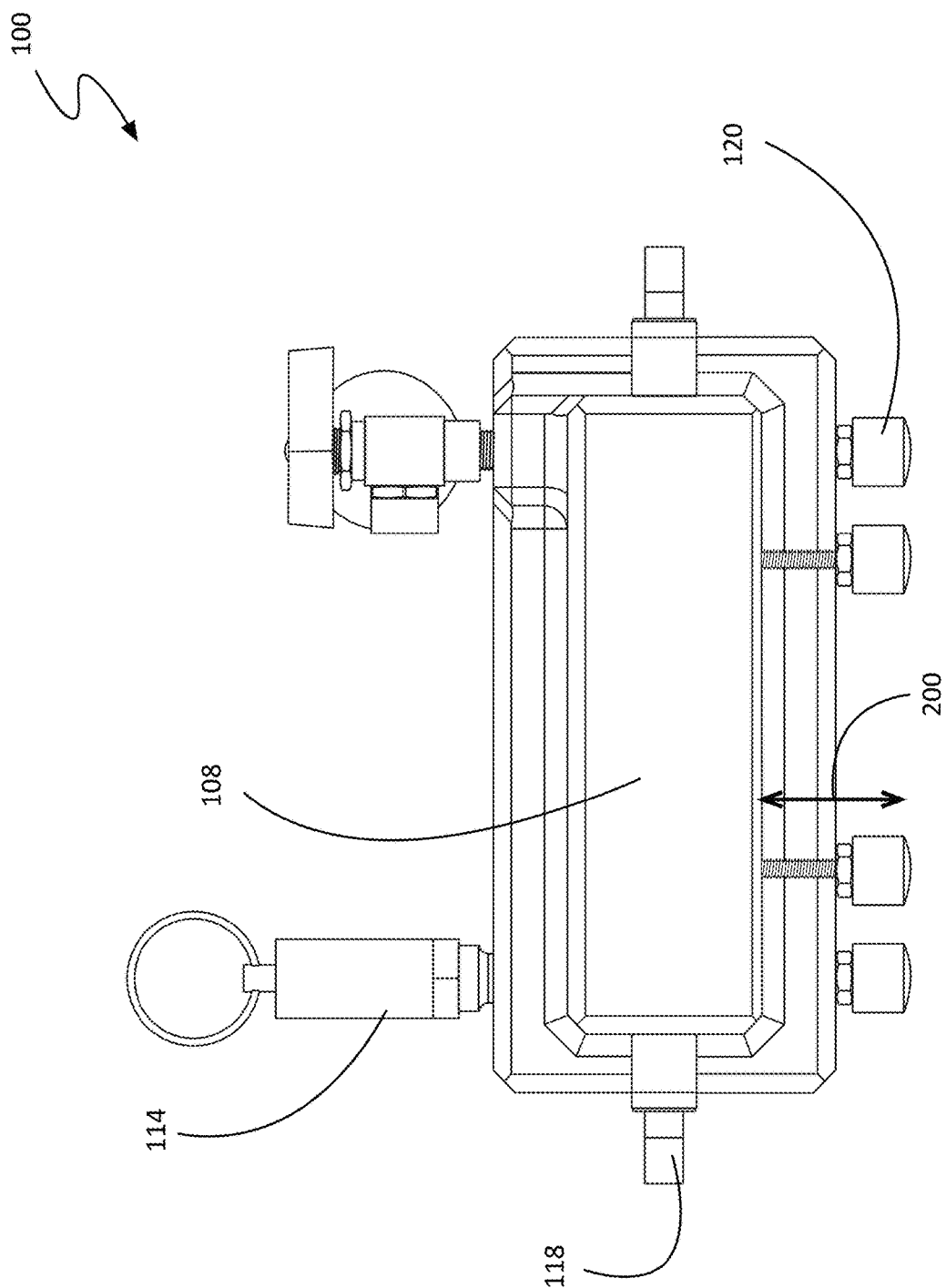

FIG. 16 is a back view of the pressurizing device of FIG. 15.

Figure 17:
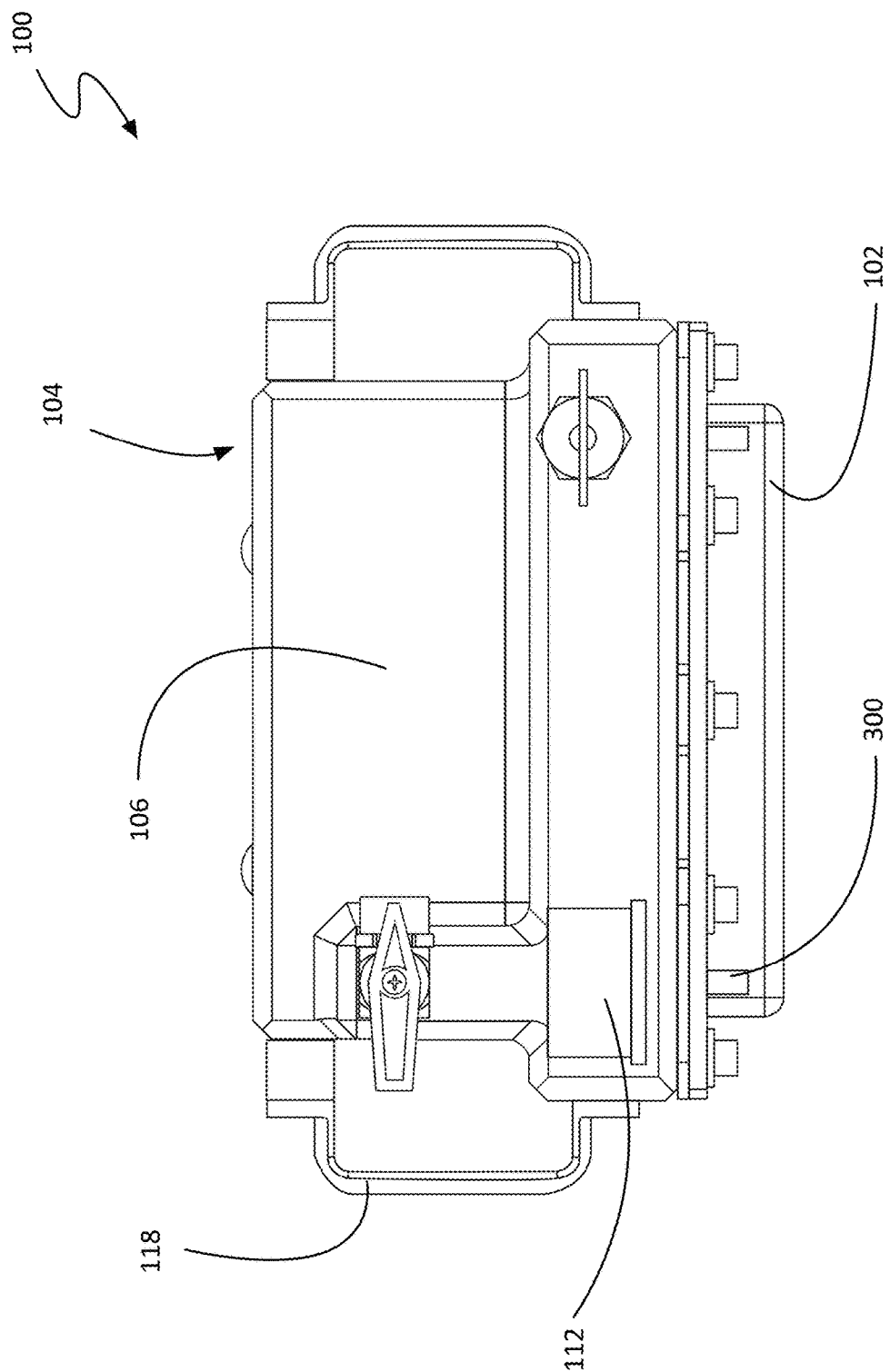

FIG. 17 is a top view of the pressurizing device of FIG. 15.

Figure 18:
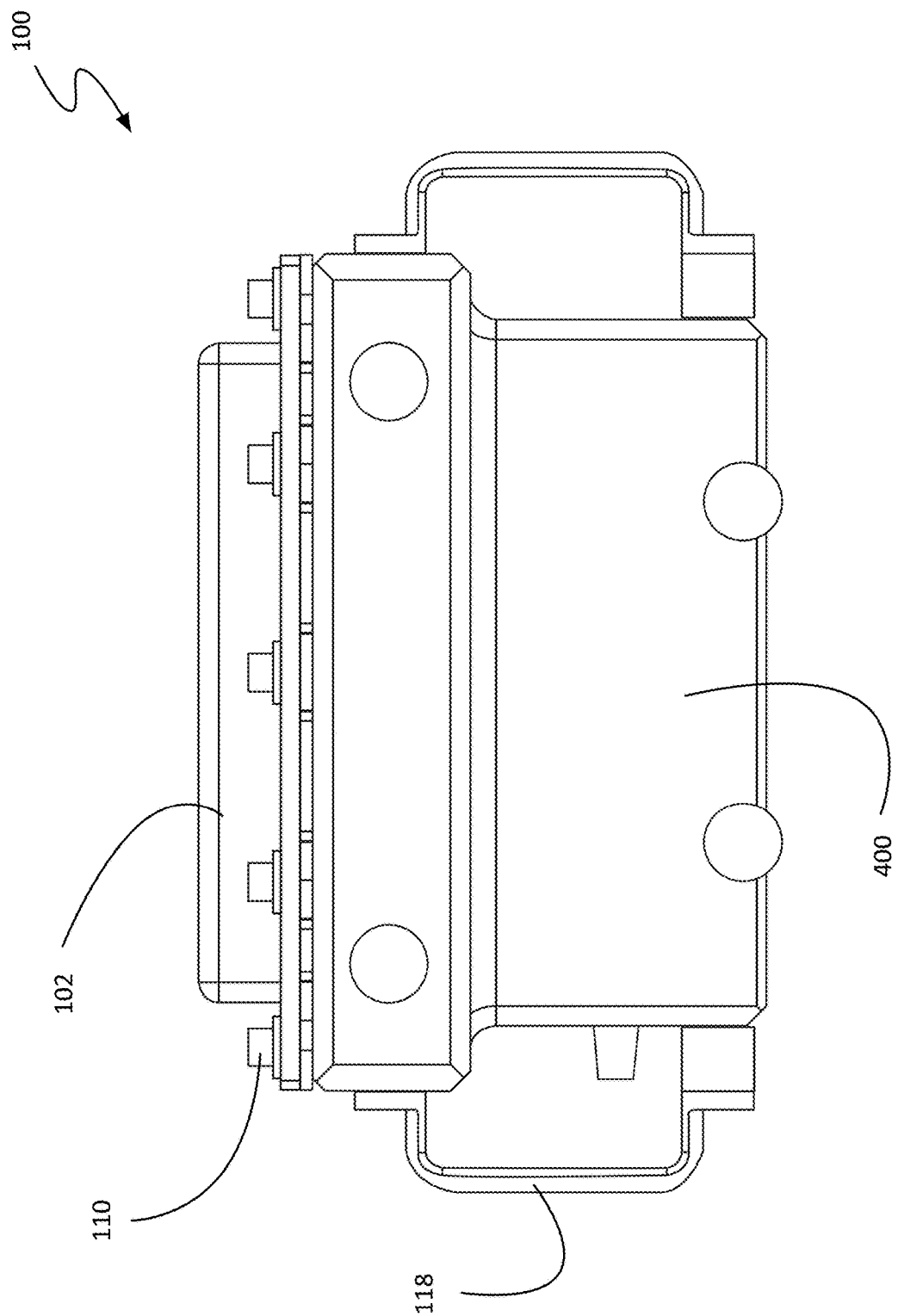

FIG. 18 is a bottom view of the pressurizing device of FIG. 15.

Figure 19:
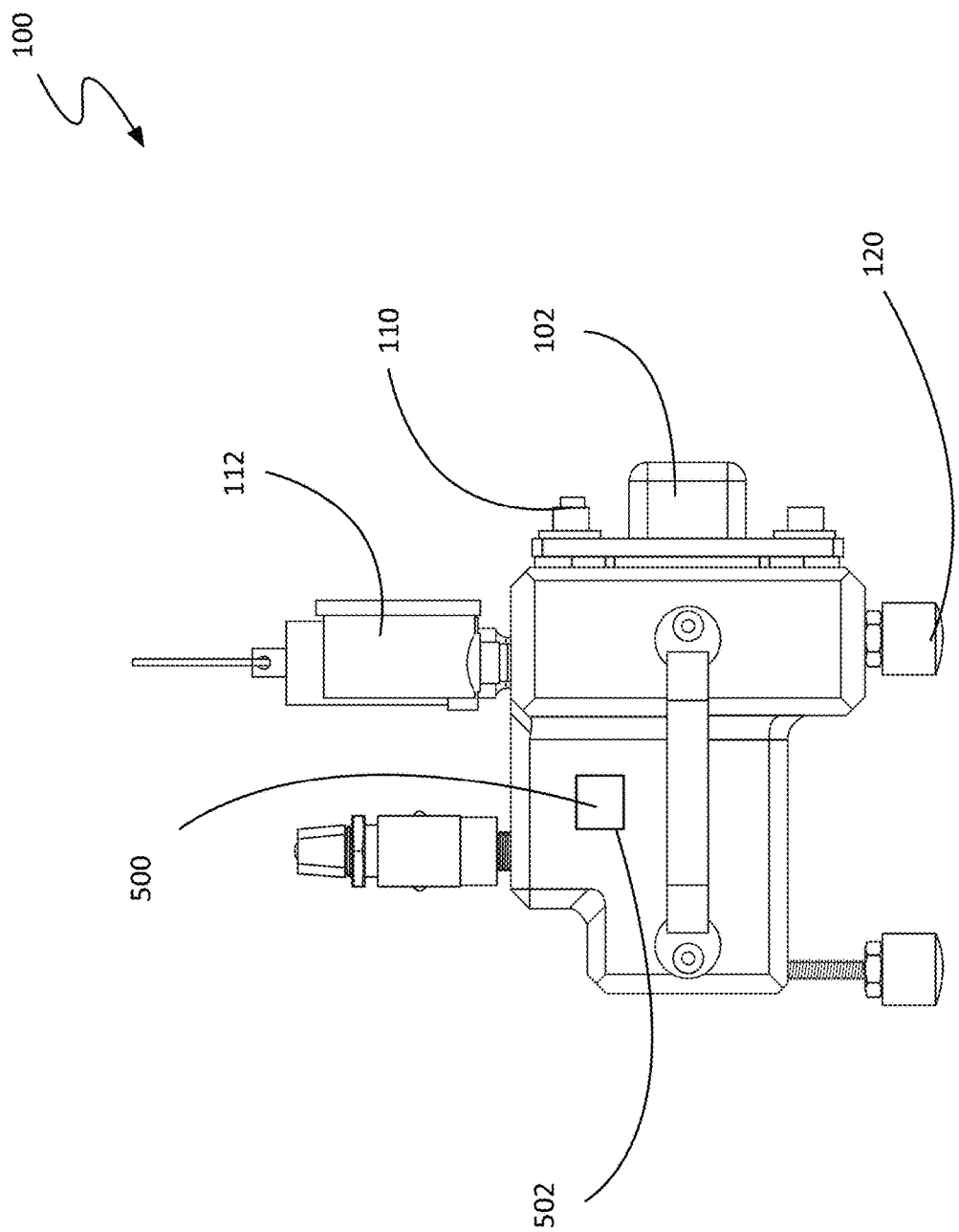

FIG. 19 is a side view of the pressurizing device of FIG. 15.

Figure 20:
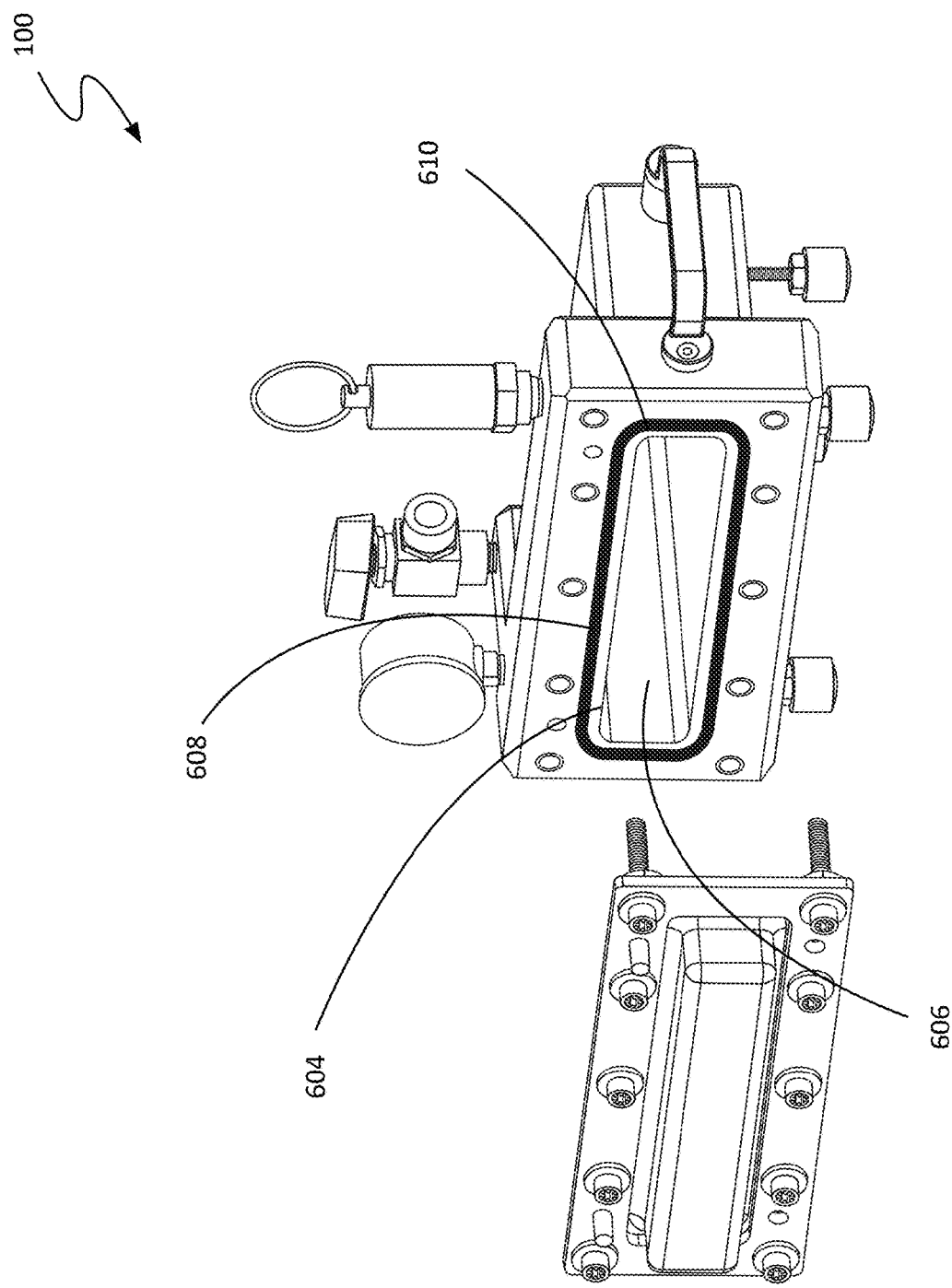

FIG. 20 is a perspective front view of the pressurizing device of FIG. 15 in an open configuration.

Figure 21:
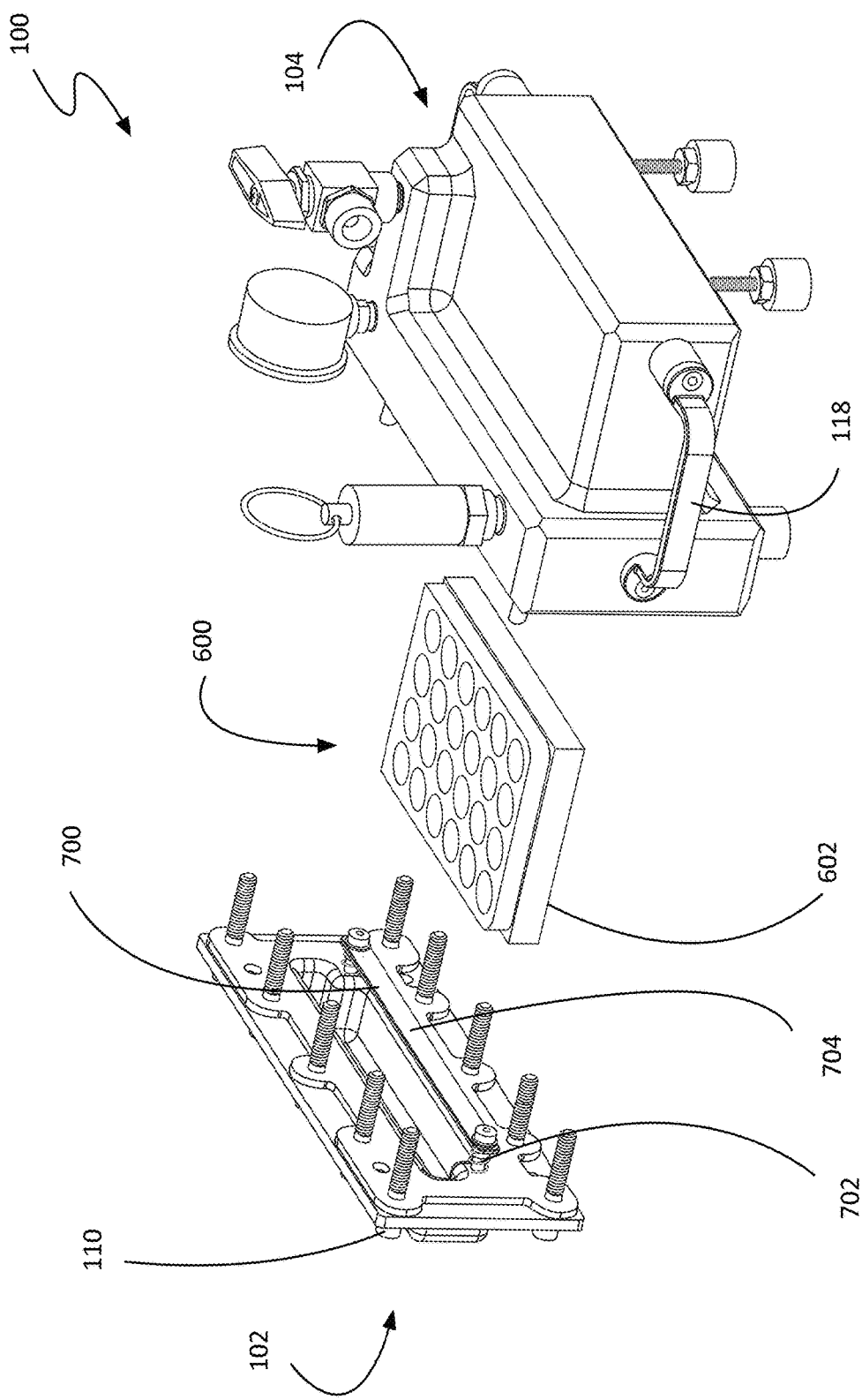

FIG. 21 is a perspective rear view of the pressurizing device of FIG. 15 in an open configuration.

Figure 22:
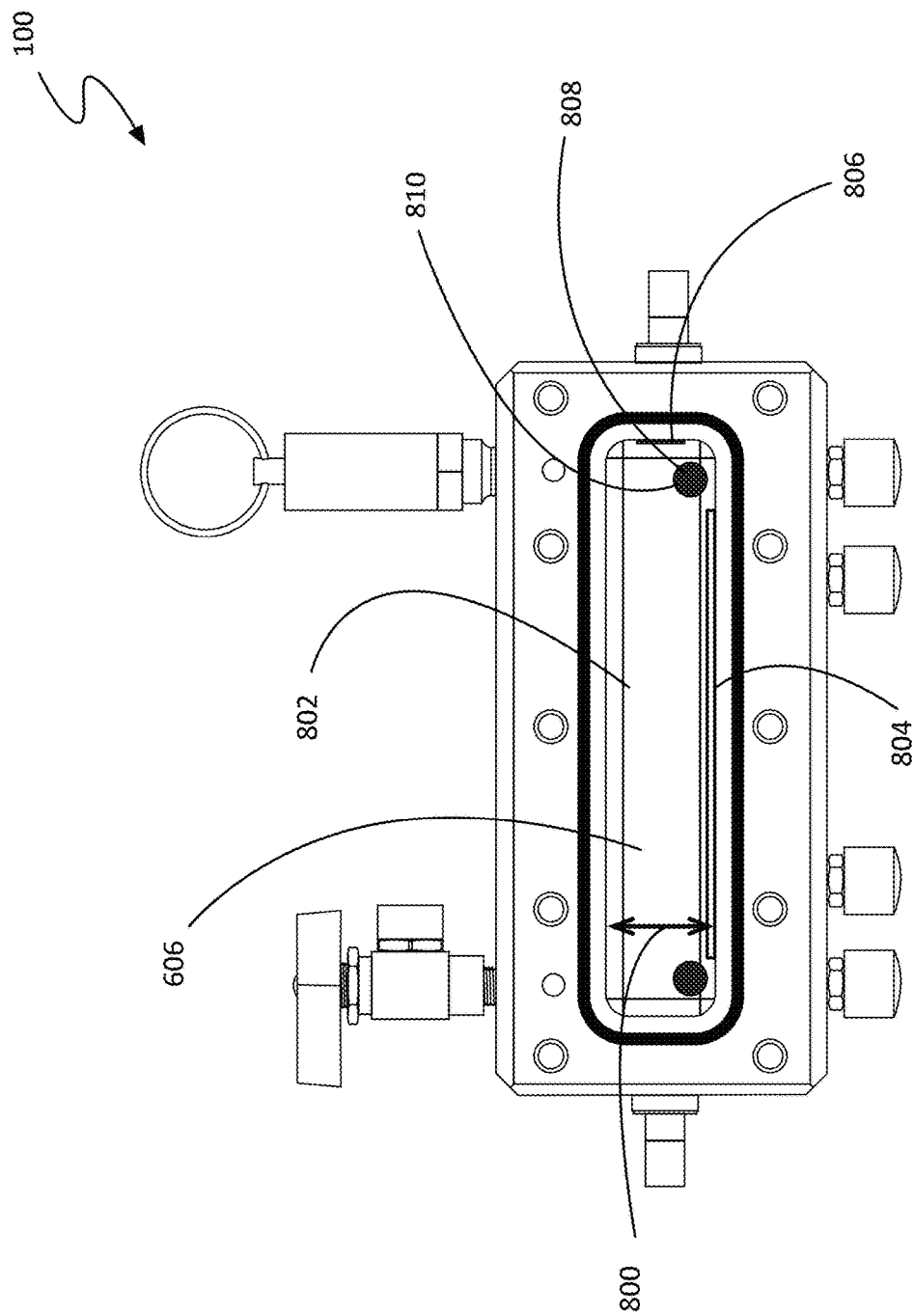

FIG. 22 is a front view of the pressurizing device of FIG. 15 in an open configuration.

Figure 23:
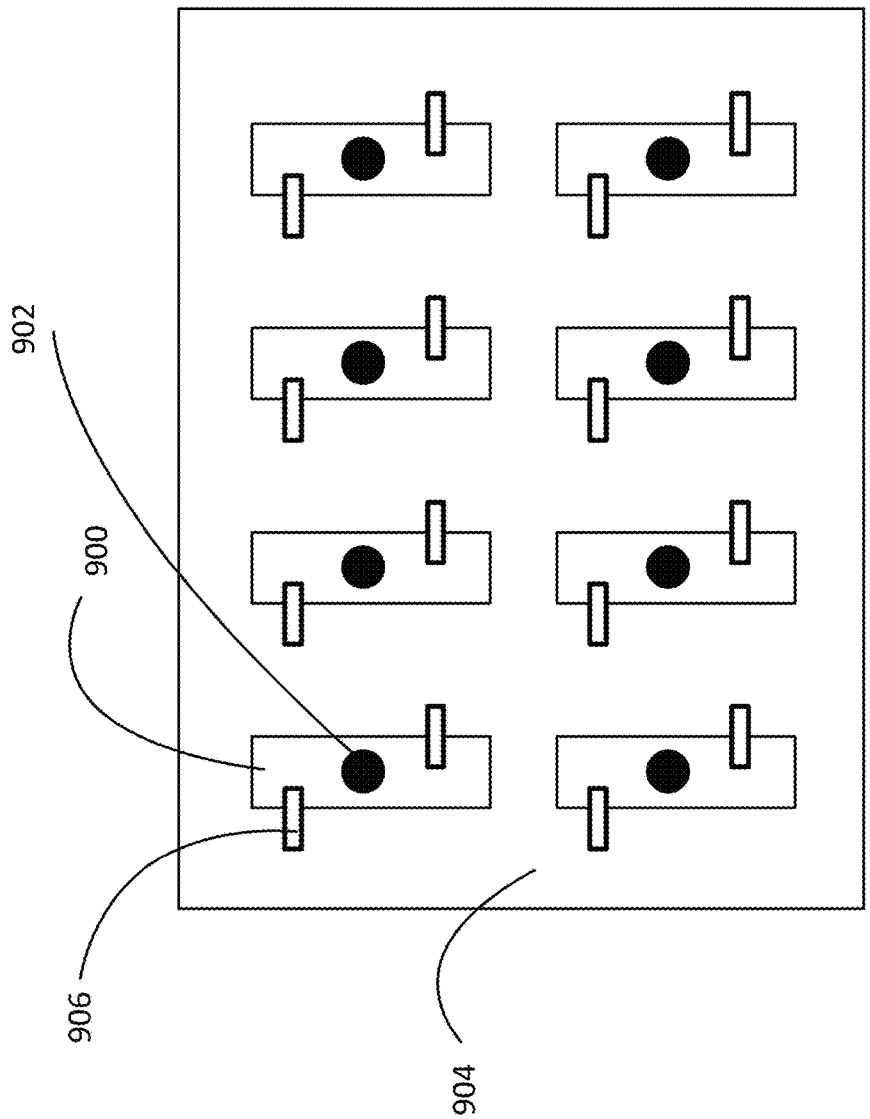

FIG. 23 is a perspective view of a retainer and a plurality of slides.

Figure 24:
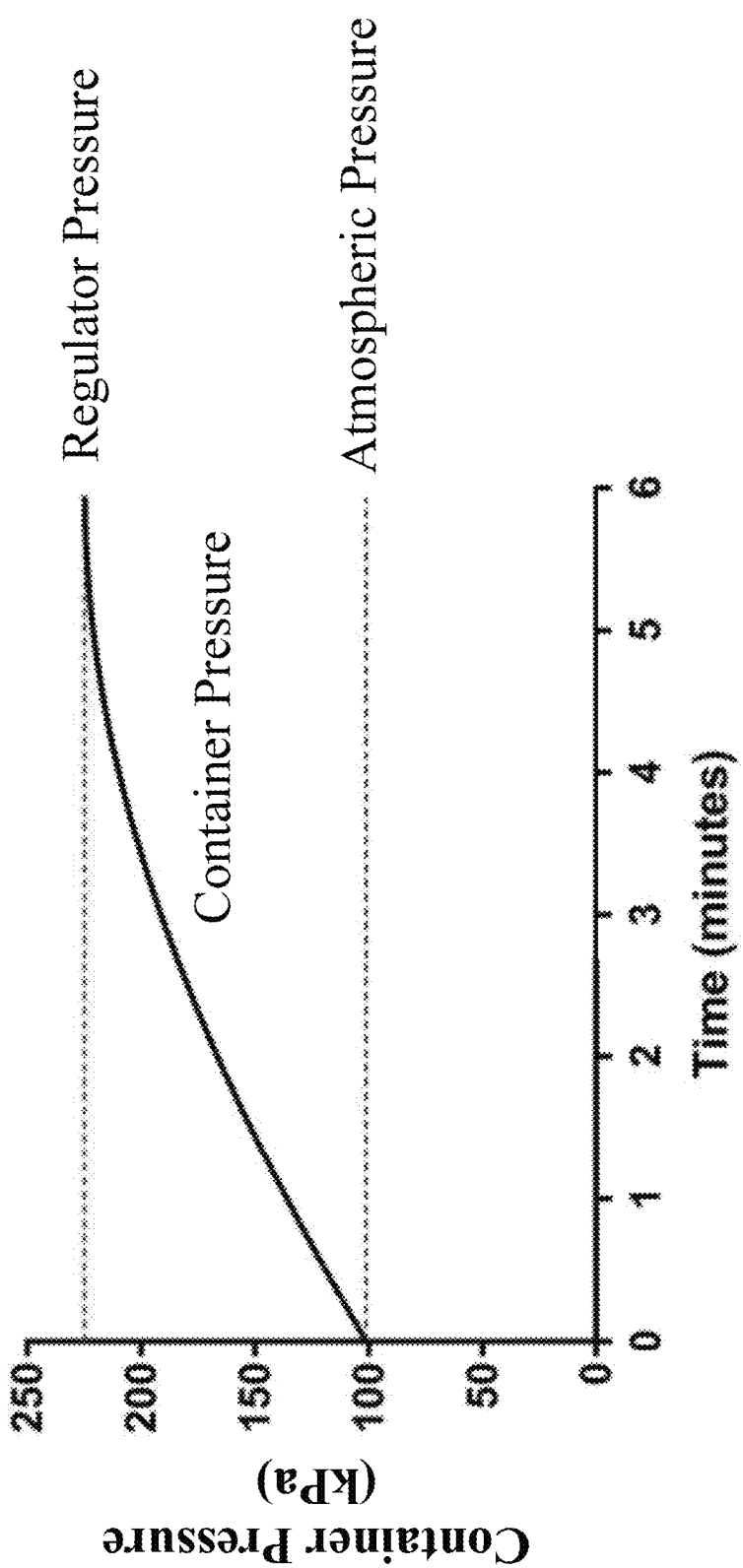

FIG. 24 depicts internal pressure as a function of time of nitrogen inflow according to an embodiment of the pressurizing device.

DETAILED DESCRIPTION (METHODS)

Sample (Tissue)

As used herein, the term "tissue" refers to an entire organism or a portion of an organism, microscopic or macroscopic, animal or non-animal. In some embodiments, the organism is an animal selected from the group consisting of: a primate (e.g., a human), a pig, a horse, a cow, a dog, a cat, a Guinean pig, a rat, a mouse, a chicken, a snake, a *Caenorhabditis elegans*, a zebrafish, a *Xenopus*, a snail, and an octopus. In other embodiments, the organism is embryonic, pre-natal, peri-natal, juvenile, post-natal, adult or post-mortem. In yet other embodiments, the organism is a non-animal, such as a plant. In some aspects, the tissue is derived from a living organism, for example, a biopsy. In other aspects, the tissue is derived from a diseased organism, for example, an autopsy or necropsy.

In some non-limiting embodiments, the tissue comprises an aggregation of morphologically or functionally similar cell types and associated intracellular and extracellular matter acting in a similar manner to perform the desired function within an organism. By way of example only, in some embodiments, the tissue includes a portion of a nervous system, e.g., a portion of a human brain. In other non-limiting aspects, the tissue comprises functional subunits of the organism's central or peripheral nervous system. In yet other non-limiting aspects, the tissue comprises a portion of the organism's white or grey matter. In further non-limiting aspects, the tissue comprises a portion of a body system selected from the group consisting of: brain, thymus, intestine, testis, lung, spleen, liver, kidney, heart, lymph node, eye, skin, limb, muscle fiber, and connective tissue.

In some embodiments the tissue comprises cultured cells grown in vitro. In some aspects, the cultured cells are a monolayer. In other aspects, the cultured cells are multilayers. In yet other aspects, the cultured cells belong to one cell type. In further aspects, the cultured cells belong to more than one cell types. Non-limiting examples of support for cell attachment include plastic support and glass support. In some embodiments, the cultured cells are an agglomerate of cells grown in floating, non-attached conditions, for example, as a neurosphere, a tumorsphere, or an organoid.

Biomolecule

In some aspects, the biomolecule is an endogenous biomolecule. In other aspects, the biomolecule is an exogenous biomolecule. Non-limiting examples of the exogenous biomolecule include an artificially implanted biomolecule, e.g., through a virus or a plasmid. Non-limiting examples of the biomolecule include a small molecule, a peptide, a protein, a carbohydrate, a glycoprotein, a lipid, a lipoprotein, a proteoglycan, and nucleic acids, etc. In some non-limiting embodiments, the biomolecule is selected from the group consisting of: a subunit of a macromolecule, a receptor, a receptor subunit, a membrane protein, an intermediate filament protein, a membrane pump, a transcription factor, and combinations thereof. In other non-limiting embodiments, the biomolecule is selected from the group consisting of: Laminin, α-SMA (α-Smooth Muscle antibody), Fibronectin, GFAP (Glial Fibrillary Acidic Protein), MAP2 (Microtubule-Associated Protein 2), Iba1 (ionized calcium-binding adapter molecule 1, also known as Allograft inflammatory factor 1 (AIF-1)), Olig2 (Oligodendrocyte transcription factor), NeuN (Neuronal Nuclei, also known as Fox-3, Rbfox3, or Hexaribonucleotide Binding Protein-3), Neurofilament, Ki67 (Antigen KI-67, also known as MKI67), Sox2 (SRY (sex determining region Y)-box 2), Vimentin, and combinations thereof. In other non-limiting embodiments, the biomolecule comprises an RNA. In yet other non-limiting embodiments, the biomolecule comprises a DNA.

In some non-limiting aspects, the biomolecule is located on a structure. In other non-limiting aspects, the biomolecule is located within a structure. Non-limiting examples of the structure include flagella, cilia, synapse, synaptic spines, extracellular matrix (ECM), cell wall, cell envelope, membrane, cytoplasm, Golgi Network, mitochondria, endoplasmic reticulum (ER) (e.g., rough ER or smooth ER), nucleus, centrioles, ribosomes, polyribosomes, lysosomes, liposomes, cytoskeletal component, vesicles, granules, peroxisome, vacuoles, protoplast, tonoplast, plasmodesmata plastid, chloroplast, pseudopodia a vascular-associated structure of the brain, dense astrocytic network of the brain, or combinations thereof.

Fixative

In some aspects, the disclosed methods include fixing the sample with a fixative. Non-limiting formulation of the fixative includes 0.1-100% of a chemical selected from the group consisting of: formalin, Paraformaldehyde (PFA), glutaraldehyde, Acetone, Methanol, Ethanol, Acetic Acid, Potassium dichromate, chromic acid, potassium permanganate, B-5, Zenker's fixative, Uranyl acetate, mercurials, osmium tetroxide, potassium permanganate, 1-ethyl-3-(3-dimethylamino propyl), Picric acid, and Picric acid derivatives. In some embodiments, the tissue is incubated in the fixative. In other embodiments, the organism from which the tissue is derived is perfused with the fixative (e.g., via intracardial perfusion or post-mortem intra-jugular perfusion). Some aspects of the methods further comprise removing PFA by washing with a conventional buffer (e.g., PBS). In some embodiments, after washing away the fixative, the tissue is further physically manipulated. For example, in some aspects, the tissue is further dissected into smaller individual pieces such as pieces of tissue that are 5×5×5 mm, 3×3×2 mm, 3×3×1 mm, or any other sizes as necessary to suit end-user needs.

Clarification

In some aspects, the first clarification step is configured to remove biomolecules from within the tissue that present difficulties for downstream applications, such as imaging. In other aspects, the first clarification step is used to remove lipids from within the tissue. Lipids are thought to be one of the most significant biomolecules that scatter light, which leads to poor image quality. In other aspects, the first clarification step comprises one or more reagents combined within a single solution (e.g., Reagent 1) that removes lipids and replaces the lipids with a polymer-based structure to provide structural support for cells within the tissue. In yet other aspects, the first clarification step is performed over a series of days (e.g., 6-7 days) at an elevated temperature (e.g., around 40° C.). In further aspects, the first clarification step is conducted under elevated pressure. Various embodiments of a pressurizing device for preparation and/or treatment of tissue are discussed in greater detail below, particularly with respect to FIGS. 15-24.

In some non-limiting aspects, the disclosed methods include a first clearing step before incubating the tissue in the staining solution under the elevated pressure. In other non-limiting aspects, the first clearing step includes a passive clearing step. Non-limiting examples of the passive clearing step include CLARITY (Clear Lipid-exchanged Acrylamide-hybridized Rigid Imaging/Immunostaining/In Situ-Hybridization-Compatible Tissue-hydrogel), PACT (the passive CLARITY technique), PARS (perfusion assisted agent release in situ), CUBIC (clear, unobstructed brain imaging cocktails and computational analysis), SeeDB (See Deep Brain), I-DISCO (immunolabeling-enabled three-dimensional imaging of solvent-cleared organs), 3-DISCO (three-dimensional imaging of solvent-cleared organs), BABB (benzyl alcohol-benzyl benzoate), Fluo-ClearBABB, FAST-CLEAR, FACT (Fast free-of-acrylamide clearing tissue), ScaleS, SWITCH (System-Wide control of Interaction Time and kinetics of Chemicals), OPTIClear (Optical Properties-adjusting Tissue-Clearing agent), Ce3D (clearing-enhanced 3D), UBASM (Urea-Based Amino-Sugar Mixture), and modifications thereof. In further non-limiting aspects, the first clearing step is PACT or modifications thereof. In yet further non-limiting aspects, the first clearing step is CUBIC or modifications thereof.

In some embodiments, the procedures provided in E. A. Susaki et al., *Advanced CUBIC Protocols for Whole-Brain and Whole-Body Clearing and Imaging,* 10 (11) Nature Protocols 1709 (2015) is employed, optionally with modification. In other embodiments, the procedures provided in one or more the following references is used with or without modification: A. Azaripour et al., *A Survey of Clearing Techniques for 3D Imaging of Tissue with Special Reference to Connective Tissue,* 51 Progress in Histochemistry and Cytochemistry 9 (2016) (discussing the following techniques, BABB, 3DISCO, CLARITY, CUBIC, PACT/PARS, iDISCO, and ACT-PRESTO), R. Tomer et al., *Advanced CLARITY for Rapid and High-Resolution Imaging of Intact Tissues,* 9(7) Nature Protocols 1682 (2014), T. Liebmann et al., *Three-Dimensional Study of Alzheimer's Disease Hallmarks using the iDISCO Clearing Method,* 16(4) Cell Rep. 1138 (2016), E. Lee et al., *ACT-PRESTO: Rapid and Consistent Tissue Clearing and Labeling Method for 3-Dimensional Imaging,* Nature Scientific Reports Jan. 11, 2016, A. Erturk et al., *Imaging Cleared Intact Biological Systems at a Cellular Level by 3DISCO,* 89 J. Visualized Experiments e51382 (2014), M Stefaniuk et al., *Light-Sheet Microscopy Imaging of a Whole Cleared Rate Brain with Thy1-GFP Transgene,* Nature Scientific Reports Jun. 17, 2016, and T Yu et al., *Elevated-Temperature-Induced Acceleration of PACT Clearing Process of Mouse Brain Tissue,* Nature Scientific Reports Jan. 31, 2017. These references are hereby incorporated in their entirety for all purposes.

In some non-limiting embodiments, the disclosed methods include a second clearing step. In other embodiments, the second clearing step occurs before staining. In yet other embodiments, the second clearing step occurs after staining. In some aspects, the second clearing step aids in matching the refractive index between the tissue and a second collection of reagents provided in a single composition (e.g., Reagent 2). In other aspects, the second clearing step reduces light scattering during downstream imaging applications. In yet other aspects, the second clearing step comprises incubating the tissue with Reagent 2 in one or more repeated applications. In further aspects, the second clearing step is performed over a series of days (e.g., 2-3 days), at an elevated temperature (e.g., around 37-40° C.). In yet further aspects, the second clearing step is conducted under elevated pressure.

Some embodiments comprise a washing step after completion of the first clearing step. In other embodiments, the tissue is washed, e.g., using a conventional buffer with a preservative (e.g., sodium azide) before staining.

Retrieval of the Biomolecule

In some non-limiting aspects, the disclosed methods include incubating the tissue in a Citrate Buffer at about 95° C. (e.g., 80°–120° C., 90-100° C., 93-97° C. or 94-96° C.) for about 30 minutes (e.g., 20-40 minutes, 25-35 minutes, or 28-32 minutes) to retrieve the biomolecule. In some non-limiting embodiments, the pH of the Citrate Buffer is about pH6 (e.g., pH5.5-6.5, pH5.7-6.3 or pH5.9-6.1). In other embodiments, the antigen retrieval step occurs before the first clearing step, before the second clearing step, and/or before staining. In some aspects, the antigen retrieval step breaks apart larger protein complexes to expose the biomolecule (e.g., an epitope). Other conventional processing steps commonly used in the art of tissue processing, staining, and imaging may also be added to the aforementioned inventive methodology to suit end-user needs.

Staining

Some embodiments of the method comprise permeabilizing the tissue before staining using a permeabilization buffer. In other embodiments, the permeabilization buffer is a buffer with a detergent. In yet other embodiments, the permeabilization buffer is selected from the group consisting of TWEEN® and Triton-X. In some aspects, the permeabilization step is repeated several times.

As used herein, the term "staining" refers to any technique and reagent that is now known or discovered in the future that can provide a signal-based indication of the presence or absence of a particular target moiety within the tissue. In some embodiments, the disclosed methods improve staining capabilities, e.g., quality.

Non-limiting examples of the staining agent include a small molecule, dye, an antibody, an enzyme, a viral particle, nanoparticles, a nucleic acid probe, or combinations thereof. In some non-limiting embodiments, the staining agent comprises a label, for example, a chromogenic label, a fluorescent label, a radionuclide-conjugated label, or combinations thereof.

In some non-limiting embodiments, the staining agent comprises a small molecule that is capable of binding to a particular target moiety within the tissue. Examples of the small molecule include DAPI, propidium iodide, lectin, fluorescent nissl (i.e., NeuroTrace), phalloidin, HOECHST, and any other small molecule that can bind to a target moiety within the tissue. In some aspects, the small molecule naturally produces a signal, e.g., fluorescence (e.g., DAPI or propidium iodide). In other aspects, the small molecule is conjugated to an indicator to produce a signal, e.g., fluorescence (e.g., lectin, fluorescent nissl, or phalloidin). In yet other aspects, the conjugated small molecule is conjugated to a non-fluorescent signal producing indicator, e.g., a colorimetric indicator (e.g., horseradish peroxidase (HRP) or 3,3'-diaminobenzidine tetrahydrochloride (DAB)).

Non-limiting examples of flurophores that can be attached to primary and/or secondary antibody include: Alexa Fluor 350, Alexa Fluor 405, Alexa Fluor 488, Alexa Fluor 532, Alexa Fluor 546, Alexa Fluor 555, Alexa Fluor 568, Alexa Fluor 594, Alexa Fluor 647, Alexa Fluor 680, Alexa Fluor 750, BODIPY FL, Coumarin, Cy3, Cy5, Fluorescein (FITC), Oregon Green, Pacific Blue, Pacific Green, Pacific Orange, Tetramethylrhodamine (TRITC), Texas Red, APC-eFluor 780, eFluor 450, eFluor 506, eFluor 660, PE-eFluor 610, PerCP-eFluor 710, Super Bright 436, Super Bright 645, Super Bright 702, Super Bright 780, Super Bright 600, Qdot 525, Qdot 565, Qdot 605, Qdot 655, Qdot 705, Qdot 800, R-phycoerythrin (R-PE), and Allophycocyanin (APC). Non-limitng examples of dyes that recognizes DNA include: DAPI, SYTOX Green, SYTO 9, TO-PRO-3, and Propidium Iodide.

In some embodiments, the staining agent comprises an antibody. In some aspects, the antibody is a primary antibody that comprises a label that directly or indirectly produces a signal. For example, a biotin label, a fluorescent label, an enzyme label (e.g., HRP or DAB), a coenzyme label, a chemiluminescent label, or a radioactive isotope label. In other aspects, the primary antibody is applied as the single stain (e.g., with or without additional reagents, such as labeled streptavidin or enzyme/coenzyme substrate to provide a signal).

Some aspects of the disclosed methods comprise washing the tissue with permeabilization buffer. Other aspects further comprise a second staining step. In some embodiments, the second staining solution comprises a secondary antibody. In other embodiments, the secondary antibody is polyclonal and generated against the primary antibody such that the secondary antibody solution recognizes multiple epitopes associated with the primary antibody. As such, the primary antibody binds to multiple secondary antibodies, which produces an amplified signal. In yet other embodiments, the secondary antibody comprises a label that directly or indirectly produces a signal. For example, a biotin label, a fluorescent label, an enzyme label (e.g., HRP), a coenzyme label, a chemiluminescent label, or a radioactive isotope label. In other embodiments, the secondary antibody comprises a fluorescent label detectable by a conventional confocal microscope or any other type of imaging system.

In some embodiments, the secondary antibody is bound to a molecule, e.g., biotin and the method include adding streptavidin, which binds to the biotin. In some aspects, the streptavidin comprises one or more of the aforementioned labels (e.g., a fluorescent label, an enzyme label (e.g., HRP or DAB), a coenzyme label, a chemiluminescent label, a radioactive isotope label, etc.). As such, the signal is further amplified.

In addition, other signal-generating techniques can be used as stains. In some aspects, tyramide-based signal amplification is used. In short, a stain, such as a small-molecule-based stain or an immunoaffinity-based stain is used and coupled with an HRP-labeled antibody that recognizes the stain (e.g., a primary antibody) or a streptavidin conjugate comprising HRP. Tyramide-conjugated molecules are added such that the HRP produces highly reactive, short-lived tyramide radicals that covalently couple to residues in the vicinity of the HRP-target moiety site. In further embodiments, the tyramide comprises a fluorescent label, and the label further enhances the signal related to the original stain.

In some embodiments, staining comprises modified nucleic acids strand-targeted detection activities. In other embodiments, staining comprises in situ hybridization such that the stain comprises a nucleotide-based probe capable of hybridizing to a predetermined sequence of nucleic acids within the tissue. In yet other aspects, the nucleotide-based probe comprises a label (e.g., one or more of the labels provided above) to enable signal production and detection of the nucleotide-based probe. In further embodiments, the nucleotide-based probe comprises a fluorescent label (FISH). In yet further embodiments, staining comprises click-chemistry labeling methods, e.g., the use of IdU, EdU, and/or BrdU.

In some embodiments, the tissue provides an endogenous signal, e.g., an endogenously fluorescent molecule. Examples of the endogenously fluorescent molecule include a fluorescent protein reporter (e.g., green fluorescent (GFP), red fluorescent protein (RFP)). In other embodiments, the organism is transgenic, and the fluorescent molecules are expressed, driven by, e.g., a constitutive or an inducible promoter. In yet other aspects, the organism is infected with a recombinant virus or transfected with a plasmid encoding the fluorescent protein.

Non-limiting examples of the fluorescent protein reporters include: green fluorescent (GFP), EGFP (enhanced GFP), BFP (Blue fluorescent protein), CFP (cyan), red fluorescent protein (RFP), wtGFP (White GFP), YFP (yellow fluorescent protein), dsRed, mCherry, mVenus, mCitrine, TdTomato, Luciferase, etc.

In some aspects, after incubation with the secondary antibody, the tissue is washed with either additional permeabilization buffer or other buffers.

For the avoidance of doubt, although detailed above using an exemplary discussion regarding the use of primary and secondary antibodies, any of the staining techniques discussed herein can be employed. For example, a primary antibody comprising a label (e.g., a fluorescent or another label) can be employed such that a secondary antibody is not necessary. Or, a small-molecule stain can be used such that no antibodies are necessary. Moreover, a secondary antibody comprising a biotin label can be used such that a third incubation with labeled streptavidin (e.g., streptavidin comprising a fluorescent label) can be used as well. Any of the aforementioned staining procedures can be used, as can any other staining procedures known to those of skill in the art.

In some aspects, the tissue or organism is processed for an immunohistochemistry application, an immunofluorescence application, a fluorescence application, and/or a colorimetric application. In further aspects, the tissue or organism is processed for a microscopy-based application. Examples of the microscopy-based application include immunofluorescence, electron microscopy, confocal microscopy, two-photon microscopy, super-resolution microscopy, light-sheet microscopy, etc. Examples of electron microscopy include scanning electron microscopy and transmission electron microscopy.

Elevated Pressure

The samples are incubated in the staining solution under elevated pressure. In some embodiments, the elevated pressure is between 1.2-200 ATM, or any number range in between, e.g., 1.2-200 ATM, 1.2-150 ATM, 1.3-150 ATM, 1.3-100 ATM, 1.4-100 ATM, 1.4-50 ATM, 1.5-50 ATM, or 2-30 ATM, etc. In other non-limiting embodiments, the elevated pressure is between 1.5-30 ATM, or any number range in between, e.g., 1.6-30 ATM, 1.6-20 ATM, 1.7-20 ATM, 1.7-15 ATM, 1.8-15 ATM, 1.8-10 ATM, 1.9-10 ATM, 1.9-5 ATM, 2-5 ATM, 2-10 ATM, 2-15 ATM, 2-20 ATM, 2-25 ATM, or 2-30 ATM, etc. In yet other non-limiting embodiments, the elevated pressure is at least 1.5 ATM, at least 2.5 ATM, at least 3 ATM, at least 6.5 ATM, at least 10 ATM, at least 15 ATM, or at least 30 ATM, etc.

In some non-limiting aspects, the elevated pressured is maintained at a relatively constant level. For example, the maximum value of the elevated pressure is equal to or less than 250%, 200%, 190%, 180%, 170%, 160%, 150%, 140%, 130%, 120% or 110% of the minimum value of the elevated pressure. In other non-limiting aspects, the elevated pressured is actively maintained. In yet other non-limiting aspects, the maintained pressure is multidirectional. In further non-limiting aspects, the maintained pressure is homogeneous.

In some aspects, the elevated pressure (pressurization) accelerates and/or increases penetration of a molecule. In further aspects, the molecule having a Molecular Weight of between 1 g/mol and 1,000,000 g/mol, or any number range in between, e.g. 10-1,000,000 g/mol, 10-750,000 g/mol, 50-750,000 g/mol, 50-500,000 g/mol, 150-500,000 g/mol, 150-300,000 g/mol, 200-300,000 g/mol, 200-150,000 g/mol, or 250-150,000 g/mol, etc.

Various embodiments of a pressurization device configured to implement various tissue treatment methodologies, including those contemplated herein, are discussed below in the context of FIGS. 15-23.

Temperature

In some embodiments, the temperature of the staining solution is between about 2° C. and about 60° C. or any temperature in between, e.g., 2-37° C., 4-37° C., 4-30° C., 4-25° C., 4-20° C., etc. In some non-limiting aspects, the temperature is maintained at a relatively constant level. For example, the highest temperature is not more than 1° C., 2° C., 3° C., 4° C., 5° C., 6° C., 7° C., 8° C., 9° C., or 10° C. higher than the lowest temperature. In other non-limiting aspects, the temperature is actively maintained.

The Thickness of the Tissue

Sample Requires Clearing

In some aspects, the sample is relatively thick and requires clearing. In some non-limiting embodiments, the thickness of the tissue is at least 500 μm, at least 1 mm, at least 2 mm, at least 5 mm, or at least 7 mm, etc. In certain non-limiting embodiments, the thickness of the thickness of the tissue is between 1-30,000 μm, or any number range in between, e.g., 1-20,000 μm, 2-20,000 μm, 2-15,000 μm, 5-15,000 μm, 5-10,000 μm, 15-10,000 μm, 15-7,500 μm, 30-7,500 μm, 30-5,500 μm, 45-5,500 μm or about 5,000 μm, etc. In other non-limiting embodiments, the thickness of the tissue is 100-30,000 μm, or any number range in between, e.g., 1,000-7,000 μm, 150-30,000 μm, 150-20,000 μm, 250-30,000 μm, 250-20,000 μm, 250-10,000 μm, 400-10,000 μm, 400-6,000 μm, 600-6,000 μm, 600-4,000 μm, 1,000-4,000 μm, 1,000-2,500 μm, 1,500-2,500 μm or about 2,000 μm, etc.

Sample does not Require Clearing

In some aspects, the sample does not require clearing. In certain non-limiting embodiments, the thickness of the thickness of the tissue is between 1-30,000 μm, or any number range in between, e.g., 1-20,000 μm, 2-20,000 μm, 2-15,000 μm, 5-15,000 μm, 5-10,000 μm, 15-10,000 μm, 15-7,500 μm, 30-7,500 μm, 30-5,500 μm, 45-5,500 μm or about 5,000 μm, etc. In other aspects, the sample is relatively thin and does not require clearing. In certain non-limiting embodiments, the thickness of the tissue is between 1-200 μm, or any number range in between, e.g., 1-100 μm, 2-200 μm, 2-150 μm, 5-150 μm, 5-100 μm, 15-100 μm, 15-75 μm, 30-75 μm, 30-55 μm, 45-55 μm or about 50 μm, etc.

Time of Sample Under Pressure

Sample Requires Clearing

In some non-limiting embodiments, the length of time the sample is incubated under elevated pressure is between (about) 2 hrs and (about) 7 days, or any number range in between, e.g., 6 hrs to 7 days, 6 hrs to 6 days, 18 hrs to 6 days, 18 hrs to 5 days, 2-5 days, 2-4.5 days, 2.5-4.5 days, 2.5-4 days, 2-4 days, 2-3.5 days, 2.5-3.5 days, or about 3 days, etc.

Sample does not Require Clearing

In some non-limiting aspects, the length of time the sample is incubated under elevated pressure is between 1 minute and 24 hours or any length range in between, e.g., 1 minute and 2.5 hours, 2 minutes to 24 hours, 2 minutes to 18 hours, 5 minutes to 18 hours, 5 minutes to 12 hours, 10 minutes to 12 hours, 10 minutes to 8 hours, or 20 minutes to 8 hours, etc.

In general, the thicker the section, the longer the length of time the sample is incubated under elevated pressure. For example, in some non-limiting embodiments, a 1-10 µm sample is incubated for 1-30 minutes, or any length range in between, e.g., 1-25 minutes, 2-25 minutes, 2-20 minutes, 4-20 minutes, 4-16 minutes, 6-16 minutes, 6-13 minutes, 9-13 minutes, 9-11 minutes, or about 10 minutes, etc. In other non-limiting embodiments, a 30-50 µm sample is incubated for 10 minutes to 12 hrs, or any length range in between, e.g., 10 minutes to 10 hrs, 15 minutes to 10 hrs, 15 minutes to 7 hrs, 30 minutes to 7 hrs, 30 minutes to 5 hrs, 1-5 hrs, 1-4 hrs, 1-3 hrs, 1.5-3 hrs, or 1.5-2 hrs, etc. In yet other non-limiting embodiments, an about 100 µm sample (e.g., 80-120 µm) is incubated for 3-14 hours, or any length range in between, e.g., 3-13 hours, 4-13 hours, 4-12 hours, 5-12 hours, 5-11 hours, 6-11 hours, 6-10 hours, 7-10 hours, 7-9 hours, or about 8 hours, etc.

Some embodiments of the methods comprise normalizing the refractive index of the tissue, e.g., incubating the tissue in a refractive index matching solution (RIMS solution). In some aspects, the normalizing step reduces light scattering during downstream imaging applications. In other aspects, the normalizing step has a predetermined duration (e.g., around 6 hrs). In yet other aspects, the normalizing step is conducted under elevated pressure. In further aspects, the normalizing step uses the BABB method (as described in M Schwarz et al., *Fluorescent-Protein Stabilization and High Resolution Imaging of Cleared, Intact Mouse Brains*, 10(5) PLoS ONE e0124650 (2015)).

Slides

Some aspects of the methods comprise mounting the tissue on a rigid support. In some embodiments, mounting is permanent. In other embodiments, mounting is temporary. In some embodiments, mounting is performed before applying the treatment. In other embodiments, mounting is performed during the treatment. In yet other embodiments, mounting is performed following to the treatment. In some embodiments, the support is of a conventional microscope slide (e.g., a glass slide of dimensions 25×75 mm). In some embodiments, the slide is untreated. In other embodiments, the slide is gelatin-treated. In yet other embodiments, the slide is electrostatically-charged. In further embodiments, the slide is disk-shaped as detailed in the aforementioned references. Further embodiments comprise applying a hydrophobic barrier, a tissue isolator, or a coverslip thereto. In some aspects, the thickness of the tissue isolator is 0.1-2.5 mm. In other aspects, the tissue isolator is silicon-based. Yet further embodiments comprise storing the slide, imaging the slide, or both.

EXAMPLES

The following description includes details regarding exemplary applications of the tissue treatment system and applicable methodologies. The following description is only for the purposes of one or more examples of the system and applicable methodologies. Nothing contained herein is to be construed as limiting the scope and breadth of this technology.

Example 1. Material and Methods

Human Tissue Procurement

Human tissue was de-identified and collected with informed consent in accordance with the St. Joseph's Hospital and Medical Center Internal Review Board (IRB). Tissue from six Glioma cases was used for our experiments (Table 1).

TABLE 1

Human Samples Used

| ID | Age | Sex | PMI (hrs) | Cause of death |
|---|---|---|---|---|
| 0907 | 70 | F | 12 | GBM |
| 0209 | 64 | M | 14 | GBM |
| 1908 | 27 | M | 7 | GBM |
| 0611 | 20 | F | 13 | GBM |
| 1108 | 82 | M | 6 | GBM |
| 0926 | 73 | F | 4 | GBM |

PMI: Post-mortem interval.
GBM: Glioblastoma

Upon collection, the brains were cut into 2 cm coronal slabs and submerged in 4% paraformaldehyde (PFA) for 100 hrs at 4° C. Tissues were dissected and preserved at 4° C. in Phosphate Buffer Saline (PBS) 0.01% $NaN_3$ for less than 2 years. Anatomically adjacent samples were used in comparative experiments to minimize variability. Unless specified, samples were obtained from tumor-free brain areas (e.g., Cerebellum, Cortex or Caudate Nucleus) as ascertained by available imaging and gross inspection.

A timely dissection is critical to ensure the best use of this tissue of paramount importance in research. We have found that 2-cm thick fresh brain slabs reach optimal fixation after being submerged for 100 hrs in 4% PFA, as the speed of fixative penetration from both sides is 0.1 mm/hr[21]. While human brain perfusion with fixatives[22,23] is an extremely complex technique to implement in a lab, currently the most common method for fixation is incubation in a formalin bath. However, prolonged incubation leads to over-fixation, making the tissue sub-optimal for IHC.

Cell Culture

Patient-derived cell line GB3 was established from resected primary GBM tumor tissue at BNI. Briefly, tumor tissue was processed using the Gentle MACS Dissociator and Tumor Tissue Dissociation kit (Miltenyi Biotec Inc.). Cells were expanded as neurospheres in tissue culture dishes coated with poly-(2-hydroxyethyl methacrylate) (Sigma-Aldrich) or grown adherent on laminin (Fisher Science), in neural stem cell (NSC) medium consisting of DMEM and F12-Glutamax supplemented with B27 and N2 (Fisher Science), in the presence of 20 ng/ml EGF and 20 ng/ml FGF2 (EMD Millipore). To generate GB3-RFP cell line, GB3 cells were transduced with pre-made lentiviral particles (Amsbio) expressing RFP-Luc (GB3-RFP) and were selected using blasticidin (2 µg/ml).

Mouse GBM Xenografts

Animal husbandry was performed according to the guidelines of St. Joseph Hospital and Medical Center and Barrow Neurological Institute under the Institutional Animal Care and Use Committee—approved protocol. Five- to six-week-old IcrTac:ICR-Prkdcscid mice were used for in vivo orthotopic transplant of fluorescently-tagged GB3-RFP cells. For orthotopic transplants, 2 μL of dissociated cells at a density of 100,000 cells/μL were injected into the right hemisphere (stereotactic coordinates AP 0, ML-2, DV-2.5), as described[24]. Four weeks after injection, tumor-bearing mice were euthanized with a lethal intraperitoneal injection of 2.5% Avertin (2,2,2-Tribromoethanol, Sigma-Aldrich, T48402; tert-Amyl alcohol, Sigma-Aldrich, A1685). Tissues were fixed through intracardial perfusion with Ringer's solution (Electron Microscopy Sciences, 11763-10) supplemented with 40 mM $NaNO_2$, 2 mM $NaCHO_3$, and 50 I U/mL heparin, followed by ice-cold 4% PFA in 0.1M phosphate buffer (PB). Brains were subsequently cryoprotected with incubation in PB/30% sucrose for 48 hours before being cut into 1 mm coronal sections using a vibratome (Microm HM550, Thermo Scientific).

PACT Clearing

PACT clearing procedure was applied as described by Tomer et al.[25] with temperature modifications[26].

Solutions

Hydrogel solution was prepared by mixing 40 ml of 40% Acrylamide (Bio-Rad, 161-040), 1 g of 0.25% VA-044 Initiator (Wako, 27776-21-2) in 360 ml of PBS. Clearing Solution was prepared by mixing 400 ml of 20% SDS (Thermo Fisher, 28365) and 200 ml of 1M Boric Acid (Sigma-Aldrich, B7901) in 400 ml of $dH_2O$.

Hydrogel Infusion and Washing

The tissue sample was completely submerged in hydrogel solution in a 15 ml tube (Falcon) for 1-4 days at 4° C. with gentle shaking and addition of fresh hydrogel solution every two days. Then, each tube was degassed on ice for 10 minutes using a house vacuum to remove all $O_2$, followed by an inlet of $N_2$ for 5 minutes. After 4 hours at room temperature (RT), the tissue was transferred from the tube to the 12-well plate fitting the Pressure box. Tissue was incubated in clearing solution at 40° C. under continuous rocking, replacing the solution every 2 days. Upon completion of the clearing, the tissue was washed with boric acid buffer 0.2M/0.1% TX at pH 8.5 for two days. After the washes were completed, the tissue proceeded with the IHC protocol.

CUBIC Clearing

The CUBIC method was applied with minor modifications[26] of the original protocol[18].

Solutions

Reagent 1 (R1) was prepared by adding 30 g of urea (Sigma-Aldrich U0631), 30 ml of Quadrol (Sigma-Aldrich 122262), and 17 ml of Triton X-100 (Sigma-Aldrich T8532) to 42 ml of $dH_2O$. R1 was diluted 1:1 with water to generate water-diluted Reagent 1 (WDR1). Reagent 2 (R2) was prepared by adding 31.6 g of urea, 52.4 g of sucrose (Sigma-Aldrich S0389), and 15 ml of triethanolamine (Sigma-Aldrich 90279) to 25 ml of $dH_2O$. R2 was diluted 1:1 with 0.1M PB to form PB-diluted Reagent 2 (PDR2).

Reagent 1

Every step of the procedure was performed in the 12-well plate with continuous rocking. After a wash in PB/0.01% $NaN_3$ for 2 hrs at room temperature (RT), the tissue was incubated in WDR1 at 40° C. for 5 hrs, followed by washes in R1 for 6 days at RT (R1 was replaced every two days). On day 7, the sample was washed in PB/0.01% $NaN_3$ for 2 hrs at RT before the commencement of the IHC.

Reagent 2

At the end of the IHC staining, the tissue was incubated with PDR2 for 6 hours at RT, followed by incubation with R2 for 12 hrs at 40° C. These last two steps were repeated once before mounting.

IHC, pIHC & Stainings

Figure 1A:
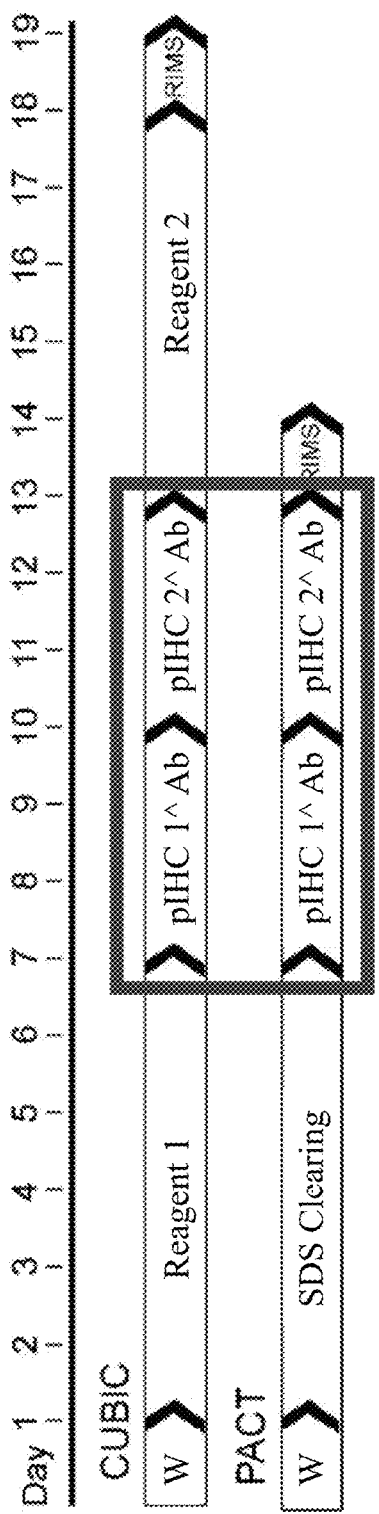
FIGS. 1A-1B The timelines of non-limiting embodiments of the tissue-treatment methods.

The timing of immunostaining and clearing are depicted in FIG. 1A. Samples were repeatedly washed with PB/0.1% Triton-X (PBTX) before incubation with the primary antibodies for 72 hrs at 4° C. in PBTX/2% goat serum. Antibodies used in the study are listed in Table 2. Following repeated washes in PBTX, samples were incubated with the species-matching Alexa-conjugated secondary antibodies (1:200; Life Science) and DAPI (10 μg/ml) in PBTX/2% goat serum for 72 hrs at 4° C. In some experiments, the diffusion dye Tomato-Lectin (Vector Lab; 1:250) was added with the secondary antibodies. Negative controls were subjected to the same procedure (two 72-hr pressurizations) without adding primary antibody.

Care was taken in selecting the experimental parameters for both thick human and mouse samples. Standardized incubation times of 72 hrs were chosen to ensure enough time for penetration and comparability with other studies[9]. Clarification strongly permeabilizes the tissue[18], hence a low detergent concentration was used in pIHC. An indirect IHC protocol was used to ensure a strong signal through amplification. Based on the calculation, the changes in temperature would result in negligible changes of pressure. Low temperatures were chosen to favor antibody binding specificity, although temperatures in the range of 20-37° C. can increase the depth of antibody binding[25] and are the standard in cleared tissue stainings[5,11,14,16,27-31]. As a rule of thumb, thick tissue required antibodies to be 10-fold more concentrated than on thin sections (Table 2), increasing the cost considerably. pIHC ensures that most of the antibodies are used effectively.

TABLE 2

Antibodies and Dyes Used

| Species | Antigen | Company | Cat. Nr. | Dilution (40 μm) | Dilution (1 mm) | Laser Power (top 400 μm) |
|---|---|---|---|---|---|---|
| Chicken | Vimentin | Millipore | AB5733 ab26245 | 1:1000 | 1:200 | 60% |
| Mouse | Fibronectin | Abcam | discontinued | 1:200 | 1:50 | 30% |
| Rabbit | Laminin | Abcam | ab11575 | 1:200 | 1:50 | 30% |
| Guinea Pig | MAP2 | Synaptic Systems | 188004 | 1:1000 | 1:100 | 50% |
| Rabbit | Iba1 | Wako | 019-19741 | 1:400 | 1:100 | 30% |
| Mouse | GFAP | Millipore | MAB360 | 1:500 | 1:50 | 20% |
| Mouse | a-SMA | Abcam | ab7817 | — | 1:50 | 20% |
| Mouse | Olig2 | Millipore | AB9610 | 1:200 | — | n.a. |
| Mouse | Neurofilament | Abcam | ab7794 | 1:200 | — | n.a. |
| Mouse | NeuN | Millipore Cell | MAB377 | 1:200 | — | n.a. |
| Rabbit | SOX2 | Signaling | 3579S | 1:200 | 1:50 | 30% |
| Mouse | Ki-67 | DAKO | M7240 | 1:150 | 1:50 | 20% |
| — | Lectin-647 | Vector | DL-1177 | n.a | 1:250 | 60% |
| — | DAPI | Invitrogen | | 1 μg/μl | 10 μg/ul | 10% |

Note: laser power is particularly high for stains that were coupled in the far red channel (e.g., Lectin and Vimentin).

Specimen Mounting

Figures 3A, 3B, 3C:
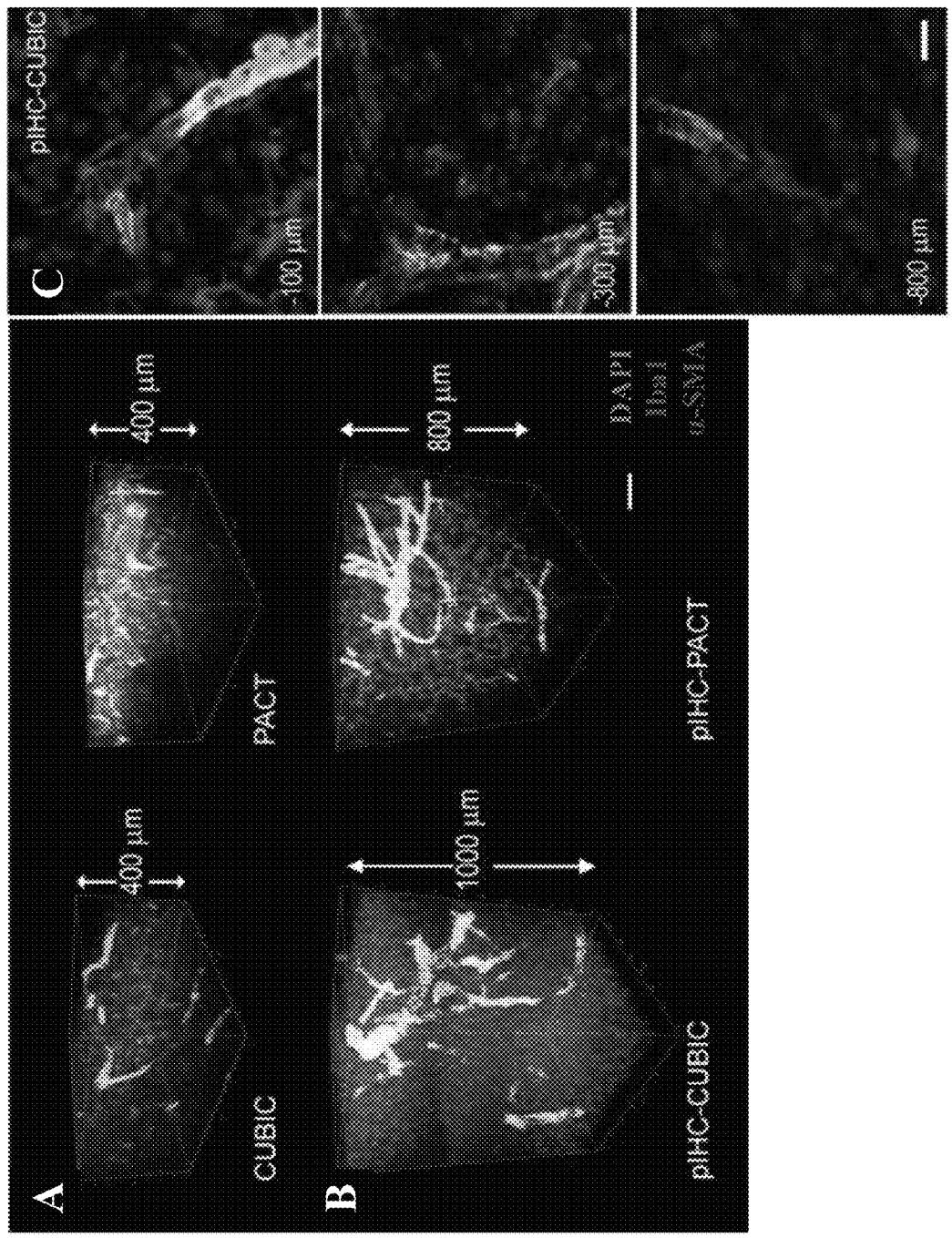
FIGS. 3A-3D 3D confocal images of human striatum immunolabeled with DAPI (blue), Iba1 (red), and α-SMA (green). Samples were cleared with CUBIC or PACT.

Refractive Index Matching Solution (RIMS) was made by adding 40 g of Histodenz™ (Sigma-Aldrich D2158) to 30 ml of 0.02M PB/0.01% $NaN_3$. Immunostained samples, either PACT- or CUBIC-cleared, were incubated in RIMS solution for 6 hrs. Blu Tack (Bostik) was used on conventional glass slides (VWR) to create a 1.5 mm-thick chamber where a single sample was submerged in RIMS and covered with a 0.15 mm coverslip (FIG. 3B). Slides were stored at 4° C.

Spectrophotometry—Measurement of Collimated Light Transmittance

After RIMS incubation, light transmittance (400-800 nm, with 10 nm steps) of the 1-mm-thick human brain tissue blocks was measured with a Flexstation 3 spectrophotometer (Molecular Devices).

Electron Microscopy

Clarified human brain samples were post-fixed in 2% osmium tetroxide, dehydrated, and embedded in Durcupan resin (Fluka; Sigma-Aldrich). Semithin sections (1.5 μm) were cut with a diamond knife and stained with 1% toluidine blue for light microscopy. Ultrathin sections (70-80 nm) were cut, stained with lead citrate, and examined under an FEI Tecnai G2 Spirit transmission electron microscope (FEI Europe) using a digital camera (Morada Soft Imaging System; Olympus).

Imaging & Analysis

Stained tissues were imaged on a Leica SPE system utilizing a 10× dry objective (NA of 0.30), or a Leica SP8 system using a 25× water objective (NA of 0.85). Comparative analysis of fluorescence intensity was performed on 400-μm confocal stacks (10 μm interval, thick sections) or 40-μm stacks (1 μm interval, thin sections). All comparative imaging was taken with identical parameters which were set on the most intense superficial signal using look-up table (LUT) Leica feature. Thick sections were imaged at the center, avoiding the sides which would introduce bias because of lateral antibody penetration. Image analysis was performed with Imaris (Bitplane) and ImageJ. Experiments were repeated three times on anatomically-matching samples from different donors. For each staining, fluorescence intensity was normalized to the highest data point obtained in each experiment. Data plotting and statistical analysis were performed with GraphPad Prism. Statistical analysis was performed via two-way ANOVA ($\alpha=0.05$) with the Šidák method for multiple comparisons.

High signal-to-noise ratio, lack of artifacts and low/medium laser power were used as indices for success of pIHC. The exclusion of lateral areas from quantification ensured that the imaged depth was a product of unbiased unidirectional antibody diffusion into the tissue. The laser power needed for imaging was, in most of the cases, in the lower range (Table 2), except for Alexa-647 fluorophores which require a laser power of 60% or higher (e.g., Vimentin and Tomato Lectin in Table 2). The intensity of the RIMS-stored immunostainings was quite resistant to fading, contrary to other studies[8]. When stored in darkness at 4° C., samples imaged 8 months after completion showed a minor signal quenching (FIG. 14).

Example 2. Non-Limiting Examples of Immunofluorescence Protocols

None-Cleared Tissue (1) Wash: 3 times for 5 minutes room temperature (typically using Phosphate buffer (0.01-0.1M) or Phosphate Buffer Saline (0.01-0.1M); (2) Antigen retrieval: 15 minutes at 95° C. or 30-45 minutes at 80° C. in a bath of Citrate Buffer (pH6); (3) Wash (as in (1)); (4) Blocking: 2 hrs RT, PB+0.4% Tx+10% Serum; (5) Wash (as in (1)); (6) Primary Antibody: 2 hrs RT or 8-48 hrs at 4° C. (primary antibodies are diluted in PB+0.4% Tx+2% Serum); (7) Wash (as in (1)); (8) Secondary Antibody: 2 hrs RT or 8-48 hrs at 4° C. (secondary antibodies are diluted in PB+0.4% Tx+2% Serum); (9) Additional steps: Dyes (e.g., DAPI, Lectins, Fluorescent Nissl) are normally added at the end of procedure (diluted in PB or PBTx) for 10 minutes to 4 hrs at 4° C. or RT. When biotinylated secondary antibodies are used, tissue is incubated with fluorescent streptdavidin in PBTx for 10 minutes to 4 hrs at 4° C. or RT.

Cleared Tissue (1) Wash: 3-6 times for 15 minutes room temperature (typically using Phosphate buffer (0.01-0.1M) or Phosphate Buffer Saline (0.01-0.1M); (2) Antigen retrieval: 15 minutes at 95° C. or 30-45 minutes at 80° C. in a bath of Citrate Buffer (pH6); (3) Wash (as in (1)); (4) Blocking: for thick cleared tissues, skipped in most cases; (5) Wash (as in (1)); (6) Primary Antibody: 2 hrs to 7 days at RT or 4° C. (primary antibodies are diluted in PB+0.4% Tx+2% Serum); (7) Wash (as in (1)); (8) Secondary Antibody: 2 hrs to 7 days at RT or 4° C. (secondary antibodies are diluted in PB+0.4% Tx+2% Serum); (9) Additional steps: Dyes (e.g., DAPI, Lectins, Fluorescent Nissl) are normally added at the end of procedure (diluted in PB or PBTx) for 10 minutes to 72 hrs at 4° C. or RT. When biotinylated secondary antibodies are used, tissue is incubated with fluorescent streptdavidin in PBTx for 10 minutes to 72 hrs at 4° C. or RT.

Alternative Protocol (1) Wash: as primary buffering agents for washes and for all the steps listed below, the following can also be used: TRIS-based solution, TBS (Tris-Borate Buffer), PB-Tx, PB-Tw, TBS-Tx, TBM-Tw, PBS-Tx, or PBS-Tw ("Tx" represents Triton-X; "Tw" represents Tween). Tx or Tween can be added at different concentrations (e.g., between 0.5-20%). Molarity of buffer solutions, and concentration of the Triton or Tween detergents, are user-defined and may vary depending on application; (2) Antigen retrieval: (i) Proteinase K in a solution of Tris BASE/EDTA/Triton-x at pH 7.0-8.0, for 5-20 minutes at a temperature between 20-60° C., typically 15 minutes at 37° C.; (ii) Citrate buffer, pH 4.5, at 80-95° C. for 15-45 minutes; (iii) TRIS buffer pH9.0, at 80-95° C. for 15-45 minutes; (iv) Ethanol 4° C. for 20 minutes; (v) Methanol 5 minutes at −20° C.; (3) Wash (as in (1)); (4) Blocking: There are various types of serum depending on the specie. Horse, Donkey, Goat, and Sheep are the most common. Concentration of serum may vary. Processing of serum may vary (e.g., serum can be heat-inactivated). Alternatives to serum include: 0.5-10% BSA, Casein Milk, commercially available proprietary formulations of blocking agents, (e.g., TopBlock). As for the diluting agent (PBTx) see discussion above for alternatives; (5) Wash (as in (1)); (6) Primary Antibody: see discussion on blocking agents and diluting solutions above; (7) Wash (as in (1)); (8) Secondary Antibody: see discussion on blocking agents and diluting solutions above.

Example 3. pIHC is Compatible with PACT and CUBIC

CUBIC[18] and PACT[25,32] are methods of passive clarification. While clearing is faster with strong solvents[29,33] or electrophoresis[4,22,34], passive clearing presents a lower risk of tissue damage[6,8,9,34], which is critical in the case of valuable human specimens. Suitability of clearing method depends on tissue type, clearing time, the presence of endogenous fluorescent proteins, and compatibility with IHC (see comparative tables in literature[3,5-7]). Both CUBIC and PACT combine chemical de-lipidation with refractive index (RI) matching[32] and are compatible with IHC in human tissue[5,16]. Moreover, both clearing methods rely on passive incubation of tissue in the respective clearing solutions, requiring little workload.

Established techniques for preservation, immunostaining, and imaging of post-mortem human brain samples were used[35,36].

PACT and CUBIC were equally successful in achieving transparency of fixed human brain tissue. CUBIC-treated tissue clarified in 7 days of R1 treatment, while PACT-cleared tissue reached transparency at day 14 upon incubation with RIMS (FIG. 2A). Samples from human caudate nucleus reached up to 70% absolute transparency at the end of the procedure (FIG. 2B), without major differences between PACT and CUBIC. Samples richer in white matter, such as the striatal and cerebellar (FIG. 2C) or callosal regions, had a slightly lower degree of transparency than grey-matter rich samples. Temporary loss of transparency occurred when the clear tissue was transferred into any water-based solution, but the transparency was always restored by the final RIMS incubation. Temporary tissue swelling of roughly 20% of the volume was noted with both procedures, as previously reported[4,9,32].

It was found that an average of 3 weeks, from the beginning of clearing to imaging, was acceptable. The use of recent, lightly fixed human formalin-fixed tissue allowed for such clearing time. In the case of archival tissue from long-term formalin storage[5,15,37] or paraffin-embedded blocks[14,16], clearing time can be up to several months.

As detailed in Example 3, in some aspects, CUBIC performed better than PACT. CUBIC showed a lesser degree of cytoarchitectural disruption (FIGS. 6A, 6B, and 6C), and lack of vascular autofluorescence (FIG. 5D). On the other hand, GFAP staining was superior in PACT samples (FIGS. 4A, 4B), confirming the notion of differences in antigenicity for certain proteins between clarification methods (Liu et al., 2016). Furthermore, the staining depth for Neurofilament (FIG. 13) and NeuN on CUBIC-cleared human or mouse cortical or cerebellar samples could not be improved by pressurization beyond the superficial 50 µm. These differences may be due to the specific action of chemicals used for clearing on individual proteins. For example, the urea used in CUBIC leads to partial denaturation of proteins[38]. On the other hand, delipidation-free and denaturant-free methods, while developed to decrease the degree of tissue disruption[14], still fail to produce IBA1 staining.

While CUBIC was described as a superior technique for IHC application[26], the original protocol was not as efficient in clearing human brain tissue as in other organs[16]. Application of higher temperature[26] during CUBIC clearing (e.g., 40° C.), however, achieved acceptable clarity. CUBIC requires the IHC protocol to be performed halfway through the protocol, hence exposing bound fluorescent antibodies at 40° C., causing minor fluorescence quenching[26]. This is because when a fluorescent tag (e.g., a protein or a tag lined to a secondary antibody) is subjected for a sustained period of time to high temperature (e.g., above room temperature), some fluorescence loss happens (i.e., the fluorescence is quenched). This is taken into consideration when CUBIC is applied, since the R2 incubations of CUBIC are performed at 40° C., after the end of the staining procedure (i.e., when the secondary antibodies are already in the tissue).

Example 4. Pressurization Improves Antibody Penetration

Cellular Markers

The sustained atmospheric pressure of 225 KPa (2.22 ATM) during incubations was applied to 3×3×1 mm tissue samples. The ability to improve the depth of antibody penetration and achieve uniform staining throughout the samples with high signal-to-noise ratio were assessed. Samples were incubated with primary and secondary antibodies in an air-tight chamber body of the pressurizing device as described in the methods section.

Figure 3D:
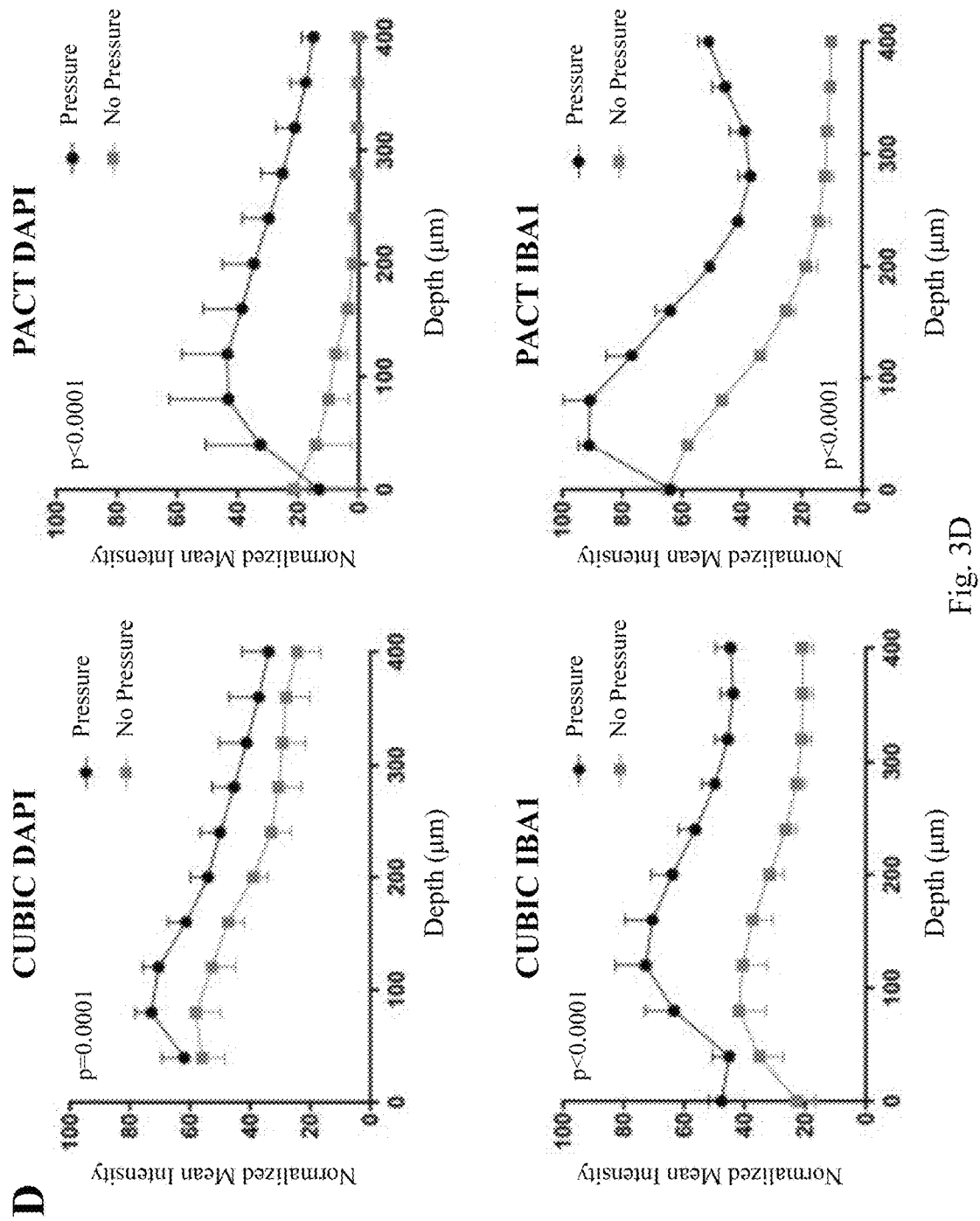

DAPI and antibodies for the microglia marker IBA1 (as well as the endothelial cell marker α-SMA) were combined in triple-channel IHC in caudate nucleus samples. Under free-diffusion conditions, a tendency for higher permeability, particularly for DAPI, was observed in CUBIC-treated samples relative to PACT-treated samples (FIG. 3A). Pressurization significantly increased the intensity and the depth of the staining in both conditions (FIG. 3B) as shown by quantification of staining intensity for DAPI and IBA1 in the first 400 µm (FIG. 3D). Below 400 µm, laser power compensation allowed imaging of all three stainings across the tissue thickness in pIHC-CUBIC, but not pIHC-PACT samples (FIG. 3B). In pIHC-CUBIC samples, co-localization of nuclei in microglia cells was seen throughout the sample with minor loss in morphology (FIG. 3C).

The intermediate filament protein GFAP is a pivotal marker widely used in neuroscience for the observation of normal and reactive glia, progenitors, and glioma cells. Anti-GFAP antibodies are notoriously trapped by the dense network of astroglial processes leading to antibody depletion[39] and poor penetration. Pressurization led to intense staining of GFAP+ astrocytes in pIHC-PACT, but not pIHC-CUBIC samples (FIGS. 3A, 3B). GFAP staining in p-IHC-PACT could be imaged with high resolution and no background (FIG. 4C) up to 300 µm from the surface using minimal laser power (e.g., 10%). Below 300 µm, an intense GFAP+ immunoreactivity marked scattered, isolated blood vessels (FIG. 4B inset). TEM analysis revealed that while astrocytes were identifiable in all conditions, intermediate filaments were better conserved in PACT compared to CUBIC samples (FIG. 4D).

Vascular Markers

Figures 5A, 5C:
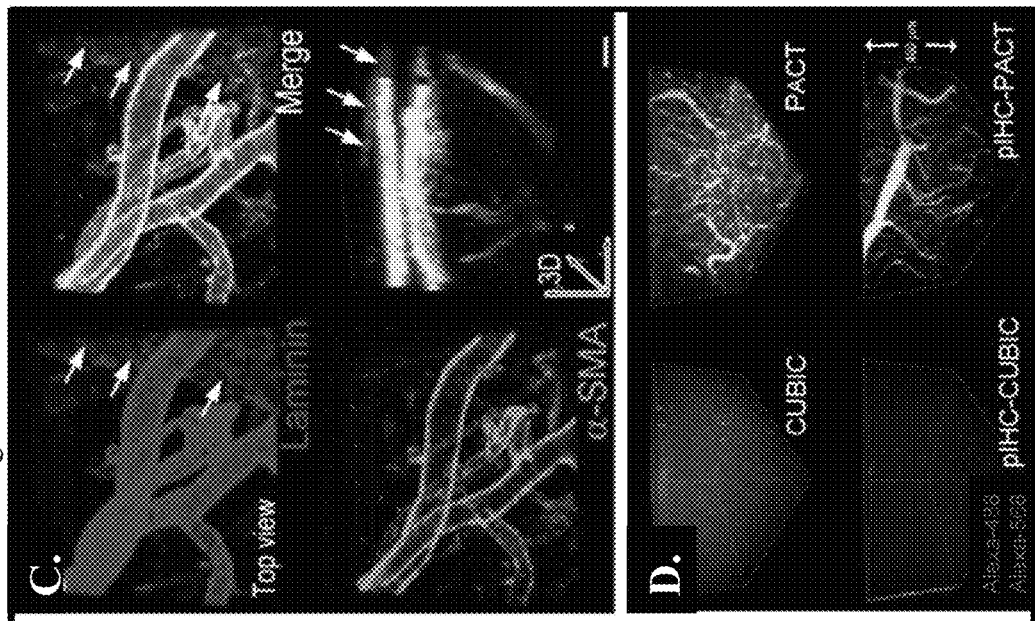
FIGS. 5A-5F Benefits of pressurization on vascular-associated staining.
Figures 5B, 5D:
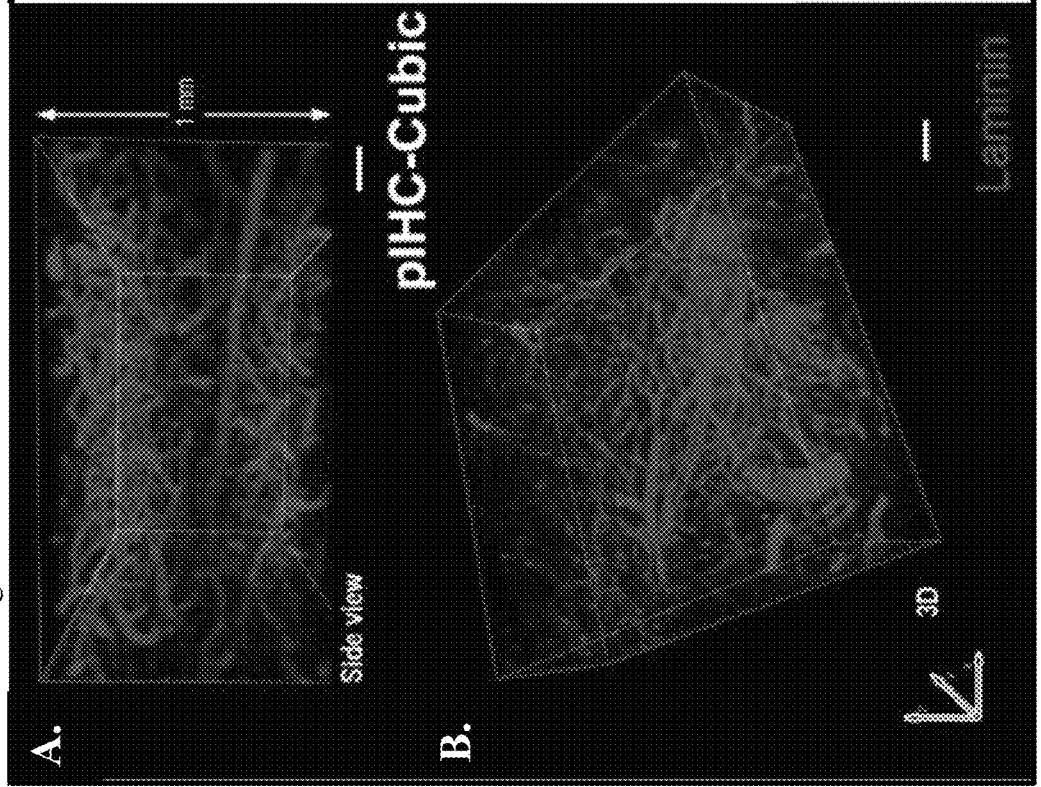

Pressurization also led to intense and complete immunostaining of the tissue tiles with Laminin, a ubiquitous marker of the external lamina surrounding blood vessels in the human brain (FIGS. 5A, 5B). Co-staining with α-SMA, expressed only in arterioles, showed that pressurization is compatible with co-localization (FIG. 5C). While PACT showed a strong autofluorescence of the entire vasculature, CUBIC was devoid of this problem (FIG. 5D). This was particularly evident at λ=488 nm, λ=568 nm, and laser power used being equal to or higher than 40%. TEM and H&E analysis suggest that the source of autofluorescence is residual erythrocytes inside the vessels of PACT samples, which are absent in CUBIC samples (FIGS. 5D, 6A, 6B, and 6C). Negative controls show that pressurization causes a net decrease in tissue background, independently of the type of clarification method used (FIG. 5D).

pIHC for vascular markers consistently granted complete staining in 1-mm thick tissue (FIGS. 3B, 5A, 7A, and 9A), including α-SMA which exceed penetration depths shown in independent studies using CUBIC[16]. This is due to two reasons—i) the overall density of any vascular marker in each Z-plane is generally lower than abundant cell populations such as astrocytes and microglia) pressurization likely generates a flow of the antibody solution through the vasculature. This is suggested by the deep scattered GFAP+ endfeet-enclosed structures shown in FIG. 4B inset, which appeared in areas otherwise devoid of GFAP staining, as well as by the vascular Vimentin pattern achieved in tumor xenograft samples. Vimentin is an intermediate filament protein found in progenitor cells and blood vessel walls[40]. Tumor tissue upregulates Vimentin and generating a network that limits the penetration of the antibody to the tissue surface (FIG. 12) similarly to GFAP. In the experiment shown in FIG. 9C, Vimentin antibody failed to penetrate in the tumor core, due to a surface-trapping effect, while producing a complete vascular pattern.

Pressurization was Crucial for Achieving Deep Staining

Figure 7B:
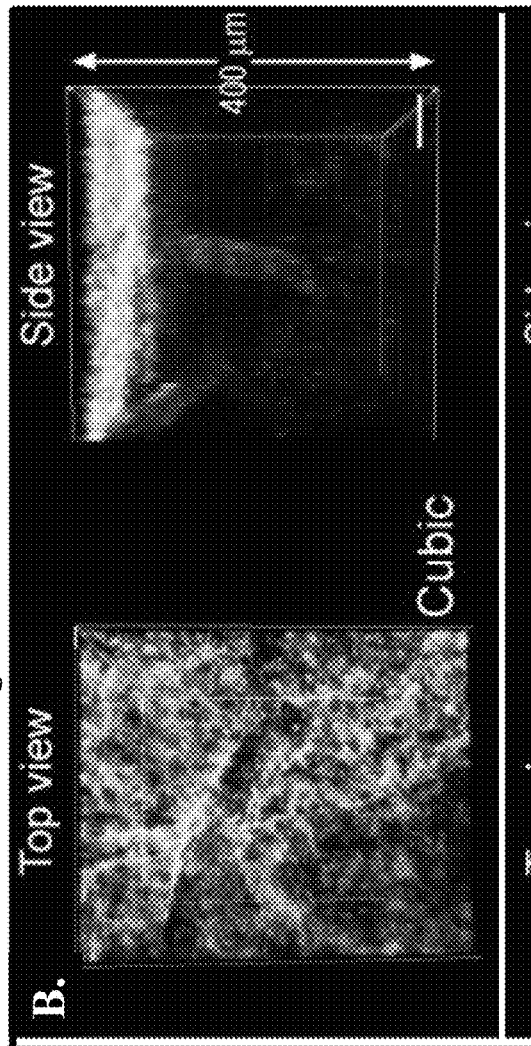
FIGS. 7A-7D pIHC staining of human cortical neurons.
Figure 7C:
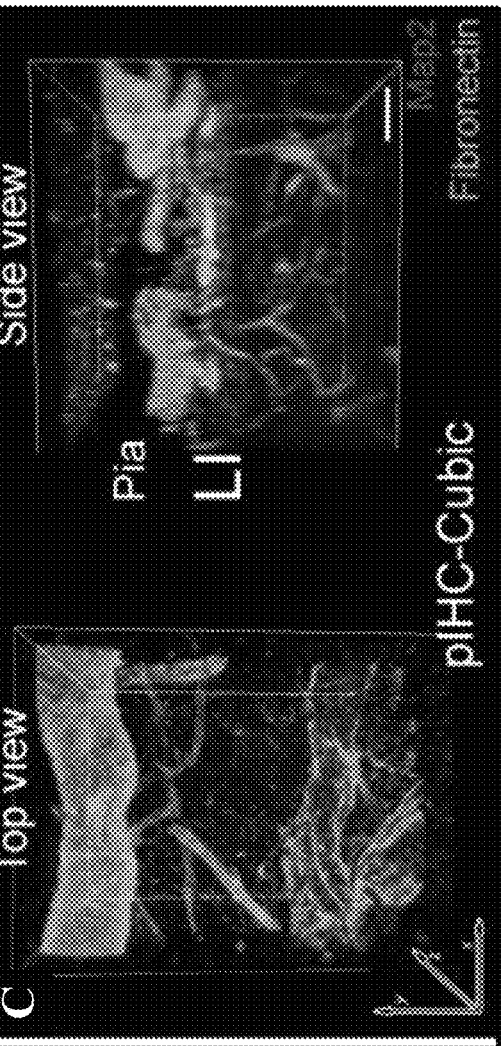
Figure 7A:
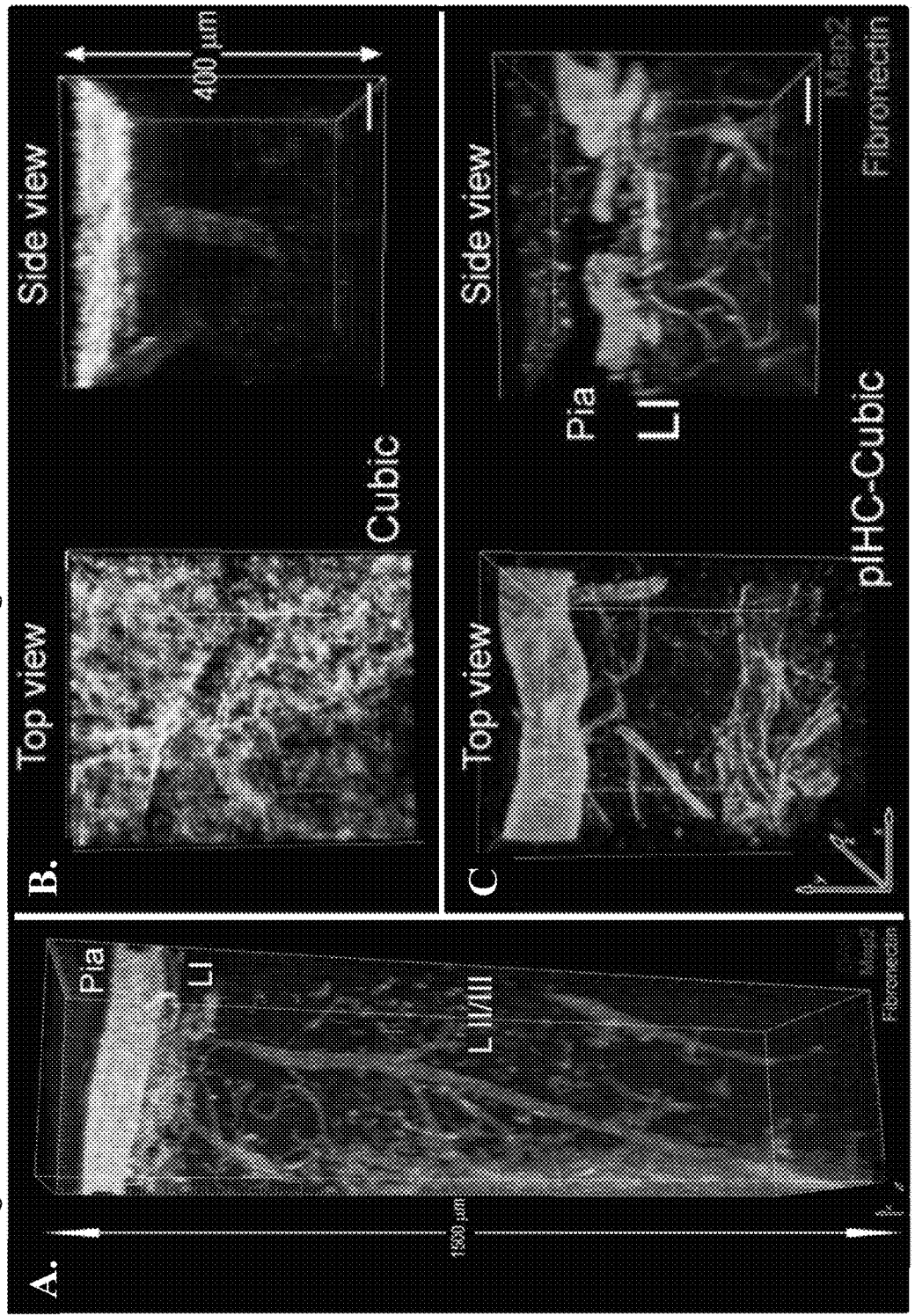

Immunostaining human cortical samples with the neuronal marker MAP2 and the ECM marker Fibronectin and top-down imaging from the pial surface introduce an additional level of complexity. To maintain an intact pia membrane in these preparations, larger samples (e.g., 5 mm×5 mm×5 mm) had to be used. All stainings could be imaged up to a depth of 1,500 µm (FIG. 7A). Once again, pressurization was crucial in achieving deep staining, since the pia membrane tends to block antibody penetration (FIGS. 7B, 7C). While TEM revealed that some level of lipid extraction was induced by both clearing procedures, the cytoplasmic membrane of neural cells could be distinguished only in CUBIC samples (FIG. 7C).

In sum, pIHC consistently increases fluorescent signals of cellular (IBAL MAP2, and GFAP) and vascular markers (α-SMA, LAMININ, VIMENTIN, and Lectin). pIHC also consistently reduces tissue background. Compared to non-pressurized controls, pIHC increases imaging depth by at least 2-folds.

Since the conception of IHC[41], improvements in specificity, duration, quality and tissue compatibility have been based on the development of novel bio-chemical agents. To our knowledge, this is the first time that antibody penetration in tissue and staining intensity are improved with elevated atmospheric pressure during antibody incubation.

Studies on embryonic tissue have reported successful imaging of large panels of antibodies[11,27,42], due to the higher permeability size and inherent transparency of such tissue compared to an adult. In an adult mouse or human brain, however, while single immunostainings deeper than 500 µm have been reported, such as Arc[43], Neurofilament[5], α-synuclein[5], TH[5,14,22], Iba1[28], αβ-plaques[7], and Parvalbumin[27], they are limited to one particular antibody or tissue type in most cases.

Using pIHC, imaging depth of cellular markers (MAP2, IBA1, GFAP) was significantly increased. The density of the target marker was known to influence penetration. GFAP staining[39] shows a limited depth (Reinier et al., 2014), because of the dense network of astrocytic fibrils acting as a net and impeding penetration. Up to 7 days of primary incubation are not sufficient to achieve an intense GFAP staining deeper than 120 µm under free diffusion conditions[14,15,39]. As each sample having a volume of 9 mm³, 10 µl of GFAP antibody stock allowed complete staining in 50% of the tissue volume in a single reaction (FIG. 4B). Conversely, using 5 µl of IBA-1 antibody stock, 100% of volume staining in tissue tiles from the same individual and brain region was achieved (FIG. 3B). While astrocytes and microglia are ubiquitous cell populations, there are obvious differences in the density of GFAP or IBA1 antigens. It is worth noting that while IBA1 staining achieved complete z-depth penetration here, it underperformed in other studies[14,31].

In sum, pIHC can be influenced by the density of the antigens and antibody used. Different antibodies show different tissue penetration[5], depending on size, concentration, and interactions between stains.

Example 5. Pressurization Did not Create Major Artifacts

Figures 5E, 5F:
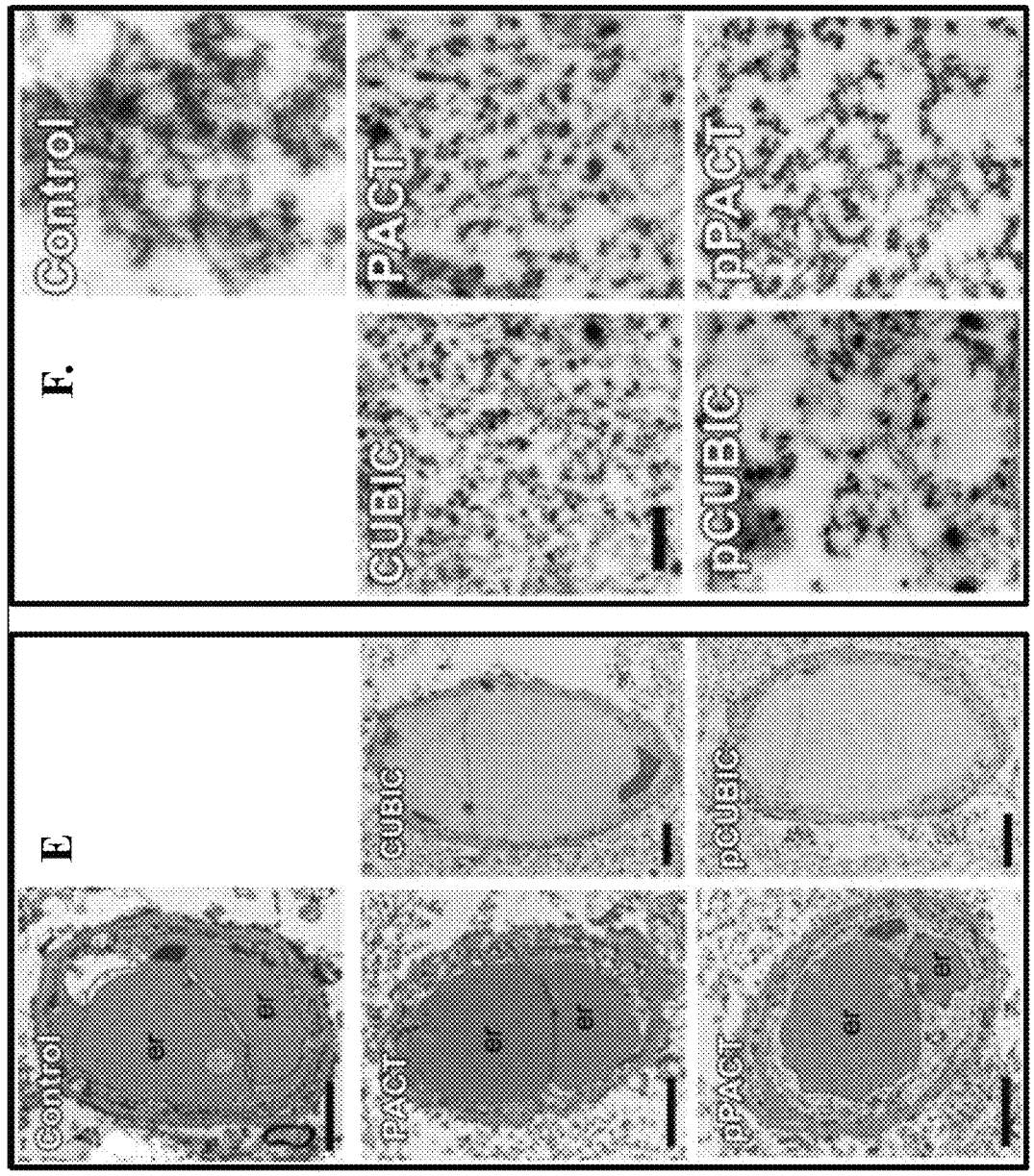
Figures 6A, 6B, 6C:
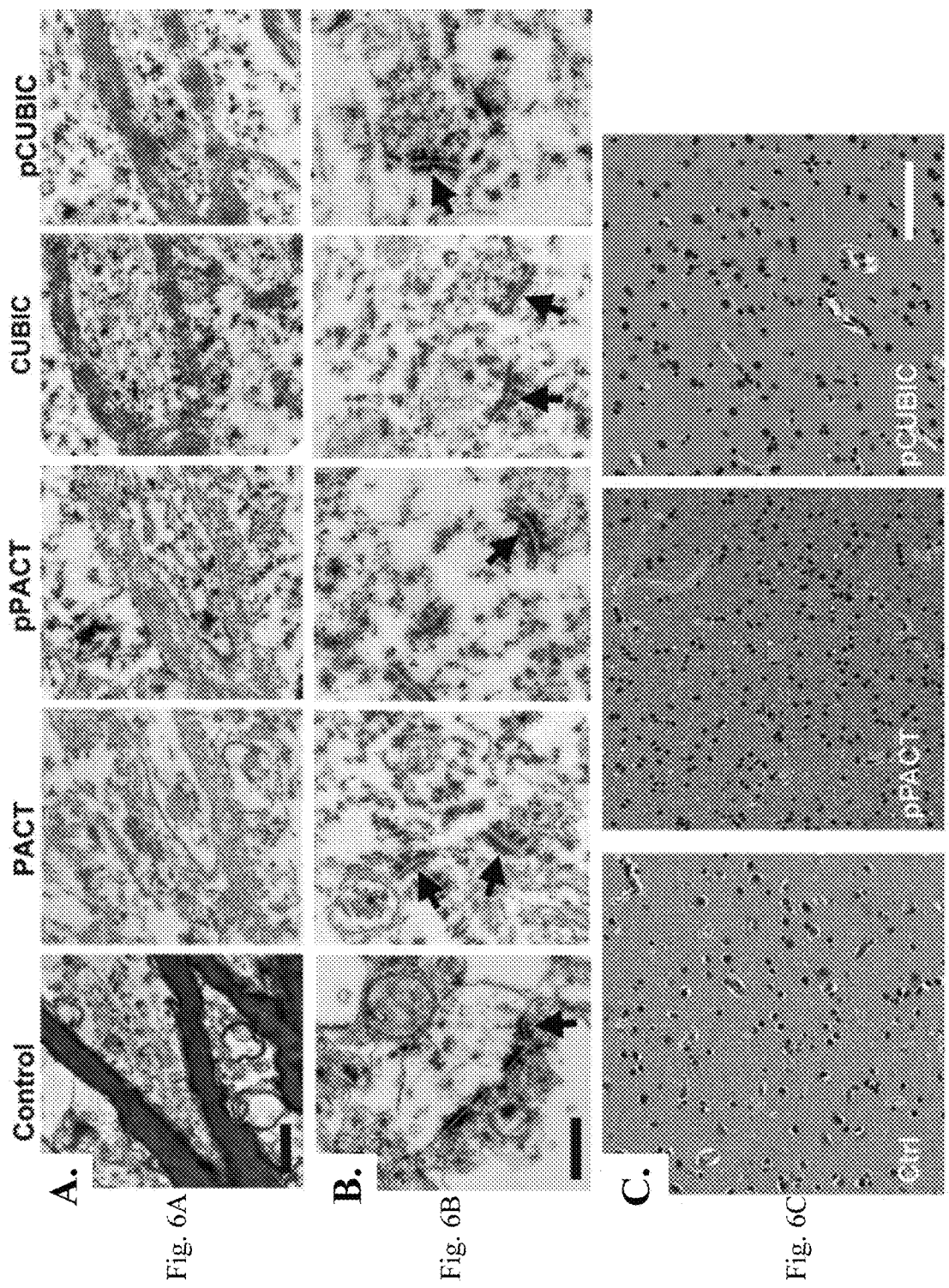
FIGS. 6A-6C TEM and H&E analysis of pressurized samples.

Under high TEM magnifications of cytosolic components of pressurized samples, an increase in protein aggregates and electron-lucent spaces were observed (FIG. 5F), suggesting washing out of soluble, unbound proteins in clarified tissue by pressurization. No other major tissue artifact was associated with pressurization except for a minor degree of vacuolization seen in H&E preparations (FIG. 6C).

Figure 7D:
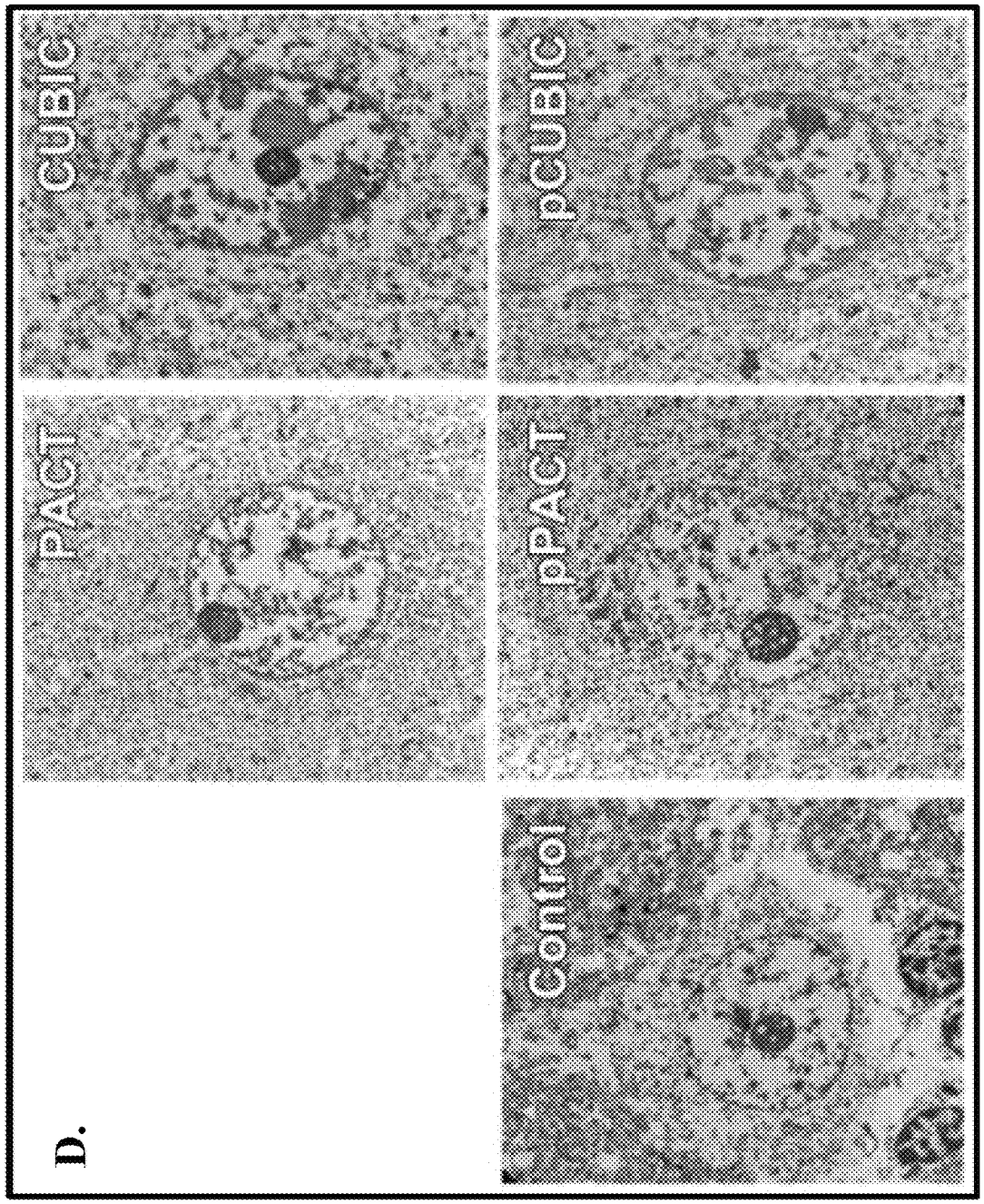
Figures 8A, 8B:
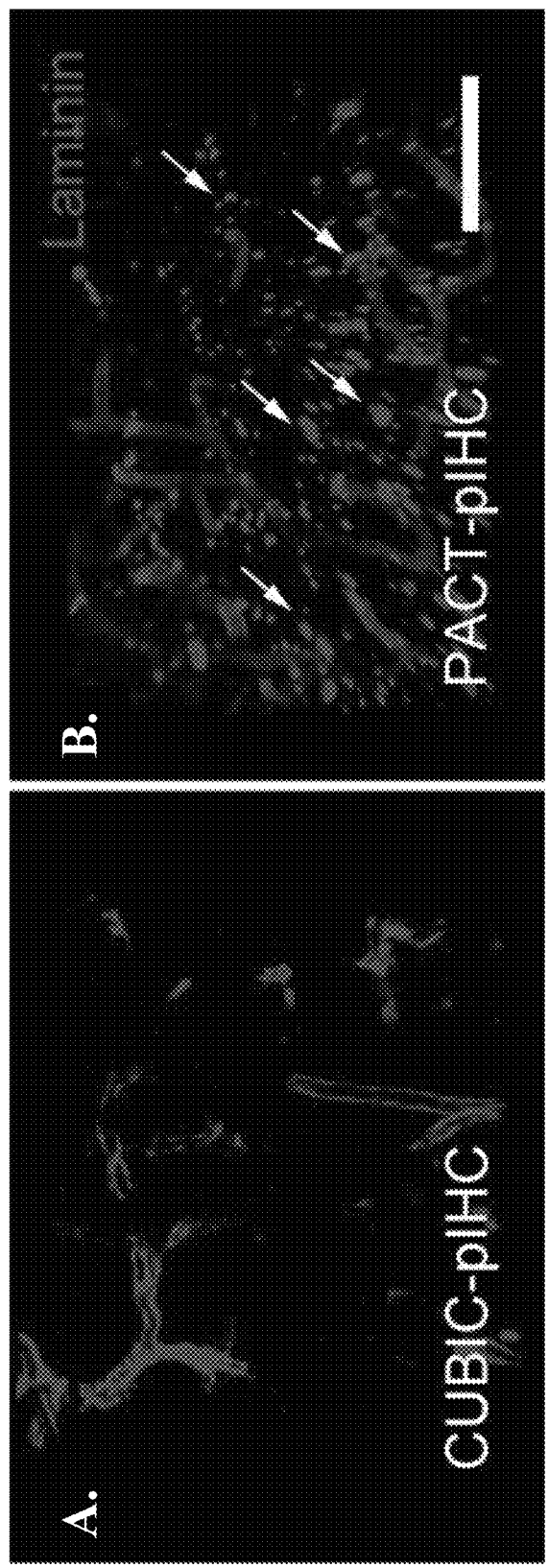
FIGS. 8A-8B Superficial artifacts in PACT samples. A maximum intensity projection of the superficial 20 μm of human striatum cleared with CUBIC (FIG. 8A) or PACT (FIG. 8B) and immunostained with pIHC for the vascular marker Laminin (red). Granular artifacts (arrows) consistently appeared in PACT-cleared samples. Scale bar: 100 μm.

However, the de-lipidization that occurs in both PACT and CUBIC leads to other unavoidable artifacts. The rough endoplasmic reticulum, characteristic of neurons, was also severely depleted. Nuclear architecture could still be recognized, with partially intact chromatin (FIG. 7D). Lipofuscin droplets were not affected by treatment. However, myelin components, neurofilaments, synaptic clefts and plasma membrane were better conserved in CUBIC samples than PACT (FIGS. 6A, 6B, and 6C). Finally, PACT samples, independent of the antibody used and of pressurization, tended to accumulate non-specific granular deposit in the most superficial (0 to 100 µm) aspects of the tissue (FIG. 8A, and 8B).

In sum, pIHC does not cause major artifacts or cytoarchitectural deformations.

Example 6. Compatibility of pIHC with Advanced Staining Techniques

Figures 9A, 9B, 9C:
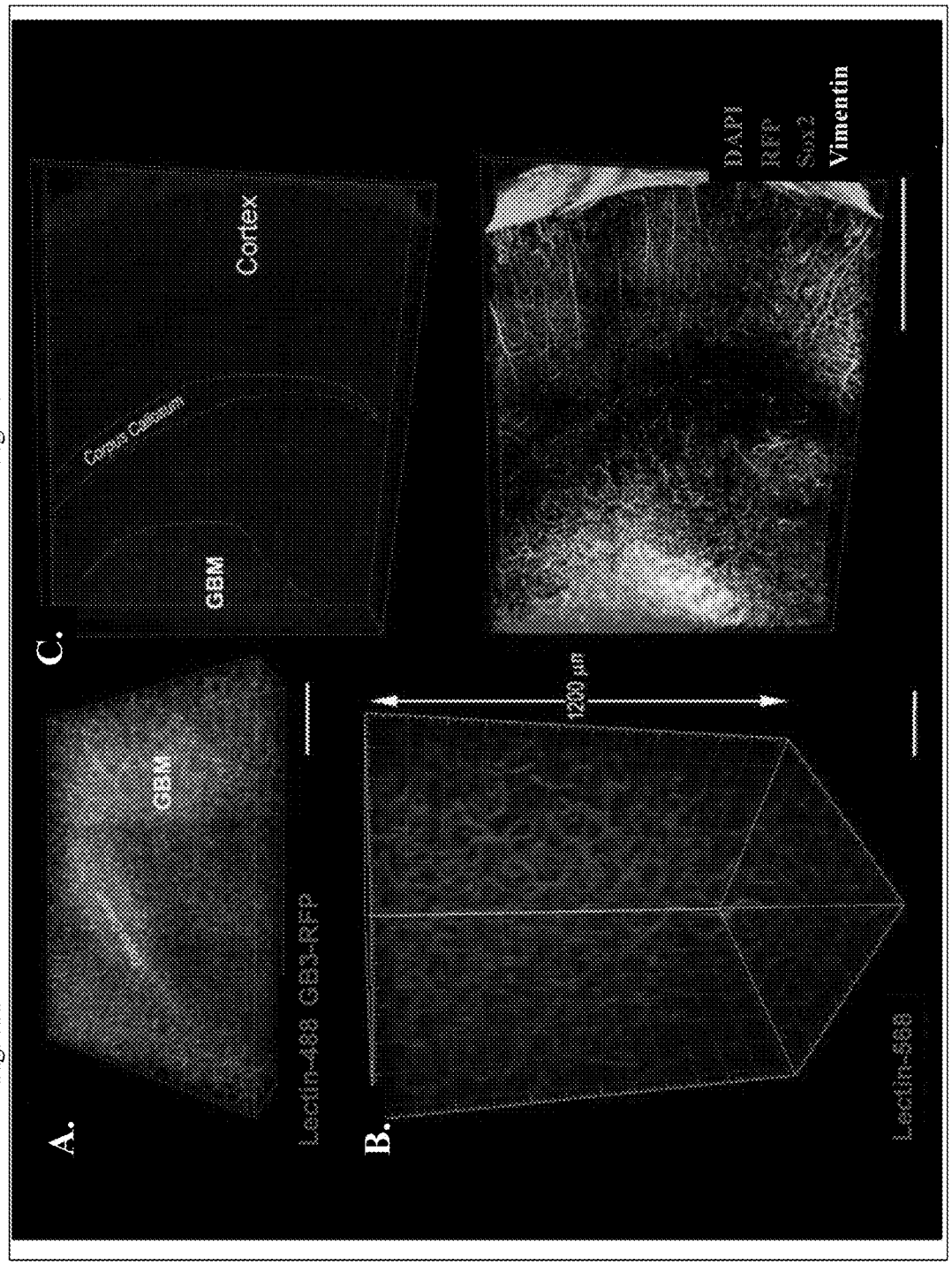

The compatibility of pIHC in mouse brain tissue was examined. Cells from an RFP-expressing primary human glioblastoma cell line (i.e., GB3-RFP) were injected unilaterally into the striatum of Nude mice to generate an endogenously RFP⁺ tumor model within one month from the injection. 1-mm sections of GB3-RFP brains were then clarified with CUBIC. Endogenous RFP fluorescence was preserved after clearing (FIG. 9A). Pressurized incubation with Tomato-lectin again affirmed the particular effectiveness of pressurization in vascular staining, allowing to stain the whole section in its thickness (FIGS. 9A, 9B). The tumor stem cell marker SOX2 could be visualized up to 400 µm from the surface, colocalized with the tumor environment and with migrating tumor cells (FIG. 9C). Interestingly, Vimentin revealed deep vessel-associated staining (FIG. 9C) extended on the pial surface of the brain while failing to penetrate beyond the surface in the tumor area. Finally, proliferating cells were detected using an anti-Ki-67 antibody, which requires heat-mediated antigen retrieval (AgR) for its detection. Heat is known to quench fluorophores such as RFP. Thus an RFP-rescuing protocol was performed (FIG. 9D). The sections maintained their integrity despite the prolonged heat treatment. Thus, the co-localization of proliferating RFP⁺ tumor cells around Lectin⁺ vessels across the whole thickness of the section could be imaged (FIG. 9E).

In sum, pIHC is compatible with mouse tissues and advanced staining techniques such as quadruple immunostainings and co-localization. Importantly, pIHC enabled rescue of RFP localization after heat-mediated antigen retrieval using a pre-incubation with a biotinylated secondary antibody (FIG. 9E).

Example 7. pIHC Accelerates Staining of Relatively Thin Samples

Figure 1B:
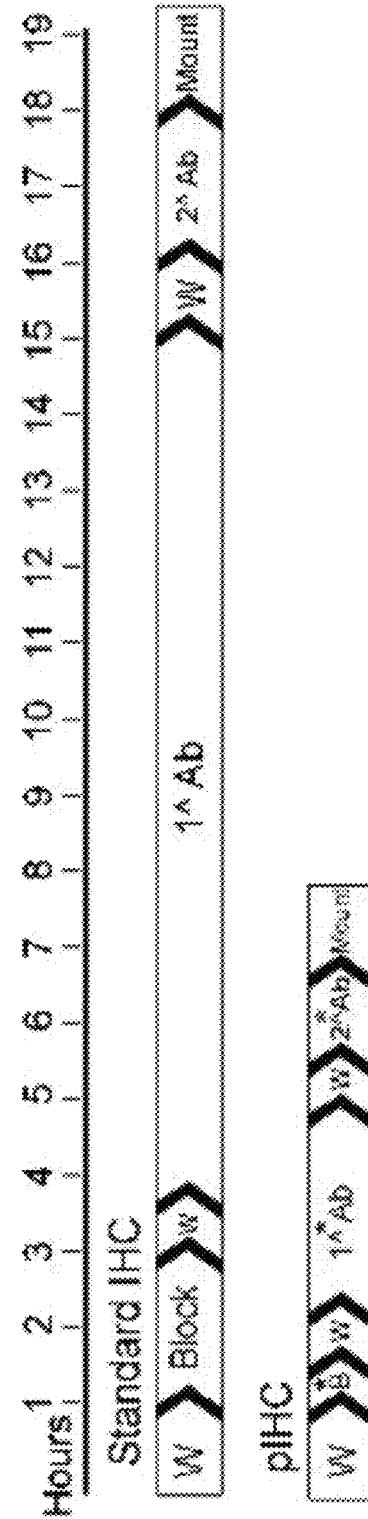

Conventional stainings on mouse thin (e.g., 40 µm) sections invariably require incubation of primary antibody between 8 and 48 hours. Whether pressurization at 225 kPa (2.22 ATM) could achieve a faster, uniform staining in free-floating 40 µm-thick mouse brain sections was tested. With pIHC, the overall workload time was adjusted to perform the whole staining in 8 hrs, compared to the 19 hrs of the conventional protocol (FIG. 1B). Pressurization of primary and secondary antibody was applied for 3 and 1 hour, respectively. The staining patterns we obtained with pIHC were equal to conventional free antibody diffusion, with no differences in the z-profile of fluorescence intensity and in the number of cells using 8 different markers (FIGS. 10B1, 10B2). Tissue sections did not show damage due to pressurization. Tests with 8 different markers (GFAP, Map2, Iba1, Neurofilament, Olig2, Ki-67, NeuN, Olig2, Lectin) showed no significant difference in the staining intensity across the z-plane (FIGS. 10A1-10B2), between pIHC and non-pressurized controls. These data demonstrate that pressurization increases antibody diffusion rate through tissue.

Example 8. pIHC Compared to c-PRESTO

The use of pressure for enhancing the tissue impregnation with chemicals was previously proposed to improve tissue fixation[21], although extreme pressure was used (e.g., 5000 psi). Recently, Lee and colleagues proposed PRESTO (pressure related efficient and stable transfer of macromolecules into organs), a technique involving the application of an external force to improve antibody penetration into PACT cleared tissue[22], either by centrifugation at 600 rcf (c-PRESTO[22]) or by a pump (s-PRESTO[44]). The latter requires an elaborate set-up, not allowing staining of multiple samples at the same time. Both PRESTO techniques rely on the application of a unidirectional force, while atmospheric pressure is multidirectional. Thus, we compared c-PRESTO and pIHC in parallel with a GFAP/DAPI staining on PACT-cleared samples (FIGS. 11A1-C2). C-PRESTO led to inconsistent and weak GFAP staining (FIG. 11B, 11C) compared to pIHC, although the performance with a small molecule (e.g., DAPI) was comparable.

Pressurization Device

Treating, preparing, or otherwise manipulating tissue and other materials while exposed to high pressure can sometimes provide improved effectiveness and/or efficiency, as discussed above. However, conventional chambered pressurization devices are often expensive. Additionally, they are often bulky, and can be difficult to move. Contemplated herein is a pressurizing device for tissue preparation that is able to expose tissue samples to high pressures, maintain those pressures for extended periods of time. Furthermore, the pressurizing device is configured to be easily moved, even while tissue is being treated, allowing it to be placed out of the way.

FIGS. 15 through 22 show various views of a non-limiting example of a pressurizing device for tissue preparation 100 (hereinafter pressurizing device 100 or device 100). Specifically, FIG. 15 is a perspective view of the front of the pressurizing device 100, FIG. 16 is a back view of the device 100, FIG. 17 is a top view, FIG. 18 is a bottom view, and FIG. 19 is a side view. FIGS. 15 through 19 show this non-limiting example of a pressurizing device 100 in a closed configuration, meaning the device 100 is or is ready to be pressurized. FIG. 20 is a perspective view of the front of the device 100 while it is in an open configuration, meaning the interior is accessible. FIG. 21 is a perspective view of the rear, and FIG. 22 is a front view of the device 100 while opened.

As shown, the pressurization device 100 comprises a chamber body 104, a chamber lid 102, a retainer 700, and an inlet 116. According to various embodiments, the device 100 may further comprise a pressure gauge 112, a safety release valve 114, and leveling feet 120. Each of these elements will be discussed in greater detail below.

Chamber Body

The chamber body 104 is a hollow or partially hollow structure within which an air-tight cavity can be formed and pressurized. As shown, the chamber body 104 has a top 106, a bottom 400, and one or more sidewalls 108 that connect the top 106 and bottom 400. In some embodiments, the shape of the chamber body 104 may be relatively simple (e.g. a single top, a single bottom, etc.). In other embodiments, the shape of the chamber body 104 may be more complex. For example, FIGS. 15-22 show a non-limiting example of a device 100 having a chamber body 104 that is "tiered", whose top 106 and bottom 400 each are made up of multiple surfaces, and which has more sidewalls 108 than a simpler, cubic body would. In some cases, such a shape may allow the body 104 to withstand greater pressures than a simpler shape might.

In some embodiments, the chamber body 104 may be cubic or rhombohedral in nature, while in others the chamber body 104 may have one or more non-planar surfaces (e.g. a cylindrical body, a spherical body, etc.). Those skilled in the art of pressurized cavities will recognize the advantages and disadvantages of various shapes for both the interior and exterior of the chamber body 104.

The chamber body 104 has an opening 604 through which the hollow inside may be accessed (in addition to the inlet 116, which will be discussed below). In some embodiments, the opening 604 is in the top 106, while in others the opening 604 may be in one or more sidewalls 108. In still other embodiments, the body 104 may have more than one opening 604. For example, in one embodiment, the chamber body 104 may have an opening 604 in both the top 106 and bottom 400, in addition to the inlet 116.

In some embodiments, the chamber body 104 may be formed from a single, integral piece or material (e.g. machined from a single block of metal, etc.). Such a construction may be advantageous in that it can provide greater strength. In other embodiments, the chamber body 104 may be formed from multiple pieces, which may be permanently or releasably coupled to each other. A chamber body 104 that can be broken down into multiple pieces may be easier to clean than a hollow body formed from a single piece of material.

According to various embodiments, one of the advantages the pressurizing device 100 has over conventional devices is that it is sized for the specific purpose of treating tissue, meaning sized to contain the structures that hold tissue samples. These sample receptacles will be discussed in greater detail below. By reducing the wasted volume within the air-tight cavity 606, the device 100 can be pressurized faster, with less gas.

In some embodiments, the size/volume of the hollow inside the chamber body 104 may be variable. For example, in some embodiments, the chamber body 104 may have a second opening in the bottom 400, surrounded by a lip having a seal. For smaller, shorter sample receptacles 600, such as a slide 900, a flap plate may be placed inside the hollow to cover the second opening, and the slides 900 placed on the plate. In one embodiment, the plate may be considered a retainer 700. Retainers will be discussed below in greater depth with respect to FIGS. 21-23. When more room is needed (e.g. treating multiple well plates stacked, etc.), a non-planar plate, or retainer, may be placed over the second opening, increasing the volume of the hollow by extending it downward. As an option, these plates may have one or more handles, or other structures, which may be sized to engage with the chamber lid 102 when it is placed over the opening 604 in the 106; the lid 102 may press the plate down into the seal around the second opening, making it stronger. As an option, the interchangeable plates that fit over the second opening may have different additional elements incorporated (e.g. heating/cooling elements, sensors, etc.), giving the device 100 greater versatility and expanding the number of applications.

As shown, in some embodiments, the chamber body 104 may comprise a plurality of leveling feet 120. According to various embodiments, these leveling feet 120 may be threadedly coupled to the bottom 400 of the chamber body 104 and configured such that their distance 200 from the chamber body 104 can be changed (e.g. rotating the foot to thread it up/down, etc.). The leveling feet 120 allow the device 100 to be made essentially level, preventing spills inside the air-tight cavity 606. In some embodiments, the leveling feet 120 may be composed of some sort of elastomer or other griping material, to prevent the device 100 from sliding if bumped, further protecting from unintentional jostles within the cavity 606.

As discussed above, some of the treatment methodologies that have been shown to benefit from being performed under high pressure take place on the scale of days. Once the device 100 has been loaded and pressurized, it may be advantageous to move it out of the way, where it can be monitored but is not taking up valuable workspace. As shown, some embodiments of the device 100 comprise one or more handles 118, which are coupled to the chamber body 104 and facilitate the transportation of the device 100.

Dimensions

As previously mentioned, the pressurizing devices 100 contemplated herein are advantageous in that they reduce the amount of wasted, pressurized space experienced in conventional devices. According to various embodiments, the chamber body 104 and/or chamber lid 102 may be sized and shaped such that one or more sample receptacles 600 may be held within the air-tight cavity 606 with minimal wasted space. In some embodiments, the shape of the air-tight cavity 606 may be somewhat irregular, made to efficiently receive a variety of common or anticipated sample receptacles used in tissue methodologies, rather than a larger, general purpose cavity.

As shown, the air-tight cavity 606 may have an associated volume 802 and height 800. In cases where the air-tight cavity 606 does not have a single height (e.g. a non-planar ceiling, etc.), then any discussion of the height 800 may be considered to be the average height of the cavity 606.

According to various embodiments, the height 800 of the air-tight cavity 606 within the device 100 may be between 1 inch and 3 inches. In other embodiments, the height 800 may be between 1 inch and 2 inches, or 3 inches and 5 inches. Furthermore, in some embodiments, the volume 802 of the cavity 606 may be between 25 cubic inches and 75 cubic inches, while in others it may be between 25 inches and 50 inches.

As a specific example, in some embodiments, the air-tight cavity 606 (which may or may not include a volume beyond the hollow interior of the chamber body 104, depending on the embodiment) may have a height of 1.25 inches, a width of 6.5 inches, and a depth of 3.84 inches, yielding a volume of 31.2 cubic inches. Those skilled in the art will recognize that embodiments of the device 100 targeted to specific applications using specific sample receptacles 600 may utilize other dimensions and/or volumes.

Chamber Lid & Lid Seal

As shown, the pressurizing device 100 further comprises a chamber lid 102 which, when placed over the opening 604, forms an air-tight cavity 606 with the chamber body 104. According to various embodiments, the chamber lid 102 is releasably coupled to the chamber body 104 proximate to the opening 604. In some embodiments, including the non-limiting example shown in FIGS. 15-19, the lid 102 is releasably coupled to the body 104 all around the perimeter of the opening 604. In other embodiments, the couplings may be non-homogenous and/or not evenly spread around the opening. For example, in one embodiment, the releasable coupling may be accomplished with one or more removable or releasable couplings (e.g. bolts, etc.) between the lid 102 and body 104, in conjunction with one or more permanent couplings, such as hinges or the like, allowing the lid 102 to move between an open configuration and a closed configuration.

According to various embodiments, the pressurizing device 100 may further comprise one or more lid seals 608. In the context of the present description and the claims that follow, a lid seal 608 is a structure or member that sits between the chamber lid 102 and the chamber body 104 and facilitates the formation of the air-tight cavity 606 by enhancing the connection between lid and body all around the opening 604. The lid seal 608 may be composed of an elastomer 610 or other material with elastomeric properties such that when squeezed between the lid and body, it conforms to the imperfections the their surfaces to form a much better seal. As an option, the lid seal(s) 608 may be coupled to the lid 102 or the body 104, and may sit in a groove in one of those structures. Furthermore, the seal(s) may also be replaceable, extending the lifespan of the device 100.

In some embodiments, the chamber lid 102 may be essentially planar, while in others it may be non-planar but essentially conform to the shape of the outside of the chamber body 104. In still other embodiments, including the embodiment shown in FIGS. 15-21, the chamber lid 102 may have a shape that deviates from the shape of the chamber body 104. Such deviations may be made to increase the volume of the air-tight cavity 606 that is formed, and/or may serve to increase the strength of the lid 102 by decreasing stresses.

The chamber lid 102 may be releasably coupled to the chamber body 104 through a variety of mechanisms. As shown, in some embodiments, the lid 102 may be bolted to the body 104 through a plurality of bolts 110. In some embodiments, the bolts 110 may be used alone, while in others they may be used in conjunction with a structure that serves to evenly spread the localized pressure of the bolts 110 across the entire lid 102, or at least the part of the lid 102 that is overlapping with the body 104 around the opening 604. See, for example, the plate that is between the lid 102 and the bolts 110 in FIG. 20.

Those skilled in the art will recognize that bolts 110 may be used in conjunction with, or replaced by, any other appropriate couplings known in the art that are strong enough to withstand the forces exerted by the pressurizing of the air-tight cavity 606. Examples of other coupling mechanisms include but are not limited to clamps, latches, levered claps (like locking pliers), and the like. In some embodiments, the couplings may be operated with standard tools (e.g. screwdriver, hex wrench, etc.). In other embodiments, the couplings may be operated manually without tools (e.g. knurled bolt heads, levers, latches, etc.). In still other embodiments, the couplings may be operated mechanically (e.g. actuated by an electric motor or the like, multiple couplings geared to operate in unison, etc.).

As previously mentioned, in some embodiments, the lid 102 may be permanently attached to the body 104, yet still able to move between open and closed configurations (e.g. on hinges, etc.). In other embodiments, including the non-limiting examples shown in FIGS. 15-22, the lid 102 may be completely removed from the body 104. While this may facilitate cleaning the interior of the device 100 and may maximize the amount of the opening 604 that is not obstructed without requiring additional space above or to the side of the device (e.g. to allow the lid to swing open, etc.), a completely detachable lid 102 may be difficult to properly align with the body 104 before coupling. According to various embodiments, the body 104 and/or lid 102 may further comprise one or more alignment pins 300 to facilitate the alignment of the lid 102 and body 104. Once the alignment pins 300 have slid into complementary recesses on the reciprocal chamber component, the lid 102 and body 104 are in alignment, and the true coupling may begin. Alignment may be facilitated by other mechanisms known in the art, including but not limited to magnets (e.g. when the chamber body 104 and lid 102 are not made of ferromagnetic materials, etc.), mated grooves and projections, and the like.

As an option, the coupling between the lid 102 and the body 104 may comprise one or more safety mechanisms, to prevent accidental release while the air-tight cavity 606 is pressurized. For example, in one embodiment, the lid or body may include a lock that does not allow the coupling(s) to be operated while the device 100 is pressurized.

Materials

The pressurizing device 100, including but not limited to the chamber lid 102 and the chamber body 104, may comprise any material that is capable of receiving and retaining a gas and maintaining an increased pressure for an extended period of time. In some embodiments, the intended pressures are such that polymer-based materials such as polypropylene, polystyrene, nylon, or other similar materials are appropriate. In other embodiments, the lid 102 and/or body 104 may be composed of resin, steel (e.g., stainless steel), copper, aluminum (e.g., cast aluminum) or any other metal or non-metal material that strong enough to withstand the higher end of contemplated pressures.

In some embodiments, the lid 102 and body 104 may comprise different materials (e.g., the lid 102 may comprise a polymer-based material and the body 104 may comprise a metal-based material). In other embodiments, they may be composed of the same material.

Retainer

In the context of the present description and the claims that follow, the retainer 700 is a structure that is coupled to the inside of the air-tight cavity 606 and is configured to couple with at least one sample receptacle 600. As previously described, a sample receptacle 600 is a structure designed to hold a tissue sample during treatment, preparation, or other procedure taking place in a pressurized environment. Examples of sample receptacles 600 include, but are not limited to, multi-well plates 602, slides 900, Eppendorf tubes, Eppendorf tube rack(s), and the like. These are other "treatment structures" are known to those skilled in the art. Specific applications and methodologies may call for specific receptacles 600. Typically conventional sample receptacles 600 are of solid constructions (e.g. no internal voids, etc.), making them impervious to the pressurized environments contemplated herein. However, some sample receptacles may need modification, in design and/or material, to withstand sustained pressurization.

In some embodiments, the retainer 700 is configured to releasably couple with the one or more sample receptacles 600. In other embodiments, one or more sample receptacles 600 may be permanently coupled, or even integral with, a retainer 700.

In some embodiments, the retainer 700 may be releasably coupled to the interior of the air-tight cavity 606. See, for example, the retainer 900 shown in FIG. 23, which is configured to releasably couple with a plurality of slides 900, and then releasably couple with the cavity 606. The ability to remove the retainer 900 may facilitate the loading of sample receptacles.

In other embodiments, the retainer may be integral with the air-tight cavity 606. Specifically, the retainer 700 may be integral with the portion of the chamber lid 102 and/or chamber body 104 that makes up the interior of the air-tight cavity 606. See, for example, the retainer 700 shown in FIGS. 21 and 22, comprising a restrainer bar 704 coupled to the lid 102 and a plurality of elastomer bumpers 808 coupled to the body 104. As an option, the bar 704 and bumpers 808 may both be removable, but are releasably or movably coupled to structures that are part of the retainer 700 are integral with the lid 102 and body 104. In still other embodiments, the retainer may be coupled, but not integral with, the lid 102 and/or the body 104.

Some retainers are configured for one specific type or variation of a sample receptacle 600. Other retainers may be configured to releasably couple with a variety of receptacles having similar structures. In still other embodiments, a retainer may be configured to releasably couple with multiple sample receptacles 600 (e.g. stacked multi-well plates, etc.).

According to various embodiments, the retainer may comprise one or more biasing elements that are coupled to the retainer and positioned and configured to press one or more sample receptacles against a portion of the retainer, lid, or body while the lid 102 is coupled to the body 104. The implementation of the biasing elements 702 facilitates the movement of a loaded pressurizing device 100 after it has been pressurized and the tissue has begun a long incubation or other process. Without the biasing elements, the sample receptacles 600 may move around inside the air-tight cavity 606 while the device 100 is being transported, possibly spilling or cross-contaminating.

Example A: Multi-Well Plate

As shown in FIGS. 21 and 22, the retainer 700 comprises a restrainer bar 704 that is movably coupled to the chamber lid 102 (e.g. can slide towards and away from the lid 102, but not detach), and biased away from the lid 102 by biasing elements 702 (i.e. springs) that are positioned between the lid 102 and the bar 704. The retainer 700 also comprises two elastomer bumpers 808 on the chamber body 104, opposite the restrainer bar 704. In operation, the restrainer bar 704 pushes against a multi-well plate 602 that has been inserted into the chamber body 104. When the lid 102 is bolted to the body 104, the multi-well plate 602 is squeezed between the restrainer bar 704 and the bumpers 808, holding it in place and preventing it from moving within the air-tight cavity 606. Those skilled in the art will recognize that this configuration may be adapted for use with other forms of sample receptacles 600.

Example B: Slides

As shown in FIG. 23, a retainer 900 may comprise an essentially flat surface and an array of biasing elements 906 that press back into the retainer surface to which they are coupled (unlike the restrainer bar of Example A). One or more of the biasing elements 906 may be used to secure slides 900 that have been loaded with a tissue sample 902 that has been prepared in accordance with the methodologies discussed above, or others that may also benefit from a pressurized environment.

In some embodiments, the slides 900 are of a conventional type (e.g., a gelatin slide). In other embodiments, the slides 900 may be disk-shaped. Further embodiments comprise applying a coverslip thereto.

Inlet & Gas Source

As shown, the pressurizing device 100 comprises at least one inlet 166 that passes through either the chamber body 104 or the chamber lid 102 and into the air-tight cavity 606. The inlet 166 is how the air-tight cavity 606 gets pressurized.

In some embodiments, the device 100 may have a single inlet 166. In other embodiments, the device 100 may have more than one inlet 166, allowing it to be connected to more than one gas source (e.g. different pressures, different types of gas, etc.). This may be advantageous if a particular application requires regular application of more one type/pressure of gas.

As previously discussed, the gas or fluid used to pressurize the cavity 606 may be atmosphere, nitrogen, carbon dioxide, or any other gas known to facilitate a treatment, preparation, or manipulation of a tissue. In some embodiments, the gas may come from a pressurized source, such as a tank or institutional supply (e.g. gas lines built into a lab space, etc.). In other embodiments, the gas may come from a low pressure or atmospheric source, and then be pressurized by a pump or like device before being sent into the cavity 606 through an inlet 166. As an option, in some embodiments, the pressurizing device 100 may further comprise a high-pressure pump integrated into the chamber body 104.

In some embodiments, the inlet 166 is simply an aperture in the device 100 to which a gas source may be coupled. In other embodiments, the inlet 166 may comprise a closable high pressure valve, such that once a target pressure has been reached, the valve on the inlet 166 may be closed, the gas source may be disconnected, and the device 100 moved to an out-of-the-way location. As will be discussed further below, in some embodiments, the valve on an inlet 166 may be electrically operated. Those skilled in the art will recognize that the valves may also be levers, actuators, or other devices that are capable of activating, controlling, and deactivating the flow of the gas.

In some embodiments, the device 100 may comprise a gas baffle within the air-tight cavity 606, proximate the inlet 166. The baffle may serve to lessen the turbulence of high pressure gas being shot into an enclosed space containing one or more tissue samples that may be exceptionally thin and apt to be blown away. The baffle may simply be a surface, or any other type of baffle known in the art.

Pressure & Safety Release Valve

As shown, some embodiments also include a safety release valve 114, which prevents the air-tight cavity 606 from rupturing, which may be violent and dangerous. The safety release valve 144 is in fluid communication with the cavity 606, and is rated for a pressure below the rupture point of the device in a closed configuration.

As discussed above, in some embodiments, the pressurizing device 100 may achieve and maintain a pressure within the air-tight cavity 606 of between 1.2 and 200 ATM. In other embodiments, the pressure may be even higher. Those skilled in the art will recognize that other processes, methodologies, and treatments may benefit from pressures even higher than that.

In some embodiments, the pressure within the cavity 606 is constant (discounting inconsequential fluctuation due to small ambient temperature changes near the device, and variations in barometric pressure). In other embodiments, the pressurizing device 100 may be configured such that, once reaching a target pressure, the pressure may be rapidly oscillated within a "pressure window", potentially accelerating the treatment. As a specific example, in one embodiment, a piston may be in fluid communication with the cavity 606, such that its operation rapidly increases and decreases the effective volume of the cavity 606, and thus the pressure.

Temperature

As mentioned above, in some embodiments, the temperature of the tissue being treated (and the materials being used in said treatment), may be optimally held at temperatures between 2° C. and 60° C. In some embodiments, the temperature inside the cavity 606 is allowed to fluctuate, while in others it may be actively controlled and maintained.

In some embodiments, the cavity 606 (or the chamber body 104 proximate the cavity 606) may comprise one or more temperature modification devices that may be used to increase or in some embodiments decrease the temperature within the cavity. FIG. 22 shows a non-limiting example of a device 100 having a cooling element 804 coupled to the air-tight cavity 606.

Sensors

In some embodiments, the pressurizing device 100 may comprise a pressure gauge 112. The pressure gauge 112 is in fluid communication with the air-tight cavity 606, whether it be physical exposure to an analog gauge such as the one depicted in FIG. 15, or communicatively coupled with an electronic pressure sensor inside the cavity 606. The pressure detected within the cavity 606 may be communicated through a gauge, an alarm, a screen, or any other means or method known in the art. As an option, in some embodiments, a target pressure may be set with the pressure gauge 112 that has been coupled to a processor, such that once the target pressure has been reached, a user is notified (e.g. speaker, light, electronic communication, etc.). Furthermore, such a configuration may also be used to detect and report if the pressure detected beings to deviate significantly from the target (e.g. the cavity 606 is leaking, etc.). In some embodiments, such events may be recorded in some form of log.

In some embodiments, the pressurizing device 100 may comprise a temperature sensor 806 inside or proximate to the cavity 606. In some embodiments, the temperature sensor 806 may be coupled to a processor and configured to alert a user when a temperature has been achieved (e.g. embodiments able to modify temperature, embodiments designed temperature manipulation from the outside, etc.) or if the measured temperature has deviated from a predefined range.

Depending on the application, one or more additional sensors may be incorporated into the device 100, including but not limited to cameras and photodiodes, pH meters, and the like. Another sensor, of a sort, that may be included is a timer, which may alert a user that a procedure has completed and the cavity 606 is ready for depressurization. Since the methodologies discussed above range in time from hours to a week or more, such an alarm may be especially useful if the device 100 has been moved to an out-of-the-way location.

Automation

In some embodiments, one or more aspects of the device 100 may be substantially or completely automated. For example, in some embodiments, one or more computers systems comprising memory and a processor can be employed to control one or more aspects of the pressurizing device 100.

Specifically, in some embodiments, after disposing the sample receptacle(s) 600 inside the cavity 606, the computer may automatically close and seal the device 100 and provide activation of the gas source pressurize the cavity 606. Moreover, in some embodiments, the computer may comprise functionality to monitor the pressure level within the cavity 606 such that the computer can augment pressure levels within the cavity 606 to ensure that the pressure levels remain within a desirable level.

Moreover, in some embodiments, the computer system may also be configured and arranged to control temperature of the cavity 606, or even different parts of the cavity 606. For example, as detailed in the methodology discussion above, some inventive methodologies employed with the device 100 may require different steps to occur at different temperatures (e.g., 4° C. or 95° C.) such that automated temperature control can be beneficial to the user.

In addition, in some embodiments, the computer may also comprise the functionality to control one or more fluidics systems. As described herein, during some inventive methodologies employed with the pressurizing device 100, one or more fluids may be added and removed to the sample receptacles 600 to process the tissue. In some embodiments, a substantially or completely automated system (i.e., controlled by the computer system) can be used to add and remove those fluids.

Additionally, the processor may be communicatively coupled to a pressure sensor and an electric valve coupled to the inlet 166 and configured to receive at least one of a target pressure and/or a target time. The electric valve may be operated programmatically to achieve and maintain the desired pressure. In some embodiments, instead of an electric valve, the device 100 may comprise a conventional valve and the ability to control the power of an external pump that is configured to provide gas through the inlet 166.

Agitation

In some embodiments, one or more of the sample receptacles 600 and/or the pressurizing device 100 itself can be configured to provide agitation to the tissue placed therein. For example, in some embodiments, the chamber body 104 may comprise an electric agitator 500 (e.g. vibrating motor 502, rotating motor, linear actuator, ultrasonic emitter, etc.) proximate the retainer and/or sample receptacles 600. As such, the agitation may facilitate circulation and re-circulation of the fluids used for the treatment, to improve the processes and methodologies contemplated herein.

As another example, in one embodiment, a linear actuator or rotary motor may be coupled to the chamber body 104 and configured to rotate the air-tight cavity 606 about an axis that is fixed with respect to a stationary base. The rotation may oscillate about an arc length chosen to agitate the tissue within the cavity without risk of spillage.

Applications

Numerous examples have been described above of treatments and procedures that have been shown to benefit from exposure to a high pressure atmosphere that is omnidirectional, such as the first and second clearing steps, and normalizing the refractive index of tissue. Embodiments of the pressurizing device 100 may have downstream applications that include immunohistochemistry and any other microscopy-based applications, such as immunofluorescence, electron microscopy (e.g., scanning electron microscopy or transmission electron microscopy), general confocal microscopy, super-resolution microscopy, light-sheet microscopy, and the like.

Applications may include the detection of bacterial/viral markers in human infected tissues, even thick tissues. The device 100 may also increase the speed and penetration of macromolecules (not only necessarily dyes or staining agents), and could be applied to any process of passive tissue incubation.

REFERENCES

1. Fiorelli R, Azim K, Fischer B, Raineteau O. Adding a spatial dimension to postnatal ventricular-subventricular zone neurogenesis. *Development* 2015; 142(12): 2109-20.
2. Bouvier D S, Jones E V, Quesseveur G, et al. High Resolution Dissection of Reactive Glial Nets in Alzheimer's Disease. *Sci Rep* 2016; 6: 24544.
3. Richardson D S, Lichtman J W. Clarifying Tissue Clearing. *Cell* 2015; 162(2): 246-57.
4. Chung K, Deisseroth K. CLARITY for mapping the nervous system. *Nat Methods* 2013; 10(6): 508-13.
5. Liu A K, Hurry M E, Ng O T, et al. Bringing CLARITY to the human brain: visualization of Lewy pathology in three dimensions. *Neuropathol Appl Neurobiol* 2016; 42(6): 573-87.
6. Hama H, Hioki H, Namiki K, et al. ScaleS: an optical clearing palette for biological imaging. *Nat Neurosci* 2015; 18(10): 1518-29.
7. Chen L, Li G, Li Y, et al. Ubas M: An effective balanced optical clearing method for intact biomedical imaging. *Sci Rep* 2017; 7(1): 12218.
8. Stefaniuk M, Gualda E J, Pawlowska M, et al. Light-sheet microscopy imaging of a whole cleared rat brain with Thy1-GFP transgene. *Sci Rep* 2016; 6: 28209.
9. Susaki E A, Tainaka K, Perrin D, et al. Whole-brain imaging with single-cell resolution using chemical cocktails and computational analysis. *Cell* 2014; 157(3): 726-39.
10. Tainaka K, Kubota S I, Suyama T Q, et al. Whole-body imaging with single-cell resolution by tissue decolorization. *Cell* 2014; 159(4): 911-24.
11. Zheng H, Rinaman L. Simplified CLARITY for visualizing immunofluorescence labeling in the developing rat brain. *Brain Struct Funct* 2016; 221(4): 2375-83.
12. Gong H, Xu D, Yuan J, et al. High-throughput dual-colour precision imaging for brain-wide connectome with cytoarchitectonic landmarks at the cellular level. *Nat Commun* 2016; 7: 12142.
13. Lai H M, Liu A K, Ng W L, et al. Rationalisation and Validation of an Acrylamide-Free Procedure in Three-Dimensional Histological Imaging. *PLoS One* 2016; 11(6): e0158628.
14. Lai H M, Liu A K L, Ng H H M, et al. Next generation histology methods for three-dimensional imaging of fresh and archival human brain tissues. *Nat Commun* 2018; 9(1): 1066.
15. Morawski M, Kirilina E, Scherf N, et al. Developing 3D microscopy with CLARITY on human brain tissue: Towards a tool for informing and validating MRI-based histology. *Neuroimage* 2017.
16. Nojima S, Susaki E A, Yoshida K, et al. CUBIC pathology: three-dimensional imaging for pathological diagnosis. *Sci Rep* 2017; 7(1): 9269.

17. Costantini I, Ghobril J P, Di Giovanna A P, et al. A versatile clearing agent for multi-modal brain imaging. *Sci Rep* 2015; 5: 9808.
18. Susaki E A, Tainaka K, Perrin D, Yukinaga H, Kuno A, Ueda H R. Advanced CUBIC protocols for whole-brain and whole-body clearing and imaging. *Nat Protoc* 2015; 10(11): 1709-27.
19. Kim S Y, Cho R I, Murray E, et al. Stochastic electrotransport selectively enhances the transport of highly electromobile molecules. *Proc Natl Acad Sci USA* 2015; 112(46): E6274-83.
20. Murray E, Cho R I, Goodwin D, et al. Simple, Scalable Proteomic Imaging for High-Dimensional Profiling of Intact Systems. *Cell* 2015; 163(6): 1500-14.
21. Chesnick I E, Mason J T, O'Leary T J, Fowler C B. Elevated Pressure Improves the Rate of Formalin Penetration while Preserving Tissue Morphology. *J Cancer* 2010; 1: 178-83.
22. Lee E, Choi J, Jo Y, et al. ACT-PRESTO: Rapid and consistent tissue clearing and labeling method for 3-dimensional (3D) imaging. *Sci Rep* 2016; 6: 18631.
23. Waldvogel H J, Curtis M A, Baer K, Rees M I, Faull R L. Immunohistochemical staining of post-mortem adult human brain sections. *Nat Protoc* 2006; 1(6): 2719-32.
24. Mehta S, Huillard E, Kesari S, et al. The central nervous system-restricted transcription factor Olig2 opposes p53 responses to genotoxic damage in neural progenitors and malignant glioma. *Cancer Cell* 2011; 19(3): 359-71.
25. Tomer R, Ye L, Hsueh B, Deisseroth K. Advanced CLARITY for rapid and high-resolution imaging of intact tissues. *Nat Protoc* 2014; 9(7): 1682-97.
26. Yu T, Qi Y, Zhu J, et al. Elevated-temperature-induced acceleration of PACT clearing process of mouse brain tissue. *Sci Rep* 2017; 7: 38848.
27. Hsueh B, Burns V M, Pauerstein P, et al. Pathways to clinical CLARITY: volumetric analysis of irregular, soft, and heterogeneous tissues in development and disease. *Sci Rep* 2017; 7(1): 5899.
28. Liebmann T, Renier N, Bettayeb K, Greengard P, Tessier-Lavigne M, Flajolet M. Three-Dimensional Study of Alzheimer's Disease Hallmarks Using the iDISCO Clearing Method. *Cell Rep* 2016; 16(4): 1138-52.
29. Renier N, Wu Z, Simon D J, Yang J, Ariel P, Tessier-Lavigne M. iDISCO: a simple, rapid method to immunolabel large tissue samples for volume imaging. *Cell* 2014; 159(4): 896-910.
30. Sung K, Ding Y, Ma J, et al. Simplified three-dimensional tissue clearing and incorporation of colorimetric phenotyping. *Sci Rep* 2016; 6: 30736.
31. Xu N, Tamadon A, Liu Y, et al. Fast free-of-acrylamide clearing tissue (FACT)—an optimized new protocol for rapid, high-resolution imaging of three-dimensional brain tissue. *Sci Rep* 2017; 7(1): 9895.
32. Treweek J B, Chan K Y, Flytzanis N C, et al. Whole-body tissue stabilization and selective extractions via tissue-hydrogel hybrids for high-resolution intact circuit mapping and phenotyping. *Nat Protoc* 2015; 10(11): 1860-96.
33. Erturk A, Lafkas D, Chalouni C. Imaging cleared intact biological systems at a cellular level by 3DISCO. *J Vis Exp* 2014; (89).
34. Woo J, Lee M, Seo J M, Park H S, Cho Y E. Optimization of the optical transparency of rodent tissues by modified PACT-based passive clearing. *Exp Mol Med* 2016; 48(12): e274.
35. Sanai N, Nguyen T, Ihrie R A, et al. Corridors of migrating neurons in the human brain and their decline during infancy. *Nature* 2011; 478(7369): 382-6.
36. Sanai N, Tramontin A D, Quinones-Hinojosa A, et al. Unique astrocyte ribbon in adult human brain contains neural stem cells but lacks chain migration. *Nature* 2004; 427(6976): 740-4.
37. Phillips J, Laude A, Lightowlers R, Morris C M, Turnbull D M, Lax N Z. Development of passive CLARITY and immunofluorescent labelling of multiple proteins in human cerebellum: understanding mechanisms of neurodegeneration in mitochondrial disease. *Sci Rep* 2016; 6: 26013.
38. Ke M T, Fujimoto S, Imai T. SeeDB: a simple and morphology-preserving optical clearing agent for neuronal circuit reconstruction. *Nat Neurosci* 2013; 16(8): 1154-61.
39. Liu A K L, Lai H M, Chang R C, Gentleman S M. Free of acrylamide sodium dodecyl sulphate (SDS)-based tissue clearing (FASTClear): a novel protocol of tissue clearing for three-dimensional visualization of human brain tissues. *Neuropathol Appl Neurobiol* 2017; 43(4): 346-51.
40. Schnitzer J, Franke W W, Schachner M. Immunocytochemical demonstration of vimentin in astrocytes and ependymal cells of developing and adult mouse nervous system. *J Cell Biol* 1981; 90(2): 435-47.
41. Coons A H, Kaplan M H. Localization of antigen in tissue cells; improvements in a method for the detection of antigen by means of fluorescent antibody. *J Exp Med* 1950; 91(1): 1-13.
42. Belle M, Godefroy D, Couly G, et al. Tridimensional Visualization and Analysis of Early Human Development. *Cell* 2017; 169(1): 161-73 e12.
43. Pacheco S, Wang C, Chawla M K, et al. High resolution, high speed, long working distance, large field of view confocal fluorescence microscope. *Sci Rep* 2017; 7(1): 13349.
44. Lee E, Sun W. ACT-PRESTO: Biological Tissue Clearing and Immunolabeling Methods for Volume Imaging. *J Vis Exp* 2016; (118).

What is claimed is:

1. A pressurizing device for tissue preparation, comprising:
a chamber body that is hollow, having a top, a bottom, and at least one sidewall, the chamber body further comprising an opening in one of the top of the chamber body and one of the at least one sidewall;
a chamber lid covering the opening and releasably coupled to the chamber body proximate the opening through a plurality of bolts, the chamber lid and chamber body forming an air-tight cavity;
a pressurized gas inlet passing through one of the chamber body and the chamber lid and into the air-tight cavity; and
a retainer integral with the air-tight cavity, the retainer comprising at least one biasing element coupled to the retainer, each of the at least one biasing elements positioned to press at least one tissue sample receptacle against a portion of the retainer while the chamber lid is coupled to the chamber body.

2. The pressurizing device of claim 1, the retainer further comprising a restrainer bar movably coupled to the chamber lid and biased away from the chamber lid by the at least one biasing element, and at least one bumper coupled to the chamber body opposite the restrainer bar, the restrainer bar positioned to press the at least one sample receptacle against the at least one bumper while the chamber lid is coupled to the chamber body.

3. The pressurizing device of claim 1, further comprising a plurality of leveling feet threadedly coupled to the chamber body outside the air-tight cavity, each leveling foot of the plurality of leveling feet held a distance from the chamber body that is adjustable by rotating the leveling foot.

4. The pressurizing device of claim 1, further comprising:
a cooling element in thermal contact with the air-tight cavity; and
a temperature sensor coupled to the air-tight cavity.

5. The pressurizing device of claim 1, wherein the air-tight cavity has a height between one inch and three inches, and a volume between 25 cubic inches and 75 cubic inches.

6. A pressurizing device for tissue preparation, comprising:
a chamber body, having a top, a bottom, and at least one sidewall, the chamber body further comprising an opening in one of the top of the chamber body and one of the at least one sidewall;
a chamber lid covering the opening and releasably coupled to the chamber body proximate the opening, the chamber lid and chamber body forming an air-tight cavity;
a pressurized gas inlet passing through one of the chamber body and the chamber lid and into the air-tight cavity; and
a retainer coupled inside the air-tight cavity and configured to releasably couple to a plurality of tissue sample receptacles, the retainer comprising at least one biasing element coupled to the retainer, each of the at least one biasing elements positioned to press a plurality of tissue sample receptacles against a portion of the retainer while the chamber lid is coupled to the chamber body.

7. The pressurizing device of claim 6, wherein the retainer is integral with at least one of the chamber body and the chamber lid.

8. The pressurizing device of claim 6, wherein the retainer is releasably coupled to the air-tight cavity.

9. The pressurizing device of claim 6, further comprising a lid seal composed of an elastomer and positioned around the opening and between the chamber body and the chamber lid when the chamber lid is releasably coupled to the chamber body.

10. The pressurizing device of claim 6, wherein the chamber lid is releasably coupled to the chamber body proximate the opening through a plurality of bolts.

11. The pressurizing device of claim 6, wherein the plurality of sample receptacles comprises at least one of: a multi-well plate, a plurality of slides, and an Eppendorf tube rack.

12. The pressurizing device of claim 6, wherein the air-tight cavity has a height between one inch and three inches, and a volume between 25 cubic inches and 75 cubic inches.

13. The pressurizing device of claim 6, further comprising:
a cooling element in thermal contact with the air-tight cavity; and
a temperature sensor coupled to the air-tight cavity.

14. The pressurizing device of claim 6, further comprising an electric agitator coupled to the chamber body, wherein the electric agitator is one of a motor, a linear actuator, and an ultrasonic emitter.

15. A pressurizing device for tissue preparation, comprising:
a chamber body, having a top, a bottom, and at least one sidewall, the chamber body further comprising an opening in one of the top of the chamber body and one of the at least one sidewall;
a chamber lid covering the opening and releasably coupled to the chamber body proximate the opening, the chamber lid and chamber body forming an air-tight cavity;
a pressurized gas inlet passing through one of the chamber body and the chamber lid and into the air-tight cavity; and
a retainer coupled inside the air-tight cavity and configured to releasably couple to at least one tissue sample receptacles, the retainer comprising a restrainer bar movably coupled to the chamber lid and biased away from the chamber lid by at least one biasing element, and at least one bumper coupled to the chamber body opposite the restrainer bar, the restrainer bar positioned to press the plurality of sample receptacles against the at least one bumper while the chamber lid is coupled to the chamber body.

16. The pressurizing device of claim 15, further comprising a lid seal composed of an elastomer and positioned around the opening and between the chamber body and the chamber lid when the chamber lid is releasably coupled to the chamber body proximate the opening through a plurality of bolts.

17. The pressurizing device of claim 15, wherein the at least one sample receptacle comprises at least one of: a multi-well plate, a plurality of slides, and an Eppendorf tube rack and the air-tight cavity has a height between one inch and three inches, and a volume between 25 cubic inches and 75 cubic inches.

18. The pressurizing device of claim 15, further comprising:
a cooling element in thermal contact with the air-tight cavity; and
a temperature sensor coupled to the air-tight cavity.

19. The pressurizing device of claim 15, wherein the retainer is releasably coupled to the air-tight cavity.

20. The pressurizing device of claim 15, further comprising an electric agitator coupled to the chamber body, wherein the electric agitator is one of a motor, a linear actuator, and an ultrasonic emitter.

* * * * *